US011857329B2

(12) United States Patent
Gabrin et al.

(10) Patent No.: US 11,857,329 B2
(45) Date of Patent: Jan. 2, 2024

(54) MODULAR GARMENT FOR A WEARABLE MEDICAL DEVICE

(71) Applicant: ZOLL Medical Corporation, Chelmsford, MA (US)

(72) Inventors: Michael J Gabrin, Pittsburgh, PA (US); Christopher L Swenglish, Connellsville, PA (US); Gary A Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 17/809,135

(22) Filed: Jun. 27, 2022

(65) Prior Publication Data

US 2022/0338782 A1    Oct. 27, 2022

Related U.S. Application Data

(62) Division of application No. 16/455,823, filed on Jun. 28, 2019, now Pat. No. 11,412,973.

(51) Int. Cl.
| | |
|---|---|
| *A61N 1/04* | (2006.01) |
| *A61N 1/39* | (2006.01) |
| *A61B 5/00* | (2006.01) |
| *A61B 5/282* | (2021.01) |
| *A61B 5/361* | (2021.01) |
| *A61B 5/346* | (2021.01) |
| *A61B 5/363* | (2021.01) |

(52) U.S. Cl.
CPC .............. *A61B 5/361* (2021.01); *A61B 5/346* (2021.01); *A61B 5/6805* (2013.01);
(Continued)

(58) Field of Classification Search
CPC ....... A61B 5/361; A61B 5/316; A61B 5/6805; A61B 5/6831; A61B 5/282; A61B 5/363;
(Continued)

(56) References Cited

U.S. PATENT DOCUMENTS

| | | |
|---|---|---|
| 4,920,969 A | 5/1990 | Suzuki et al. |
| 7,289,844 B2 | 10/2007 | Misczynski et al. |

(Continued)

OTHER PUBLICATIONS

Monebo Remote, Wireless ECG Monitoring Belt Cleared in U.S., https://www.dicardiology.com/content/monebo-remote-wireless-ecg-monitoring-belt-cleared-US, May 15, 2007, 1 page.

(Continued)

*Primary Examiner* — Carl H Layno
*Assistant Examiner* — Anh-Khoa N Dinh
(74) *Attorney, Agent, or Firm* — ZOLL Medical Corporation

(57) ABSTRACT

A cardiac monitoring and treatment system includes a controller, a first wearable portion, and a second wearable portion separate from the first wearable portion. The first wearable portion includes an elongated strap configured to encircle a thoracic region of a patient, a plurality of ECG sensing electrodes disposed about the elongated strap, one or more receiving ports configured to receive one or more additional components including a treatment electrode and/or an additional sensor, and a plurality of conductive wires configured to couple the plurality of ECG sensing electrodes and the one or more receiving ports with the controller. The second wearable portion is configured to be worn over at least one shoulder of the patient and includes a wearable substrate, one or more treatment electrodes disposed on the wearable substrate, and at least one conductive wire configured to releasably connect the one or more treatment electrodes to the controller.

27 Claims, 17 Drawing Sheets

(52) U.S. Cl.
CPC .......... *A61B 5/6831* (2013.01); *A61N 1/0484* (2013.01); *A61N 1/3904* (2017.08); *A61B 5/282* (2021.01); *A61B 5/363* (2021.01); *A61B 5/6823* (2013.01); *A61N 1/046* (2013.01)

(58) Field of Classification Search
CPC .. A61B 5/6823; A61B 5/4836; A61N 1/0484; A61N 1/3904; A61N 1/046; A61M 16/10; A61M 16/00; A61M 2205/3546; A61M 16/06; A61M 2202/0208; A61M 2230/432; A61M 2209/08; A61M 2205/50; A61M 16/0057; A61M 16/0875; A61M 16/20; A61M 16/202; A61M 16/207; A61M 16/208; A61M 16/209; A61M 2016/0015; A61M 2016/0027; A61M 2205/0222; A61M 2205/183; A61M 2205/3337; A61M 2205/8206; A61M 5/142; A61M 1/06; A61M 16/01; A61M 2005/1586; A61M 2021/0016; A61M 2021/0022; A61M 2021/0027; A61M 2021/0044; A61M 2021/0055; A61M 2021/0072; A61M 2021/0077; A61M 21/02; A61M 2205/0272; A61M 2205/04; A61M 2205/3303; A61M 2205/3584; A61M 2205/70; A61M 2209/088; A61M 2230/20; A61M 5/425; A61M 5/427

See application file for complete search history.

(56) References Cited

U.S. PATENT DOCUMENTS

| 8,024,037 | B2 | 9/2011 | Kumar |
| 9,713,445 | B2 | 7/2017 | Freeman et al. |
| 2001/0047140 | A1 | 11/2001 | Freeman |
| 2008/0287770 | A1* | 11/2008 | Kurzweil ................. A61B 5/01 600/388 |
| 2012/0158075 | A1* | 6/2012 | Kaib ..................... A61N 1/046 607/7 |
| 2016/0361533 | A1 | 12/2016 | Savage et al. |
| 2017/0143977 | A1 | 5/2017 | Kaib et al. |
| 2017/0157416 | A1 | 6/2017 | Medema et al. |
| 2017/0216613 | A1 | 8/2017 | Kaib et al. |
| 2019/0143131 | A1 | 5/2019 | Webster et al. |

OTHER PUBLICATIONS

Qardiocore, Wearable EKG ECG Monitor, https://store.getquardio.com/products/qardiocore, Mar. 20, 2019, 14 pages.

Monebo Technologies, Inc., CardioBelt ECG Acquisition System, 2010, 1 page.

Monebo Technologies, Inc., CardioBelt ECG Acquisition System, Apr. 2008, 2 pages.

Coxworth, Ben, Smart fibers change color to show bandage pressure, https://newatlas.com/author/ben-coxworth/, May 29, 2018, 2 pages.

Monebo Technologies, Inc., Remote ECG Monitoring, Apr. 2008, 2 pages.

Song, Hwa Kyung, Categorization of Women's Lower Body Shapes Using Multi-View 3D Body Scan Measurements, and Development of Shape-Driven Automated Custom Patterns, (A Dissertation Presented to the Faculty of the Graduate School of Cornell University In Partial Fulfillment of the Requirements for the Degree of Doctor of Philosophy), Jan. 2011, 234 pages.

SME Medical Point-Of-Care (white paper), Physicians as Manufacturers: The Rise of Point-of-care Manufacturing, 20 pages.

Sawh, Michael @michaelsawh, ECG explained: The science behind the new wearable health tech revolution, https://www.wareable.com/health-and-wellbeing/ecg-heart-rate-monitor-watch-guide-6508, Sep. 12, 2018, 5 pages.

* cited by examiner

MODULAR GARMENT FOR A WEARABLE MEDICAL DEVICE

CROSS REFERENCE TO RELATED APPLICATIONS

This application is a divisional of U.S. patent application Ser. No. 16/455,823, filed Jun. 28, 2019, entitled "Modular Garment for a Wearable Medical Device," now U.S. Pat. No. 11,412,973, which is hereby incorporated by reference in its entirety.

BACKGROUND

The present disclosure is directed to wearable medical devices, for example wearable monitoring devices and wearable monitoring and treatment devices.

A wide variety of electronic and mechanical devices monitor and treat medical conditions. In some examples, depending on the underlying medical condition being monitored or treated, medical devices such as cardiac monitors or defibrillators may be surgically implanted or externally connected to a patient. In some cases, physicians may use medical devices alone or in combination with drug therapies to treat conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before medical assistance can arrive. Other cardiac arrhythmias can include excessively slow heart rates known as bradycardia or excessively fast heart rates known as tachycardia. Cardiac arrest can occur when the heart experiences various arrhythmias that result in the heart providing insufficient levels of blood flow to the brain and other vital organs for the support of life. Such arrhythmias include, for example, ventricular fibrillation, ventricular tachycardia, pulseless electrical activity (PEA), and asystole (heart stops all electrical activity).

Cardiac arrest and other cardiac health ailments are a major cause of death worldwide. Various resuscitation efforts aim to maintain the body's circulatory and respiratory systems during cardiac arrest in an attempt to save the life of the patient. Implementing these resuscitation efforts quickly improves the patient's chances of survival. Implantable cardioverter/defibrillators (ICDs) or external defibrillators (such as manual defibrillators or automated external defibrillators (AEDs)) have significantly improved success rates for treating these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

External pacemakers, defibrillators and other medical monitors designed for ambulatory and/or long-term use have further improved the ability to timely detect and treat life-threatening conditions. For example, certain medical devices operate by continuously monitoring the patient's heart through one or more sensing electrodes for treatable arrhythmias and, when such is detected, the device applies corrective electrical pulses directly to the heart through two or more treatment electrodes.

Example cardiac monitoring and treatment devices can include a vest or garment worn by the patient and a monitoring and treatment monitor coupled to electrodes disposed in the vest or garment. These devices are prescribed for continuous wear by the patient for long periods of time. As such, the vest or garment must be optimized for patient comfort and efficacious device operation. Further, patients are generally discouraged from discontinuing use of the device without consulting with their caregivers. Accordingly, the devices are to be worn in compliance with caregiver instructions to ensure maximum protection from adverse events.

SUMMARY

In one example, an ergonomic and unobtrusive cardiac monitoring and treatment device for continuous wear includes a band configured to be worn about a thoracic region of a patient within a T1 thoracic vertebra region and a T12 thoracic vertebra region. The band has a vertical span of between 1 to 15 centimeters along at least 50 percent of a length of the band, the band being configured to be immobilized relative to a skin surface of the thoracic region of the patient by exerting one or more compression forces against the thoracic region. The band includes a plurality of electrodes and associated circuitry disposed about the band. The plurality of electrodes and associated circuitry disposed about the band includes at least one pair of ECG sensing electrodes disposed about the band and an ECG acquisition circuit in communication with the at least one pair of ECG sensing electrodes. The at least one pair of ECG sensing electrodes can be configured to sense an ECG signal of the patient, and the ECG acquisition circuit is configured to provide ECG information for the patient based on the sensed ECG signal. The plurality of electrodes and associated circuitry disposed about the band includes at least one pair of treatment electrodes and a treatment delivery circuit being in communication with the at least one pair of treatment electrodes. The at least one pair of treatment electrodes are configured to deliver an electrotherapy to the patient, a first one of the at least one pair of treatment electrodes being configured to be located within an anterior area of the thoracic region and a second one of the at least one pair of treatment electrodes being configured to be located within a posterior area of the thoracic region of the patient, and the treatment delivery circuit is configured to cause delivery of the electrotherapy to the patient. The band includes one or more sensor ports for receiving one or more physiological sensors separate from the at least one pair of ECG sensing electrodes.

The device includes a controller including an ingress-protected housing, and a processor disposed within the ingress-protected housing. The processor is configured to analyze the ECG information of the patient from the ECG acquisition circuit and detect one or more treatable arrhythmias based on the ECG information, and cause the treatment delivery circuit to deliver the electrotherapy to the patient on detecting the one or more treatable arrhythmias.

Implementations of the device may include one or more of the following features.

In one example, the band is configured to be worn about the thoracic region with in a T5 thoracic vertebra region and a T11 thoracic vertebra region. The band can be configured to be worn about the thoracic region with in a T8 thoracic vertebra region and a T10 thoracic vertebra region.

In an example, the band can be configured to exert the one or more compression forces in a range from 0.025 psi to 0.75 psi. The band can be configured to exert the one or more compression forces in a range from 0.05 psi to 0.70 psi to the thoracic region. The band can be configured to exert the one or more compression forces in a range from 0.075 to 0.675 psi to the thoracic region. The band can be configured to exert the one or more compression forces in a range from 0.1 to 0.65 psi to the thoracic region.

In examples, the band has a vertical span in a range of 2 to about 12 centimeters along at least 50 percent of a length of the band. The band can have a vertical span in a range of 3 to about 8 centimeters along at least 50 percent of a length of the band.

In an example, the device includes a conductive wiring configured to communicatively couple the controller to the plurality of electrodes and associated circuitry disposed about the band.

In examples, the ingress-protected housing includes at least one ingress-protected connector port configured to receive at least one connector of the conductive wiring. In implementations, the at least one ingress-protected connector port has an IP67 rating.

In implementations, the band is continuously worn over an extended period of time.

In examples, the one or more sensor ports are in communication with the processor via a conductive wiring disposed about the band.

In examples, the band is sized to fit about the thoracic region of the patient by matching the length of the band to one or more circumferential measurements of the thoracic region during an initial fitting. In implementations, band proportions and dimensions are derived from patient-specific thoracic 3D scan dimensions such that the band is sized to fit proportions, dimensions, and shape of the thoracic region.

In examples, the compression portion includes an adjustable fastener for securing the band about the thoracic region of the patient within the range of compression forces. In some examples, the compression portion includes an unbroken loop of a stretchable fabric defining the band. In implementations, the band is configured to stretch over the shoulders or hips of the patient and contract when positioned about the thoracic region. The stretchable fabric can include at least one of elastic polyurethane fiber neoprene, spandex, nylon-spandex, nylon-LYCRA, ROICA, LINEL, INVIYA, ELASPAN, ACEPORA, and ESPA. In implementations, the compression portion includes an elasticized thread disposed in the band. In implementations, the compression portion includes an elasticized panel disposed in the band, and the elasticized panel is a portion of the band spanning less than a total length of the band. In implementations, the compression portion includes an adjustable tension element disposed in the band.

In implementations, the band comprises a breathable skin-facing layer having an MVTR of between about 600 g/m$^2$/day and about 1,400 g/m$^2$/day. In implementations, the skin-facing layer includes at least one of a compression padding, a silicone tread, and one or more textured surface contours.

In examples, the device includes an adhesive configured to secure the band to the thoracic region of the patient. In implementations, the adhesive is configured to be removable.

In examples, the band includes at least one visible indicator of band tension disposed on a posterior surface of the band.

In some examples, the band includes at least one of an anterior appendage and a posterior appendage, and at least one of the plurality of electrodes is disposed on the at least one of the anterior appendage and the posterior appendage. In implementations, each of the at least one of the anterior appendage and the posterior appendage is a flap extending vertically along the thoracic region from a circumferential top or bottom edge of the band. In implementations, the at least one of the anterior appendage and the posterior appendage cumulatively occupy 50 percent or less of the length of the band. In implementations, an average vertical rise from a bottom edge of the band to a top edge of each of the at least one of the anterior appendage and the posterior appendage is greater than the average vertical rise of the band.

In one example, a device includes a controller including at least one processor, a first wearable portion, and a second wearable portion separate from the first wearable portion. In examples, the first wearable portion includes an elongated strap configured to encircle a thoracic region of a patient. The elongated strap is configured to be immobilized relative to a skin surface of the thoracic region of the patient by exerting one or more compression forces against the thoracic region. The first wearable portion includes a plurality of ECG sensing electrodes disposed about the elongated strap. The plurality of ECG sensing electrodes are configured to sense an ECG signal of the patient. The first wearable portion includes one or more receiving ports configured to receive one or more additional components including at least one of a treatment electrode and an additional sensor, and the plurality of conductive wires configured to couple the plurality of ECG sensing electrodes and the one or more receiving ports with the controller.

The second wearable portion is configured to be worn over at least one shoulder of the patient. The second wearable portion includes a wearable substrate, and one or more treatment electrodes disposed on the wearable substrate. The one or more treatment electrodes include a corresponding conductive surface configured to contact an anterior area and a posterior area of the thoracic region of the patient. The second wearable portion includes at least one conductive wire configured to releasably connect the one or more treatment electrodes to the controller.

Implementations of the system may include one or more of the following features.

In examples, the elongated strap has a vertical span in a range of 1 to about 15 centimeters along at least 50 percent of a length of the elongated strap. The elongated strap can have a vertical span in a range of 2 to about 12 centimeters along at least 50 percent of a length of the elongated strap. The elongated strap can have a vertical span in a range of 3 to about 8 centimeters along at least 50 percent of a length of the elongated strap.

In examples, the second wearable portion is configured to be worn for a cumulative duration less than or equal to a duration of wear of the first wearable portion.

In some examples, the second wearable portion has a compression force relatively lower than the one or more compression forces of the elongated strap.

In examples the system includes an ECG acquisition circuit in communication with the plurality of ECG sensing electrodes and the at least one processor and configured to provide ECG information for the patient based on the sensed ECG signal. In implementations, the at least one processor is configured to provide a notification to the patient to wear the second wearable portion upon detecting the impending cardiac event. In implementations, the notification includes an instruction to connect the at least one conductive wire of the second wearable portion to the controller. In implementations, the at least one processor provides, via the output device, an indication of successful connection of the at least one conductive wire of the second wearable portion to the controller.

In examples, the at least one processor is configured to initiate delivery of a therapeutic shock via the one or more treatment electrodes.

In examples, the elongated strap exerts the one or more compression forces such that the elongated strap is immobile relative to a skin surface of the thoracic region. In implementations, the elongated strap is configured to exert the one or more compression forces in a range from 0.025 psi to 0.75 psi. In implementations, the elongated strap is configured to exert the one or more compression forces in a range from 0.05 to 0.70 psi to the thoracic region. In implementations, the elongated strap is configured to exert the one or more compression forces in a range from 0.075 to 0.675 psi to the thoracic region. In implementations, the elongated strap is configured to exert the one or more compression forces in a range from 0.1 to 0.65 psi to the thoracic region.

In examples, the elongated strap is sized to fit about the thoracic region. The elongated strap can be sized to fit by matching a length of the elongated strap to one or more circumferential measurements of the thoracic region during an initial patient fitting. Elongated strap dimensions can be derived from a 3D scan of the thoracic region such that the elongated strap is sized to fit proportions, dimensions, and shape of the thoracic region. In implementations, the elongated strap is 3D printed to at least one of body proportions, body shape, body posture, and linear surface measurements of the thoracic region of the patient. In implementations, at least a portion of the elongated strap is 3D-printed to conform the sash to one or more portions of the thoracic region.

In examples, at least one fastener is disposed on a first end of the elongated strap for adjoining a second end of the elongated strap in secured attachment about the thoracic region of the patient. In implementations, the elongated strap includes an adjustable latching mechanism configured to secure the elongated strap about the thoracic region of the patient.

In examples, the second wearable portion can be at least one of a shirt, a vest, a bandeau, a pinnie, a butterfly harness, a yoke, and a dickie. The first and second wearable portions are configured to be worn beneath a clothing of the patient.

In examples, the first wearable portion includes an appendage mechanically attached to the elongated strap. The appendage is configured to be continuously worn about the thoracic region of the patient. In implementations, the appendage includes at least one additional ECG sensing electrode in communication with the plurality of conductive wires of the elongated strap, the at least one additional ECG sensing electrode being configured to sense the ECG signal of the patient in conjunction with the plurality of ECG sensing electrodes of the elongated strap. The appendage comprises at least one treatment electrode in communication with the at least one processor, the at least one treatment electrode configured to provide a therapeutic shock. In implementations, the at least one treatment electrode is in wired communication with the plurality of conductive wires of the elongated strap. In implementations, the appendage is a flap. In implementations, the appendage is an over-the-shoulder sash. In implementations, the appendage is a pair of over-the shoulder sashes crossing over the anterior area of the thoracic region. In implementations, the appendage is configured to be affixed to the elongated strap. In implementations, the appendage is monolithically formed with the elongated strap.

In examples, the elongated strap comprises a breathable skin-facing layer having an MVTR of between about 600 $g/m^2/day$ and about 1,400 $g/m^2/day$.

In one example, an ergonomic and unobtrusive cardiac monitoring and treatment device for continuous wear includes a sash, a plurality of electrodes and associated circuitry disposed about the sash, and a controller. The sash is configured to be worn over a shoulder of a patient, encircling a thoracic region of the patient, extending from over a first shoulder of the patient across an anterior area of the thoracic region to an opposite lateral side of the thoracic region under a second shoulder of the patient adjacent to the axilla and further extending across a posterior area of the thoracic region from under the second shoulder to over the first shoulder. The plurality of electrodes and associated circuitry disposed about the sash include at least one pair of ECG sensing electrodes disposed about the sash, an ECG acquisition circuit in communication with the at least one pair of ECG sensing electrodes, and at least one pair of treatment electrodes coupled to a treatment delivery circuit.

The at least one pair of ECG sensing electrodes disposed about the sash are configured to sense an ECG signal of the patient, and the ECG acquisition circuit in communication with the at least one pair of ECG sensing electrodes is configured to provide ECG information of the patient based on the sensed ECG signal. The at least one pair of treatment electrodes coupled to the treatment delivery circuit is configured to deliver an electrotherapy to the patient. A first one of the at least one pair of treatment electrodes is configured to be located within the anterior area of the thoracic region and a second one of the at least one pair of treatment electrodes is configured to be located within the posterior area of the thoracic region of the patient. The treatment delivery circuit in communication with the at least one pair of treatment electrodes is configured to cause delivery of the electrotherapy to the patient.

The controller includes an ingress-protected housing, and a processor disposed within the ingress-protected housing. The processor is configured to analyze the ECG information of the patient from the ECG acquisition circuit and detect one or more treatable arrhythmias based on the ECG information, and cause the treatment delivery circuit to deliver the electrotherapy to the patient on detecting the one or more treatable arrhythmias.

Implementations of the device may include one or more of the following features.

In examples, the sash is sized to fit the thoracic region. In implementations, sized to fit comprises determining dimensions of the thoracic region in an initial fitting. In implementations, sash proportions and dimensions are derived from a 3D scan of the thoracic region such that the sash is sized to fit proportions, dimensions, and shape of the thoracic region.

In examples, the sash is 3D printed to at least one of body proportions, body shape, body posture, and linear surface measurements of the thoracic region of the patient. In implementations, at least a portion of the sash is 3D-printed to conform the sash to one or more portions of the thoracic region.

In examples, the sash is configured to be immobilized relative to a skin surface of the thoracic region of the patient by exerting one or more compression forces against the thoracic region. In implementations, the sash is configured to exert the one or more compression forces in a range from 0.025 psi to 0.75 psi. In implementations, the sash is configured to exert the one or more compression forces in a range from 0.05 psi to 0.70 psi to the thoracic region. In implementations, the sash is configured to exert the one or more compression forces in a range from 0.075 to 0.675 psi to the thoracic region. In implementations, the sash is configured to exert the one or more compression forces in a range from 0.1 to 0.65 psi to the thoracic region.

In implementations, the device includes an adhesive configured to secure the sash to the thoracic region of the patient such that the sash is immobile relative to a skin surface of the thoracic region. The adhesive can be replaceable.

In implementations, the device includes a plurality of conductive wires configured to communicatively couple the controller to the plurality of electrodes and associated circuitry disposed about the sash.

DETAILED DESCRIPTION

Figure 1:
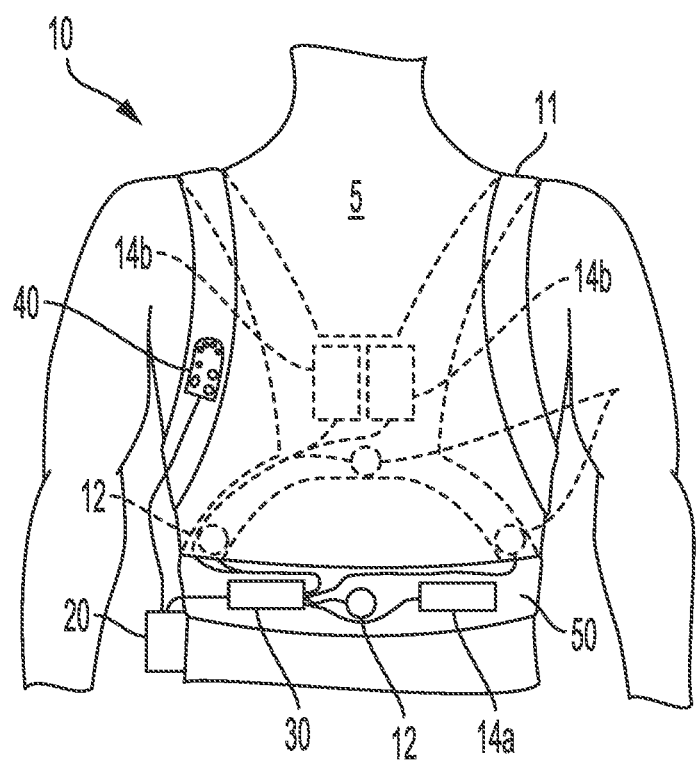
FIG. 1 depicts an embodiment of a patient-worn medical device.

This disclosure relates to various improvements in one or more features, implementations, and design configurations of wearable cardiac monitoring and/or treatment devices over conventional devices. Patients prescribed with such life critical devices need to be able to wear them continuously through daily activities to ensure near constant protection against life-threatening cardiac arrhythmia conditions over extended periods of time. Accordingly, the devices herein provide improved ergonomics and physiological benefits that promote better voluntary compliance with device use guidelines than conventional devices. One set of examples herein is based on a wearable defibrillator band or strap that is worn unobtrusively and comfortably under the patient's undergarments. Another set of examples feature at least two separate wearables portions that can also be worn unobtrusively and comfortably. A first wearable portion includes ECG sensing electrodes and/or other physiological sensors. Additionally, a second wearable portion is optionally separable from the first wearable portion and includes treatment electrodes.

Briefly, the wearable defibrillator band is worn about a thoracic region of a patient, in particular, within a T1 thoracic vertebra region and a T12 thoracic vertebra region. The band includes certain light weight elements such as electrocardiogram (ECG) sensors and treatment electrodes in close proximity or in direct contact with the patient's skin, as well as associated circuitry necessary for the device to acquire and process the ECG signals. To secure the sensors and electrodes in close proximity or in direct contact with the patient's skin, the band includes a compression portion that immobilizes the band relative to the patient's skin as the patient moves and goes about a daily routine. The circuitry in the band is electrically coupled to a controller housed within an ingress-protected housing, which includes heavier energy storage elements such as capacitors and batteries.

Because no portion of the band traverses the patient's limbs or shoulders, the patient is free to move, bend, twist and lift his or her arms and/or shoulders without imparting torque on the device 100. This immobilizes the band relative to the patient's skin and prevents or eliminates signal noise associated with sensors shifting against the skin when compared to wearable devices that run over a patient's shoulder or arm. The size and position of the band also provides a discreet and comfortable device covering only a relatively small portion of the surface area of a patient's entire thoracic region and accommodating a plurality of body types. A relatively small portion can be for example, 25%, or less (e.g. 20%, 15%, 10%, 5% or less than 5%) of the surface area of the thoracic region 105. Covering only a relatively small portion of the thoracic region further improves comfort and encourages patient compliance because the patient will feel little or no discomfort and may forget the band is being worn.

These features as well as others described herein thus provide certain advantages over conventional wearable defibrillators at least in terms of comfort, patient compliance, and minimizing false arrhythmia alerts.

Turning to the two separable wearable portions embodiment, disclosed herein is a first wearable portion that includes an elongated strap configured to encircle a thoracic region of a patient and exert a radial compression force to secure the strap on the patient. The strap includes the ECG sensing electrodes as well as one or more receiving portions to receive additional components including treatment electrodes and additional sensors (e.g., non-ECG physiological sensors or motion sensors). The second wearable portion is configured to be worn over at least one shoulder of the patient and includes a wearable substrate on which one or more treatment electrodes is disposed. In examples, the second wearable portion includes treatment electrodes, and the ECG sensing electrodes in the first wearable portion as well as the treatment electrodes in the second wearable portion are together electrically coupled to a controller housed within an ingress-protected housing including the capacitors and batteries. In certain implementations, the second wearable portion is implemented to fully support the device capacitors and batteries, e.g., wherein such capacitors and batteries are evenly weight distributed within the second wearable portion. The second wearable portion can be worn optionally and for a shorter duration than the first wearable portion such that a patient can avoid wearing treatment portions of the device during uneventful monitoring periods. The second wearable portion can be worn, for example, only when a patient is deemed at potential risk for a sudden cardiac event occurring within some period of time (e.g. 1 day, 1 week, 2 weeks). The treatment electrodes of the second wearable portion are configured to couple to wiring of the first wearable portion and/or a receiving port disposed on the housing that is in electrical communication with a processor of the controller.

Wearable medical devices as disclosed herein include cardiac monitoring and/or treatment devices that monitor electrocardiogram (ECG) signals and, in certain examples, other physiological signals of patients wearing such devices. For example, the medical device can be used as a cardiac monitor in certain cardiac monitoring applications, including heart failure and arrhythmia monitoring applications. In some implementations, the medical device can be configured to monitor other physiological parameters as an alternative or in addition to ECG signals and/or metrics. In addition to or instead of cardiac monitoring, such devices may also monitor respiratory parameters (e.g., to monitor congestion, lung fluid status, apnea, etc.), patient activity (e.g., posture, gait, sleep conditions, etc.) and other physiological conditions. In some implementations, the medical device can be configured to include one or more treatment components interoperable with and, in embodiments, selectively connected to one or more monitoring components.

In some implementations, a patient-worn cardiac monitoring and treatment device detects one or more treatable arrhythmias based on physiological signals from a patient. The treatable arrhythmias include those that may be treated by defibrillation pulses, such as ventricular fibrillation (VF) and shockable ventricular tachycardia (VT), or by pacing pulses, such as bradycardia, tachycardia, and asystole. A wearable medical device as disclosed herein monitors a patient's physiological conditions, e.g., cardiac signals, respiratory parameters, and patient activity, and delivers potentially life-saving treatment to the patient. The medical device can include a plurality of sensing electrodes that are disposed at various locations on the patient's body and configured to monitor the cardiac signals of the patient such as electrocardiogram (ECG) signals. In some implementations, the device can also be configured to allow a patient to report his/her symptoms including one or more skipped beat(s), shortness of breath, light headedness, racing heart, fatigue, fainting, and chest discomfort. The device determines an appropriate treatment for the patient based on the detected cardiac signals and/or other physiological parameters prior to delivering a therapy to the patient. The device can then cause one or more therapeutic shocks, for example, defibrillating and/or pacing shocks, to be delivered to the body of the patient. The wearable medical device includes a plurality of treatment electrodes disposed on the patient's body and configured to deliver the therapeutic shocks.

As described in U.S. Pat. No. 8,983,597, titled "MEDICAL MONITORING AND TREATMENT DEVICE WITH EXTERNAL PACING," issued on Mar. 17, 2015 (hereinafter the "'597 patent"), which is hereby incorporated herein by reference in its entirety, an example patient worn cardiac monitoring and treatment device can be, for example, an ambulatory medical device that is capable of and designed for moving with the patient as the patient goes about his or her daily routine. For example, as shown in FIG. 1, the ambulatory medical device 10 can be a wearable cardioverter defibrillator (WCD) and can include one or more of the following: a garment 11, one or more physiological sensors 12 (e.g., ECG electrodes, heart rate sensors, vibrational sensors, and/or other physiological sensors), one or more treatment electrodes 14a and 14b (collectively referred to herein as treatment electrodes 14), a medical device controller 20, a connection pod 30, a patient interface pod 40, a belt 50 about the patient's torso to support one or more components, or any combination of these. In some examples, at least some of the components of the medical device 10 can be configured to be affixed to the garment 11 (or in some examples, permanently integrated into the garment 11), which can be worn about the patient's torso 5.

The medical device controller 20 can be operatively coupled to the physiological sensors 12 which can be affixed to the garment 11, e.g., assembled into the garment 11 or removably attached to the garment 11, e.g., using hook and loop fasteners. In some implementations, the physiological sensors 12 can be permanently integrated into the garment 11. The medical device controller 20 can be operatively coupled to the treatment electrodes 14. For example, the treatment electrodes 14 can also be assembled into the garment 11, or, in some implementations, the treatment electrodes 14 can be permanently integrated into the garment 11.

In embodiments according to this disclosure, such as that of FIGS. 2A-6B and 9A-14, one or more portions of the garment 11 of the device 10 of FIG. 1 can be eliminated or distributed about separately donned wearable portions. In embodiments, permanently or temporarily eliminating one or more portions of the garment 11 results in leaving a device configured with relatively less surface area. Such a wearable device can include one or more of, for example, a belt, a harness, a bandeau, a sash, a vest, a yoke, and/or a pinnie. In implementations, the device can be fitted to the body as a lightweight stretchable support garment.

Systems and techniques are disclosed herein to improve ergonomics of the one or more wearable portions of such a wearable medical device. Patients are encouraged to comply with the device use guidelines, including wearing the device at all times including while showering or sleeping. To improve patient compliance with these guidelines, the devices described herein include one or more wearable portions that are lightweight, comfortable, and discreet so that they may be worn under the patient's clothing. In some implementations described herein, the devices include various features that promote comfort and efficacy while continuing to protect the patient from adverse cardiac events. In implementations, the devices are fitted to nest with the contours of a patient's body, including, for example, the shoulder-neck region and/or the thoracic region. In implementations described herein, the devices include one or more wearable portions configured to be worn continuously and/or selectively, each of the one or more wearable portions configured to support one or more monitoring and/or treatment components. Based on an analysis of monitored signals and output from a predictive algorithm configured to determine the likelihood of a cardiac event, the device can instruct the patient on when to add additional monitoring and/or treatment components to the one or more wearable portions, and/or when to add an additional one or more wearable portions including one or more monitoring and/or treatment components. In modular implementations of the wearable medical device including two or more interoperable wearable portions, each portion can include one or more of the aforementioned monitoring and treatment components.

In an example scenario, a patient may be prescribed the wearable medical device following a medical appointment. For example, the such a wearable monitoring and/or treatment device can be prescribed for patients that meet certain criteria. Examples may include or more of the following criteria: (1) Primary prevention (ejection fraction (EF)≤35% and Myocardial Infarction (MI), nonischemic cardiomyopathy (NICM), or other dilated cardiomyopathy (DCM)), including after recent MI (e.g., typically worn for about 40 days ICD waiting period), before and after coronary artery bypass grafting (CABG) or percutaneous transluminal coronary angioplasty (PTCA) (e.g., typically worn for about 90 day ICD waiting period), while listed for cardiac transplant, when recently diagnosed with nonischemic cardiomyopathy (e.g., typically worn for about 3 to 9 month ICD waiting period), when diagnosed with New York Heart Association (NYHA) class IV heart failure, and when diagnosed with terminal disease with life expectancy of less than 1 year; (2) ICD indications when patient condition delays or prohibits ICD implantation; and (3) ICD explantation.

Wearing the device protects the patient from life-threatening arrhythmias, while also enabling the collection of diagnostic information for additional, potentially more invasive procedures. The example devices described herein are prescribed to be worn continuously and typically for a prescribed duration of time. For example, the prescribed duration can be a duration for which a patient is instructed by a caregiver to wear the device in compliance with device use instructions. The prescribed duration may be for a short period of time until a follow up medical appointment (e.g., 1 hour to about 24 hours, 1 day to about 14 days, or 14 days to about one month), or a longer period of time (e.g., 1 month to about 3 months) during which diagnostics information about the patient is being collected even as the patient is being protected against cardiac arrhythmias. The prescribed use can be uninterrupted until a physician or other caregiver provides a specific prescription to the patient to stop using the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for an extended period of at least one year.

Because these devices require continuous operation and wear by patients to which they are prescribed, advantages of the implementations herein include use of comfortable, non-irritating, biocompatible construction materials, and features designed to enhance patient compliance. Such compliance-inducing design features include, for example, device ergonomics and inconspicuous appearance when worn under output garments, among others.

In some implementations, the device includes monitoring and treatment components disposed in or on a cross-body, shoulder-to-hip sash or in or on a monolithic band configured to encircle a thoracic region. The device can be held in compression against the thoracic region so as to minimize or eliminate sensor signal noise and other artifacts. In implementations, the device includes a first wearable portion configured to be worn about the thoracic region for monitoring the patient and one or more ports disposed on the first wearable portion and coupled to a data bus. The one or more ports are configured to receive additional monitoring and/or treatment components for selectively adding functionality to the device. In implementations, the device includes a first wearable portion configured to be worn about the thoracic region for monitoring the patient, and a second, later-added portion. The second wearable portion can be configured to connect to the monitoring components and provide therapeutic treatment to the patient upon detection of a treatable condition. Splitting the components over one or more garments ensures that larger, heavier, and/or infrequently used components, such as defibrillation treatment electrodes, are worn by the patient only when necessary. This distribution of the components of the device over two or more wearable portions lessens patient discomfort throughout a prescribed duration of wear and encourages patient compliance with caregiver instructions.

The devices described here can be prescribed to be worn continuously and for long durations of time, often over the course of several weeks or months. Substantially continuous or nearly continuous use as described herein may nonetheless qualify as continuous use. In some implementations, the patient may remove the wearable medical device for a short portion of the day (e.g., for half an hour while bathing).

At least a monitoring potion of the wearable medical device can be continuously or nearly continuously worn by the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted previously, the wearable medical device can be configured to monitor other physiologic parameters of the patient in addition to cardiac related parameters. For example, the wearable medical device can be configured to monitor, for example, pulmonary vibrations (e.g., using microphones and/or accelerometers), breath vibrations, sleep related parameters (e.g., snoring, sleep apnea), and tissue fluids (e.g., using radio-frequency transmitters and sensors), among others.

Figure 2A:
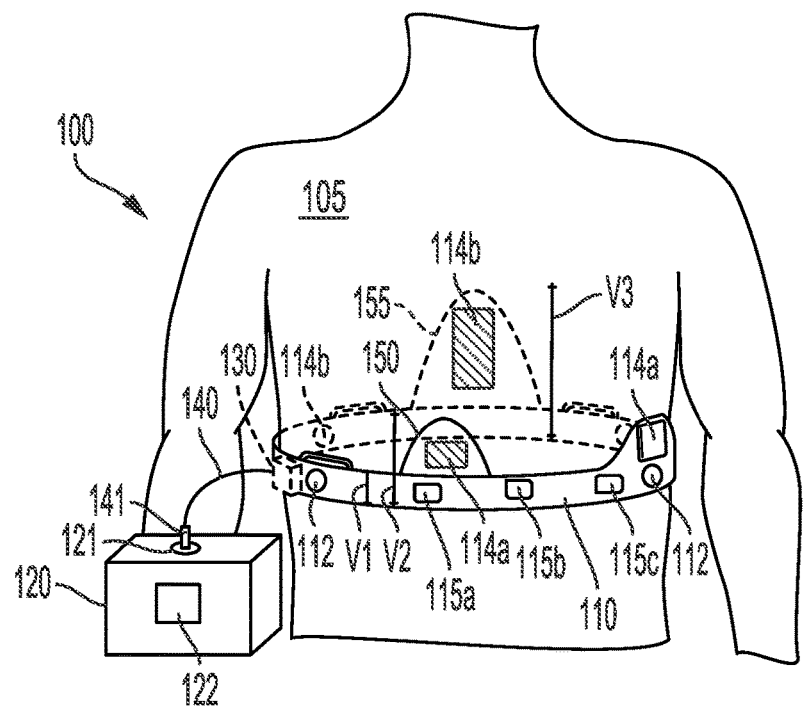
FIG. 2A depicts an embodiment of a patient-worn cardiac monitoring and treatment device comprising band.
Figure 2B:
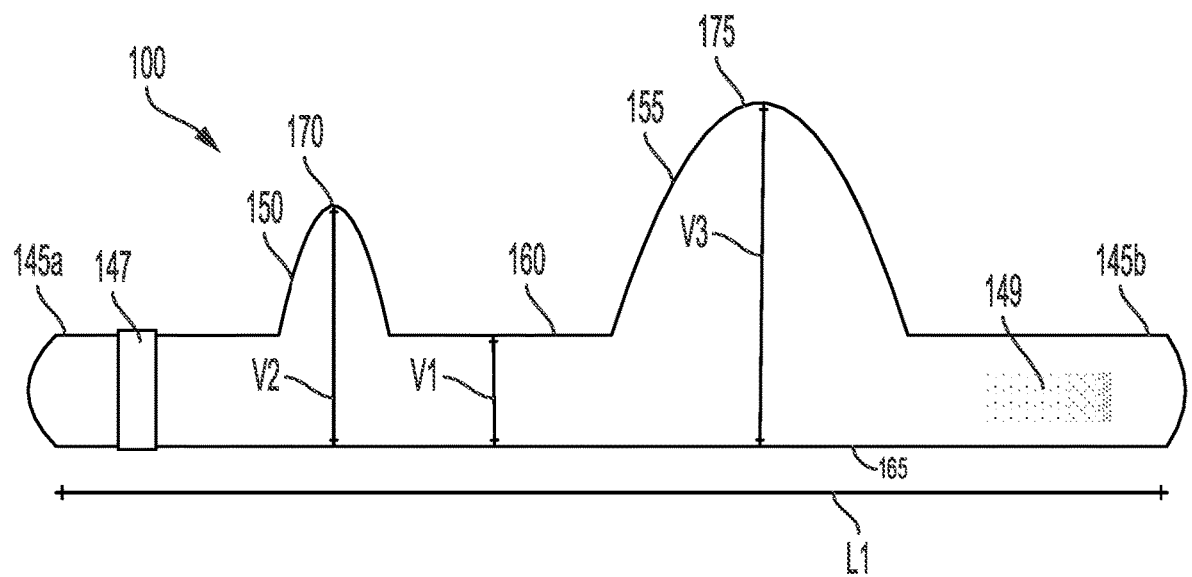
FIG. 2B depicts a schematic of the band of FIG. 2A.

FIGS. 2A-B illustrate an example cardiac monitoring and treatment device 100 that is external, ambulatory, and wearable by a patient. The device 100 is an external or non-invasive medical device, which, for example, is located external to the body of the patient and configured to provide transcutaneous therapy to the body. The device 100 is an ambulatory medical device, which, for example, is capable of and designed for moving with the patient as the patient goes about his or her daily routine.

Figure 3:
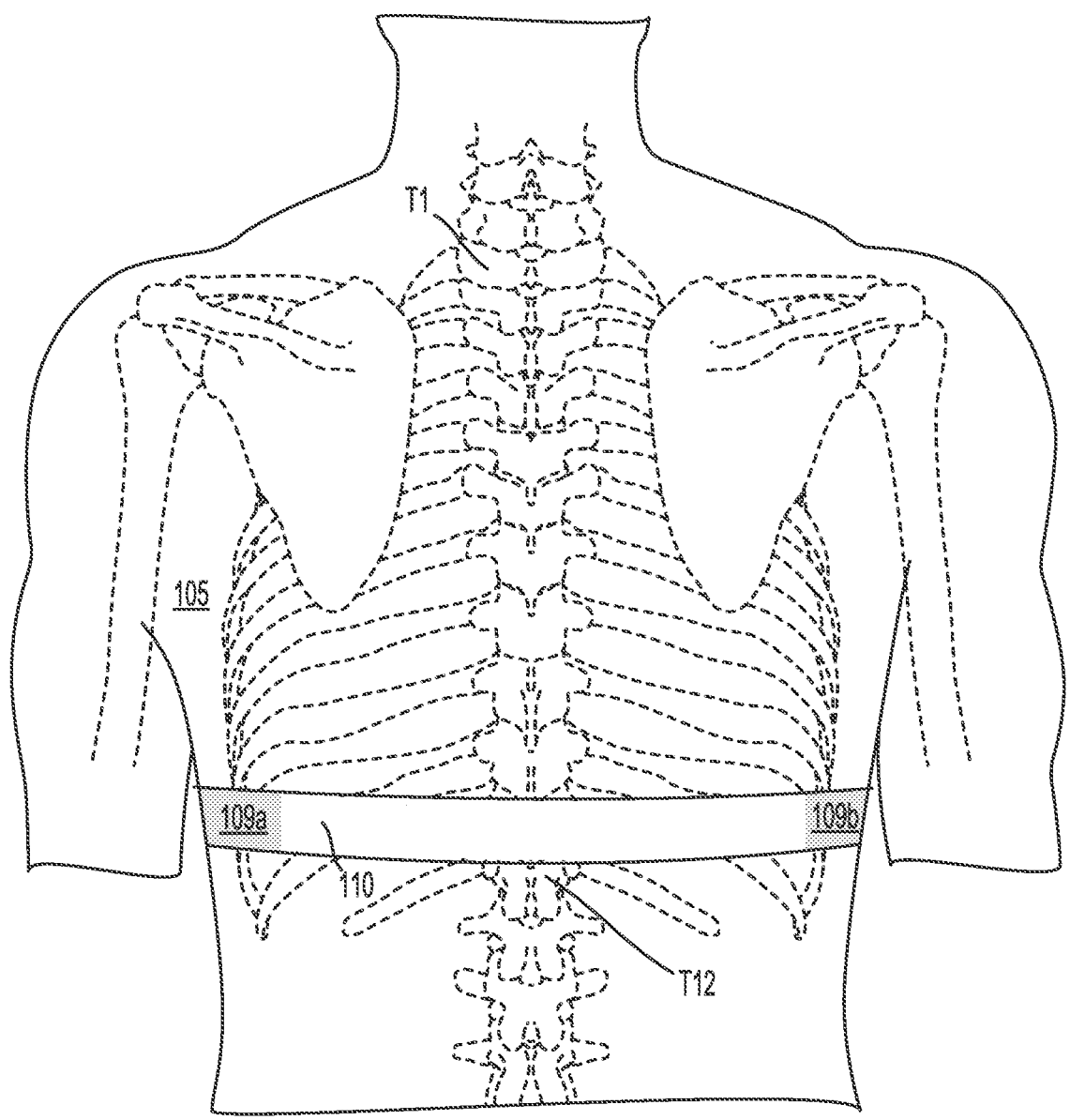
FIG. 3 depicts an embodiment of a patient-worn cardiac monitoring and treatment device relative to a posterior depiction of a patient's skeletal anatomy.
Figure 4:
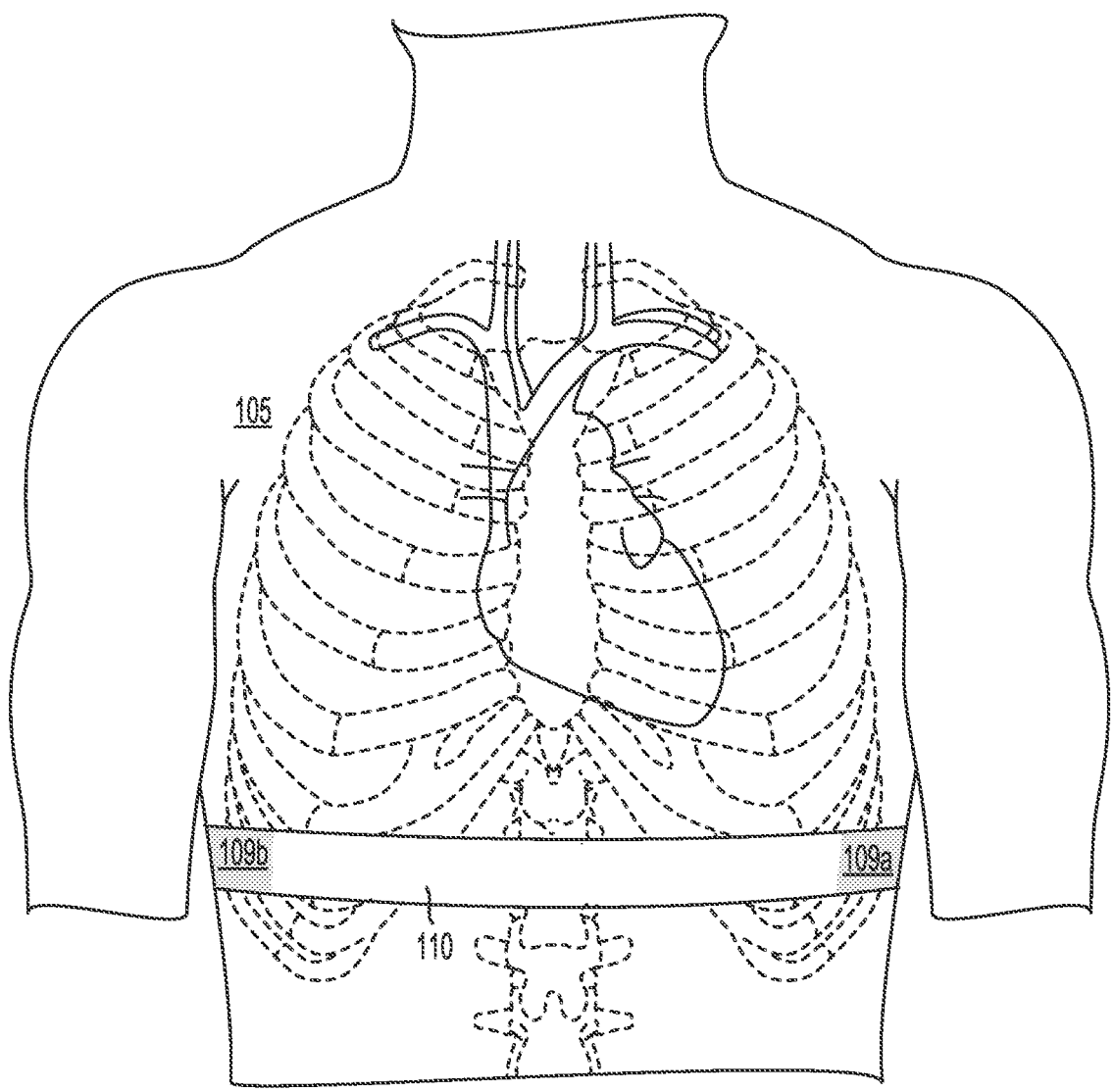
FIG. 4 depicts an embodiment of a patient-worn cardiac monitoring and treatment device relative to an anterior depiction of a patient's skeletal anatomy.
Figure 5:
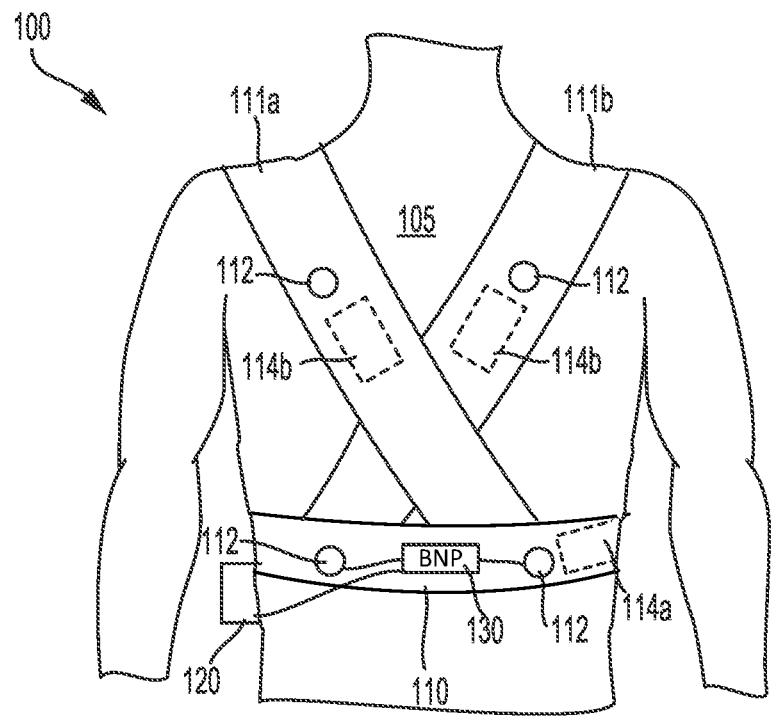
FIG. 5 depicts an embodiment of a patient-worn cardiac monitoring and treatment device comprising band and cross-shoulder appendages.

The device 100 can include a band 110 configured to be worn about a thoracic region 105 of a patient within a T1 thoracic vertebra region and a T12 thoracic vertebra region, as depicted in FIGS. 3 and 4. For example, the device 100 can include a band 110 configured to be worn within a T5 thoracic vertebra region and a T11 thoracic vertebra region. For example, the device 100 can include a band 110 configured to be worn within a T8 thoracic vertebra region and a T10 thoracic vertebra region. As shown in FIG. 2B, the band 110 can have a vertical span V1, of between about 1 to about 15 centimeters along at least 50 percent of a length L1 of the band 110. For example, in implementations, the vertical span V1 is between 2 to 12 centimeters along at least 50 percent of the length L1. For example, in implementations, the vertical span V1 is between 3 to 8 centimeters along at least 50 percent of the length L1. In implementations, the band 110 includes a compression portion disposed in the band 110. In implementations, the band 110 exerts compression forces against the skin of the patient by one or more of manufacturing all or a portion of the band 110 from a compression fabric, proving one or more tensioning mechanisms in and/or on the band 110, and providing a cinching closure mechanism for securing and compressing the band 110 about the thoracic region 105. The compression portion is configured to immobilize the band 110 relative to a skin surface of the thoracic region 105 of the patient by exerting one or more compression forces against the thoracic region. In implementations, the band is configured to exert the one or more compression forces in a range from 0.025 to 0.75 psi to the thoracic region 105. For example, the one or more compression forces can be in a range from 0.05 psi to 0.70 psi, 0.075 psi to 0.675 psi, or 0.1 to 0.65 psi.

Compression forces of the medical device can be determined, for example, using one or more pressure sensors distributed about the band 110 and disposed between the band 110 and the thoracic region 105. The one or more pressure sensors can be, for example, one or more force sensitive resistors, one or more Polydimethylsiloxane (PDMS)-based flexible resistive strain sensors, one or more capacitive pressure sensors, and/or a tactile array of sensors such as those sold by PPS of Los Angeles, CA The one or more pressure sensors can be, for example, ultra-thin (e.g. 0.1 mm or less), flexible pressure sensors. In implementations, the ultra-thin, flexible pressure sensors can be configured to provide pressure mapping using a system for example such as a TEKSCAN measurement and mapping system, including the I-SCAN system by Tekscan, Inc. of South Boston, Mass. In other implementations, the compression forces of the medical device can be modeled using a fabric-based analytical module employing tensile data. In other implementations, the compression forces can be measured using a mechanical measurement system such as the Hohenstein Measurement System, such as the HOSYCAN, manufactured by Hohenstein, Bonnigheim, Germany.

In implementations, compliance with one or more compression forces of embodiments described herein can be determined in accordance with the following test fixtures and conditions. The device 100 can be mounted on a mannequin such as for example, one manufactured by Alvanon. In an example, the mannequin has thoracic circumferential dimensions ranging from 66 cm to 142 cm. In some examples, the garment may be fit on patients such that a garment extends to approximately 1" below the underbust for fitting the patient. One or more of the exemplary sensors previously described can be inserted between the mounted device 100 and the mannequin (or patient) at a plurality of arbitrary locations, for example, 5 locations spaced apart along the circumference of the band 110. In some examples, the locations may be chosen to be at both anterior and posterior positions about the thoracic region of the mannequin (or patient). Compression forces can then be measured and individually compared to the one or more compression ranges described herein. Alternatively, or in addition, the one or more measured compression forces can be averaged and the average force compared to the one or more compression ranges described herein. The test can be conducted under temperature and humidity conditions of 0-60 degrees Celsius and 10-90% humidity. Further, the test can be conducted in a wet environment (e.g., the device mounted on the mannequin or patient is exposed to water) to simulate bathing and/or showering conditions.

As shown in FIG. 2A, the device 100 includes a plurality of electrodes and associated circuitry disposed about the band 110. The plurality of electrodes can include at least one pair of sensing electrodes 112 disposed about the band 110 and configured to be in electrical contact with the patient. The sensing electrodes 112 can be configured to detect one or more cardiac signals such as ECG signals. Example ECG sensing electrodes 112 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference. The device 100 can include an ECG acquisition circuit in communication with the at least one pair of ECG sensing electrodes 112 and configured to provide ECG information for the patient based on the sensed ECG signal. In implementations, the at least one pair of ECG sensing electrodes 112 can include a driven ground electrode, or right leg drive electrode, configured to ground the patient and reduce noise in the sensed ECG signal.

The plurality of electrodes can include at least one pair of treatment electrodes 114a and 114b (collectively referred to herein as treatment electrodes 114) and an associated treatment delivery circuit configured to cause delivery of the electrotherapy to the patient. The at least one pair of treatment electrodes 114 can be configured to deliver an electrotherapy to the patient. For example, one or more of the at least one pair of treatment electrodes 114 can be configured to deliver one or more therapeutic defibrillating shocks to the body (e.g., the thoracic region 105) of the patient when the medical device 100 determines that such treatment is warranted based on the signals detected by the sensing electrodes 112 and processed by the medical device controller 120. Example treatment electrodes 114 include, for example, conductive metal electrodes such as stainless steel electrodes that include, in certain implementations, one or more conductive gel deployment devices configured to deliver conductive gel to the metal electrode prior to delivery of a therapeutic shock. In implementations, a first one of the at least one pair of treatment electrodes 114a is configured to be located within an anterior area of the thoracic region 105 and a second one of the at least one pair of treatment electrodes 114b is configured to be located within a posterior area of the thoracic region 105 of the patient. In some implementations, the anterior area can include a side area of the thoracic region.

In some examples, at least some of the plurality of electrodes and associated circuitry of the device 100 can be configured to be selectively affixed or attached to the band 110 which can be worn about the patient's thoracic region 105. In some examples, at least some of the plurality of electrodes and associated circuitry of the device 100 can be configured to be permanently secured into the band 110. In implementations, the plurality of electrodes are manufactured as integral components of the band 110. For example, the at least one pair of treatment electrodes 114 and/or the at least one pair of ECG sensing electrodes can be formed of the warp and weft of a fabric forming at least a layer of the band 110. In implementations, the treatment electrode 114 and the ECG sensing electrodes 112 are formed from conductive fibers that are interwoven with non-conductive fibers of the fabric. Additional implementations of sensing electrode arrangements and treatment electrode arrangements on a patient-worn medical device are provided herein in subsequent sections.

In implementations, the device 100 can include one or more sensor ports 115a-c (collectively referred to as 115) for receiving one or more physiological sensors separate from the at least one pair of ECG sensing electrodes. The one or more physiological sensors can be, for example, sensors for detecting one or more of pulmonary vibrations (e.g., using microphones and/or accelerometers), breath vibrations, sleep related parameters (e.g., snoring, sleep apnea), and tissue fluids (e.g., using radio-frequency transmitters and sensors). The additional sensor can be, for example, one or more physiological sensors including a pressure sensor for sensing compression forces of the garment, SpO2 sensors, blood pressure sensors, bioimpedance sensors, humidity sensors, temperature sensors, and photoplethysmography sensors. In some examples, the sensor ports 115a-c can also be configured to receive one or more motion and/or position sensors. For example, such motion sensors can include accelerometers for monitoring the movement of the patient's torso in x-, y- and z-axes to determine a movement of the patient, gait, and/or whether the patient is upright, standing, sitting, lying down, and/or elevated in bed with pillows. In certain implementations, one or more gyroscopes may also be provided to monitor an orientation of the patient's torso in space to provide information on, e.g., whether the patient is lying face down or face up, or a direction in which the patient is facing.

Figure 7:
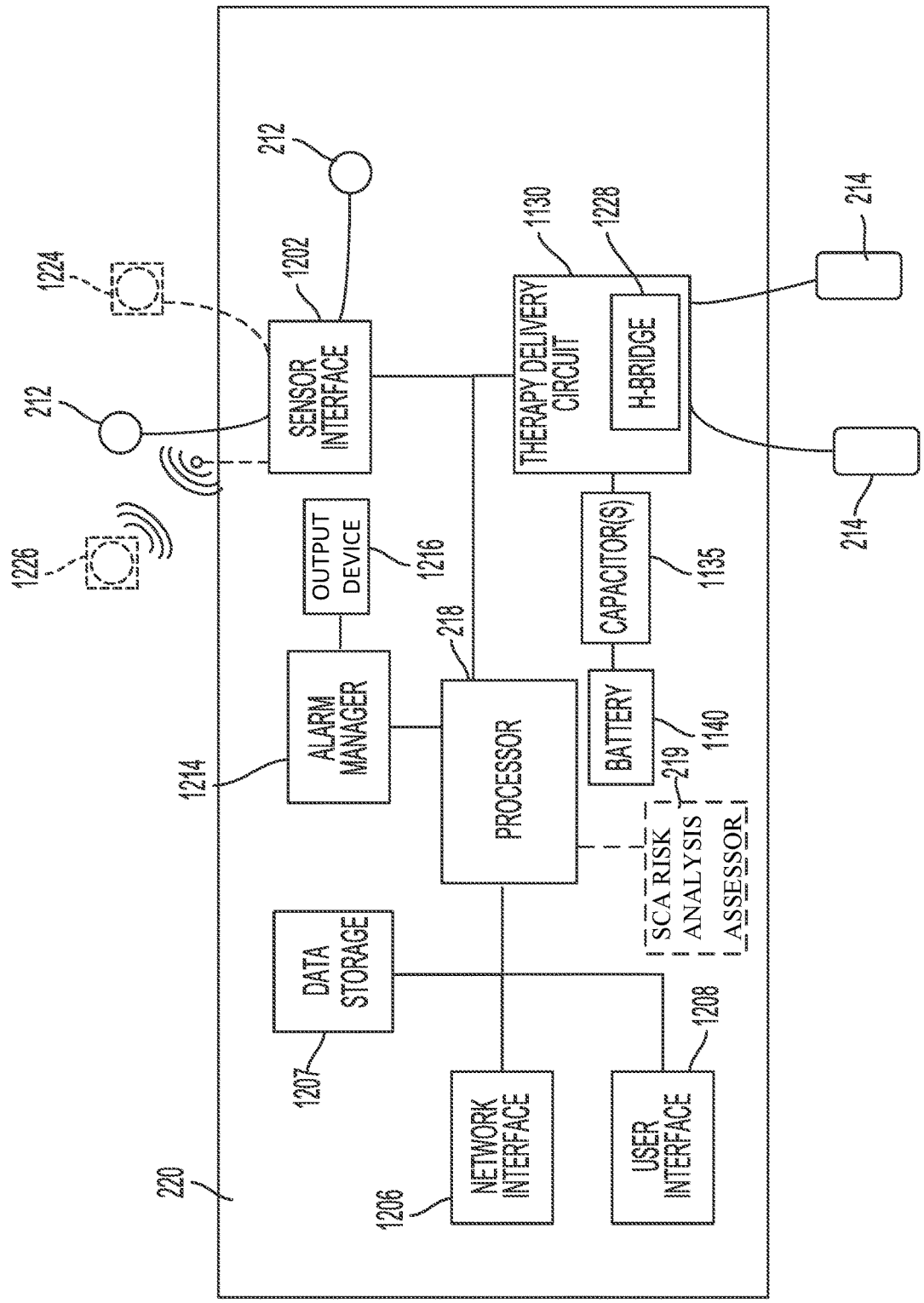
FIG. 7 depicts a schematic diagram of an embodiment of a controller of a patient-worn cardiac monitoring and treatment system.

In implementations, the device 100 includes a controller 120 including an ingress-protected housing, and a processor disposed within the ingress-protected housing. In implementations, as shown in FIG. 7, the controller 120 can include a processor 218, a therapy delivery circuit 1130 including a polarity switching component such as an H-bridge 1128, a data storage 1207, a network interface 1206, a user interface 1208, at least one battery 1140, a sensor interface 1202 that includes, for example, an ECG data acquisition and conditioning circuit, an alarm manager 1214, one or more capacitors 1135, and a Sudden Cardiac Arrhythmia (SCA) Risk Analysis Assessor 219.

The processor 218 is configured to analyze the ECG information of the patient from the ECG acquisition circuit and detect one or more treatable arrhythmias based on the ECG information and cause the treatment delivery circuit to deliver the electrotherapy to the patient on detecting the one or more treatable arrhythmias. The medical device controller 120 can be operatively coupled to the sensing electrodes 112, which can be affixed to the band 110. In embodiments, the sensing electrodes 112 are assembled into the band 110 or removably attached to the garment, using, for example, hook and loop fasteners, thermoform press fit receptacles, snaps, and magnets, among other restraints. In some implementations, as described previously, the sensing electrodes 112 can be a permanent portion of the band 110. The medical device controller 120 also can be operatively coupled to the treatment electrodes 114. For example, the treatment electrodes 114 can also be assembled into the band 110, or, as described previously, in some implementations, the treatment electrodes 114 can be a permanent portion of the band 110. Optionally, the device 100 can includes a connection pod 130 in wired connection with one or more of the plurality of electrodes and associated circuitry. In some examples, the connection pod 130 includes at least one of the ECG acquisition circuit and a signal processor configured to amplify, filter, and digitize the cardiac signals prior to transmitting the cardiac signals to the medical device controller 120. In implementations, the device 100 can include at least one ECG sensing electrode 112 configured to be coupled to the upper portion of the thoracic region 105, above the band 110, the at least one ECG sensing electrode 112 being in wired communication with the ECG acquisition circuitry and at least one of the connection pod and the controller 120.

In implementations, the device includes a conductive wiring 140 configured to communicatively couple the controller to the plurality of electrodes and associated circuitry disposed about the band. In implementations, the conductive wiring 140 can be woven into the warp and weft of the fabric. In implementations, the conductive wiring 140 can be integrated into the fabric, disposed between layers of the band 110. In implementations, the conductive wiring 140 can include one or more conductive threads integrated into the fabric of the band 110. In examples, the one or more conductive threads can be integrated in a zigzag or other doubled back pattern so as to straighten as the band 110 stretches. The zigzag or doubled-back pattern therefore accommodates for stretching and patient movement while keeping the one or more conductive threads from contacting the skin of the patient. Integrating the conductive wiring 140 into the band 110 reduces and/or eliminates snagging the wire or thread on an external object. In other examples, the conductive thread can be routed on an exterior surface of the band 110 so as to avoid contacting the skin of the patient and therefore avoid irritation associated with such potential contact. In implementations, the conductive wiring 140 includes two or more conductive wires bundled within an insulating outer sheath. In implementations, the conductive wiring 140 can be routed along the band 110 and held securely to the band 110 by one or more loops of fabric, closable retention tabs, eyelets and/or other retainers so that the conductive wiring 140 does not snag on or bulge beneath a patient's clothing worn over the band 110.

In implementations, the conductive wiring 140 extends between the controller 120 and plurality of electrodes and associated circuitry and the one or more sensor ports 115. The one or more sensor ports 115 can include thereon a connector for receiving a complimentary mating portion of one or more additional sensors selectively disposed on the band 110. The connector of the one or more sensor ports 115 can be in wired communication with the conductive wiring 140 such that upon receiving a sensor therein, a sensor port 115 functions as a conduit for communicating information between the sensor and the processor 218 of the controller 120.

The ingress-protected housing of the controller 120 protects the components thereunder (e.g., the processor 218, the therapy delivery circuit 1130 including a polarity switching component such as an H-bridge 1128, a data storage 1207, a network interface 1206, a user interface 1208, at least one battery 1140, the sensor interface 1202, the alarm manager 1214, the one or more capacitors 1135, and the Sudden Cardiac Arrhythmia (SCA) Risk Analysis Assessor 219) from external environmental impact, for example damage associated with solid particle ingress, dust ingress, and/or moisture, water vapor or liquid ingress. In implementations, for example, the ingress-protected housing can be a two-piece housing having two interlocking shell portions configured to be mated in a sealed press fit. For example, a compressible grommet, o-ring, or silicon seal can be inserted between and/or about the mating surfaces such that ingress into the interlocked shall portions is prevented. Similarly, any additional openings can be similarly sealed to prevent ingress, such as any openings comprising user input buttons or electronics ports for mating with wired components. In some examples, ports for receiving wire connectors therein can be sealed to the housing of the controller 120 with an epoxy to prevent ingress.

Preventing such ingress protects the electronic components of the device 100 from short-circuiting or corrosion of moisture-sensitive electronics, for example, when a patient wears the device while showering. In implementations, the ingress-protected housing of the controller 120 includes at least one ingress-protected connector port 121 configured to receive at least one connector 141 of the conductive wiring 140. The at least one ingress-protected connector port can have an IP67 rating such that the device can be connected to the controller 120 and operable when a patient is showering or bathing, for example.

Example implementations of water-resistant housings of the controller 120 protect against liquid ingress in accordance with one or more scenarios as set forth in Table 1:

TABLE 1

| Protection Against | Effective Against (e.g. shall not impact normal operation of the medical device as described herein) |
| --- | --- |
| Dripping water | Falling drops of dripping water on the medical device housing, e.g., water dripping on the housing at a rate 1 mm per minute for a period of around 10 minutes. |
| Spraying water | Spray of water falling on the medical device housing at any angle up to 60 degrees from vertical. |
| Splashing of water | Water splashing against the housing from any direction. |
| Water jets | Water projected by a nozzle (e.g., a nozzle of 6.3 mm diameter) against the housing from any direction |
| Powerful water jets | Water projected in powerful jets (e.g., a nozzle of 12.5 mm diameter spraying water at a pressure of 100 kPa at a distance of 3 m) against the housing from any direction |
| Immersion, up to 1 m depth | The housing is immersed in water at a depth of up to 1 meter. |
| Immersion, 1 m or more depth | The housing is immersed in water at a depth of 1 meter or more. |
| Powerful high temperature water jets | The housing is sprayed with a high pressure (e.g. 8-10 MPa), high temperature (e.g. 80 degrees Celsius) spray at close range. |

In some implementations, the ingress-protected housing on the controller 120 is water-resistant and has a predetermined ingress protection rating complying with one or more of the rating levels set forth in IEC standard 60529. The liquid Ingress Protection rating can be one or more of any level (e.g., levels 3 to 9) in which rating compliance tests are specified in the standard. For example, to have a liquid ingress protection rating level of six, the ingress-protected housing of the controller 120 shall protect against ingress of water provided by a powerful water jet. The powerful water jet test requires that the housing of the controller 120 is sprayed from all practicable directions with a stream of water from a test nozzle having a 12.5 mm diameter. Water sprays for 1 minute per square meter for a minimum of three minutes at a volume of 100 liters per minute (+/−5 percent) so that a core of the stream of water is a circle of approximately 120 mm in diameter at a distance of 2.5 meters from the nozzle. For example, to have a rating level of 7, ingress of water shall not be possible when the housing of the controller 120 is completely immersed in water at a depth between 0.15 m and 1 m so that the lowest point of the housing of the controller 120 with a height less than 850 mm is located 1000 mm below the surface of the water and the highest point of a housing of the controller 120 with a height less than 850 mm is located 150 mm below the surface of the water. The controller 120 is immersed for a duration 30 minutes, and the water temperature does not differ from that of the housing of the controller 120 by more than 5K. Table 2 provides the rating levels and tests for liquid Ingress Protection in accordance with IEC standard 60529:

TABLE 2

| Rating Level | Degree of Protection | | Test conditions, see IEC 60529 section |
|---|---|---|---|
| | Brief Description | Definition | |
| 0 | Non-protected | — | — |
| 1 | Protected against vertically falling water drops | Vertically falling drops shall have no harmful effects | 14.2.1 |
| 2 | Protected against vertically falling water drops when housing tilted up to 15 degrees | Vertically falling drops shall have no harmful effects when the housing is tilted at any angle up to 15 degrees on either side of the vertical | 14.2.2 |
| 3 | Protected against spraying water | Water sprayed at an angle up to 60 degrees on either side of the vertical shall have no harmful effects | 14.2.3, including, for example, spraying water on the housing at 60 degrees from vertical at a water flow rate of 10 liters/min for at least 5 minutes |
| 4 | Protected against splashing water | Water splashed against the housing from any direction shall have no harmful effects | 14.2.4, including, for example, spraying water on the housing at 180 degrees from vertical at a water flow rate of 10 liters/min for at least 5 minutes |
| 5 | Protected against water jets | Water projected in jets against the housing from any direction shall have no harmful effects | 14.2.5, including, for example, spraying water from a 6.3 mm diameter nozzle at a distance of 2.5-3 m from the housing at a water flow rate of 12.5 liters/min for at least 3 minutes |
| 6 | Protected against powerful waterjets | Water projected in powerful jets against the housing from any direction shall have no harmful effects | 14.2.6, including, for example, spraying water from a 12.5 mm diameter nozzle at a distance of 2.5-3 m from the housing at a water flow rate of 100 liters/min for at least 3 minutes |
| 7 | Protected against the effects of temporary immersion in water | Ingress of water in quantities causing harmful effects shall not be possible when the housing is temporarily immersed in water under standardized conditions of pressure and time | 14.2.7, including, for example, immersion for 30 min in a water tank such that the bottom of the housing is 1 m below the surface of the water and the top of the housing is 0.15 m below the surface of the water |
| 8 | Protected against the effects of continuous immersion in water | Ingress of water in quantities causing harmful effects shall not be possible when the housing is continuously immersed in water under conditions which shall be agreed between manufacturer and user but which are more severe than for numeral 7 | 14.2.8, including, for example, immersion in a water tank such that the bottom of the housing is greater than 1 m below the surface of the water and the top of the housing is greater than 0.15 m below the surface of the water |

TABLE 2-continued

| Rating | Degree of Protection | | Test conditions, see |
|---|---|---|---|
| Level | Brief Description | Definition | IEC 60529 section |
| 9 | Protected against high pressure and temperature waterjets | Water projected at high pressure and high temperature against the housing from any direction shall not have harmful effects | 14.2.9, including, for example, spraying water on the housing from all practical directions from a fan jet nozzle at a distance of 175 +/− 25 mm from the housing and spraying water at a flow rate of 15 liters/min for at least 3 min |

For example, the housing of the controller 120 can be constructed to be water-resistant and tested for such in accordance with the IEC 60529 standard for Ingress Protection. For instance, the controller 120 of the device 100 may be configured to have a rating of level 7, protecting against immersion in water, up to one meter for thirty minutes. This enables a patient to wear the device 100 in the bathtub or shower for uninterrupted, continuous use. In implementations, the controller 120 of the device 100 may be multiple coded, including two or more levels. For example, the controller 120 of the device 100 can maintain a liquid Ingress Protection level of 7, protecting against temporary immersion, and a liquid Ingress Protection level of 5, protecting against water jets.

As described previously, the housing of the controller 120 shields one or more of the contents within the controller from environmental impact. These contents can include one or more of the treatment delivery circuit, an ECG acquisition and conditioning circuit, the processor, at least one capacitor, and at least one power source (e.g., a battery). The controller 120 covers and/or surrounds the hardware components therein, protecting them from wear and tear and protecting the patient from contacting high voltage components. The controller 120 protects the components from liquid ingress while the patient is showering, for example. In examples, the housing of the controller 120 can comprise or consist of at least one of neoprene, thermoformed plastic, or injection molded rubber or plastic, such as silicone or other biocompatible synthetic rubber.

Additionally, the band 110 can be water vapor-permeable, and substantially liquid-impermeable or waterproof. The band 110 may comprise or consist of an elastic polyurethane fiber that provides stretch and recovery. For example, the band 110 may comprise or consist of at least one of neoprene, spandex, nylon-spandex, nylon-LYCRA, ROICA, LINEL, INVIYA, ELASPAN, ACEPORA, and ESPA. In implementations, a portion of the band 110 comprises a water resistant and/or waterproof fabric covering and/or encapsulating electronic components including, for example, the sensing electrodes 112, the treatment electrodes 114, and the conductive wiring 140, and a portion of the band comprises a water permeable, breathable fabric having a relatively higher moisture vapor transmission rate that the water resistant and/or waterproof portions. In examples, the band 110 can comprise or consist of a fabric having a biocompatible surface treatment rendering the fabric water resistant and/or waterproof. For example, the fabric can be enhanced by dipping in a bath of fluorocarbon, such as Teflon or fluorinated-decyl polyhedral oligomeric silsesquioxane (F-POSS). Additionally or alternatively, the band 110 can comprise or consist of a fabric including anti-bacterial and/or anti-microbial yarns. For example, these yarns can include a base material of at least one of nylon, polytetrafluoroethylene, and polyester. These yarns can be for example, one or more of an antibacterial silver coated yarn, antibacterial DRALON yarn, DRYTEX ANTI-BACTERIAL yarn, NILIT BREEZE and NILIT BODY-FRESH. In implementations, the outer surface of the band 110 can comprise one or more patches of an electrostatically dissipative material such as a conductor-filled or conductive plastic in order to prevent static cling of a patient's clothing. Alternatively, in embodiments, the band 110 comprises a static dissipative coating such as LICRON CRYSTAL ESD Safe Coating (TECHSPRAY, Kennesaw, GA), a clear electrostatic dissipative urethane coating.

Returning to FIGS. 2A-B, the band 110 can be sized to fit about the thoracic region 105 of the patient by matching the length L1 of the band 110 to one or more circumferential measurements of the thoracic region 105 during an initial fitting. For example, in an initial fitting, a caregiver, physician or patient service representative (PSR) can measure the circumference of the thoracic region 105 of the patient at one or more locations disposed about the thoracic region 105 between about the T1 thoracic region and the T12 thoracic region, and select a band 110 having a length L1 within a range of 2-25% longer than the largest measured circumference. Having the band 110 be longer than the largest measured circumference of the thoracic region 105 can provide the patient with a comfort advantage of loosening and tightening the band 110 to accommodate fluctuations in body mass throughout the prescribed duration of wear. In embodiments of the device 100 having a fastener configured to secure the band 110 about the thoracic region 105, the patient can loosen or reposition the band around one or more positions along the thoracic region 105 between about the T1 thoracic region and T12 thoracic region.

Additionally or alternatively, the band 110 can have proportions and dimensions derived from patient-specific thoracic 3D scan dimensions. From a 3-dimensional scan of the thoracic region 105 of the patient, a band can be sized to fit proportions, dimensions, and shape of the thoracic region 105. In implementations, for example, various body size measurements and/or contoured mappings may be obtained from the patient, and one or more portions of the band 110 can be formed of a plastic or polymer to have contours accommodating one or more portions of the thoracic region in a nested fit. For example one or more portions of the band may be 3D printed from, for example, any suitable thermoplastic (e.g., ABS plastic) or any elastomeric and/or flexible 3D printable material. For example the band 110 may include at least two curved rigid or semi-rigid portions 109a, 109b for engaging the patient's sides, under the arms. The at least two curved portions add rigid structure that assists with preventing the band 110 from shifting or rotating about the thoracic region. This stability provides consistency of sensor signal readings and prevents noise associated with sensor movement.

Stability of the device is also provided by the at least one compression portion. The compressive forces of the band 110 prevent movement of the band 110 relative to the skin surface of the thoracic region 105 and reduce or eliminate noise artifacts associated with sensors moving relative to the surface of the skin of the thoracic region 105. In one implementation, the band 110 includes joinable ends 145a, 145b, and the compression portion comprises an adjustable fastener 147 for securing the band about the thoracic region 105 of the patient within the range of compression forces. The range of compression forces secures the band 110 from movement without the patient developing soreness or compression ulcers during the continuous period of wear. In implementations, the fastener can include a ratchet, a belt buckle, hook and loop fasteners, snaps, buttons, eyelets, and any other mechanism for closing the band 110.

In implementations, the band 110 comprises at least one visible indicator 149 of band tension disposed on a surface of the band 110. For example, the visible indicator 149 can be a color changing indicator incorporated in the band 110 indicating whether the band 110 is too loose, overtightened, or compressed within the range of compressive forces. As the band 110 stretches, the material forming the visible indicator 149, for example, can change color between blue, indicating over-tensioning or under-tensioning, and yellow or green, indicating proper tensioning for simultaneously enabling sensor readings and patient comfort. In one implementation, the visible indicator 149 can comprise one or more stretchable, multilayer smart fibers disposed in or on the band 110. The one or more smart fibers change color from red, to orange, to yellow, to green and to blue as strain on the fiber increases. Providing a visible indication directly on the band 110 enables a patient to adjust or reapply the band 110 so that the at least one pair of ECG sensing electrodes 112 and at least one pair of treatment electrodes 114 are properly positioned and immobilized on the thoracic region 105 and so that the band isn't overtightened and applying compressive forces in the thoracic region 105 to a level of patient discomfort. In other implementations, the band can include a mechanical strain gauge in or on the band 110. The mechanical strain gauge can be communicatively coupled to the conductive wiring 140 such that the controller 120 provides an audible and/or visible indication of whether the band is over-tightened, too loose, or within the range of compression forces enabling effective use and wear comfort.

In implementations, the band comprises an unbroken loop and the compression portion comprises a stretchable fabric defining the band 110. The band 110 can be configured to stretch over the shoulders or hips of the patient and contract when positioned about the thoracic region 105. In implementations, the stretchable fabric comprises at least one of nylon, LYCRA, spandex, and neoprene. During an initial fitting, the physician, caregiver, or PSR can select a band 110 sized to fit the patient. For example, the physician, caregiver, or PSR can measure a circumference about one or more locations on the thoracic region 105. The physician, caregiver, or PSR can select a band having a circumference within about 75% to about 95% of the measurement of the one or more locations about the thoracic region 105. In some implementations, the compression portion comprises an elasticized thread disposed in the band 110. The compression portion can comprise an elasticized panel disposed in the band, the elasticized panel comprising a portion of the band 110 spanning less than a total length of the band 110. For example, the band 110 can include one or more mechanically joined sections forming a continuous length or unbroken loop. The one of the one or more sections can comprise a stretchable fabric and/or elasticized thread interspersed with non-stretchable or relatively less stretchable portions. In other embodiments, the band 110 can include a compression portion comprising an adjustable tension element, such as one or more cables disposed in the band 110 and configured to be pulled taught and held in tension by one or more pull stops. In all embodiments, the band 110 can include one or more visible or mechanical tension indicators configured to provide a notification of the band 110 exerting compression forces against the thoracic region 105 in a range from about 0.025 psi to 0.75 psi.

As described herein, the band 110 is immobilized by compression forces and configured to minimize shifting as the patient moves and goes about a daily routine. Because no portion of the band 110 traverses the patient's limbs or shoulders, the patient is free to move, bend, twist and lift his or her arms and/or shoulders without imparting torque on the device 100. This immobilizes the band 110 relative to the skin surface of the thoracic region and prevents or eliminates signal noise associated with sensors shifting against the skin when compared to wearable devices that run over a patient's shoulder or arm. The size and position of the band 110 also provides a discreet and comfortable device 100 covering only a relatively small portion of the surface area of the entire thoracic region 105 and accommodating a plurality of body types. A relatively small portion can be for example, 25%, or less (e.g. 20%, 15%, 10%, 5% or less than 5%) of the surface area of the thoracic region 105. Covering only a relatively small portion of the thoracic region 105 further improves comfort and encourages patient compliance because the patient will feel little or no discomfort and may forget the device 100 is being worn. In implementations, the band comprises a breathable, skin-facing layer including at least one of a compression padding, a silicone tread, and one or more textured surface contours. The breathable material and compression padding enable patient comfort throughout the duration of wear and the silicon tread and/or one or more surface contours assist with immobilizing the band relative to the skin surface of the thoracic region.

Implementations of the device 100 in accordance with the present disclosure may exhibit a moisture vapor transmission rate (MVTR) of, for example, between about 600 $g/m^2$/day and about 1,400 $g/m^2$/day when worn by a subject in an environment at room temperature (e.g., about 25° C.) and at a relative humidity of, for example, about 70%. In implementations, the device 100 has a water vapor permeability of 100 $g/m^2$/24 hours, as measured by such vapor transmission standards of ASTM E-96-80 (Version E96/E96M-13), using either the "in contact with water vapor" ("dry") or "in contact with liquid" ("wet") methods. Such test methods are described in U.S. Pat. No. 9,867,976, titled "LONG-TERM WEAR ELECTRODE," issued on Jan. 16, 2018 (hereinafter the "'976 Patent"), the disclosure of which is incorporated by reference herein in its entirety. In implementations, the band 110 comprises one or more moisture wicking fabrics for assisting with moving moisture away from the skin of the thoracic region 105 and improving patient comfort throughout the prescribed duration of wear.

In implementations, the device includes an adhesive configured to immobilize the band 110 relative to the thoracic region of the patient. In implementations, the adhesive is configured to be a removable and/or replaceable adhesive patch for preventing the band 110 from shifting, rotating, or slipping relative to the skin of the thoracic region. In implementations, once the patient is wearing the band 110 and has adjusted the band in implementations comprising an adjustment and/or tightening mechanism, the patient can insert on or more adhesive patches between the band 110 and the skin. In implementations, the patient can swap out one or more adhesive patches with one or more new adhesive patches in the same or a different location between the band 110 and the skin of the thoracic region 105. For example, the patient may swap out the one or more adhesive patches on a daily schedule or may use the adhesive patches selectively during periods of high activity, such as while exercising. The adhesives can include biocompatible adhesives, such as pressure-sensitive adhesives having tack, adhesion, and cohesion properties suitable for use with a medical device applied to skin for short term and long-term durations. These pressure sensitive adhesives can include polymers such as acrylics, rubbers, silicones, and polyurethanes having a high initial tack for adhering to skin. These pressure sensitive adhesives also maintain adhesion during showering or while a patient is perspiring. The adhesives also enable removal without leaving behind uncomfortable residue. For example, such an adhesive can be a rubber blended with a tackifier.

In implementations, the adhesive comprises one or more water vapor permeable adhesive patches. The adhesive can be a conductive patch disposed between the plurality of electrodes and the skin of thoracic region 105, in some implementations. For example, as described in the '976 patent, a water-vapor permeable conductive adhesive patch can be, for example, the flexible, water vapor-permeable, conductive adhesive material can comprise a material selected from the group consisting of an electro-spun polyurethane adhesive, a polymerized microemulsion pressure sensitive adhesive, an organic conductive polymer, an organic semi-conductive conductive polymer, an organic conductive compound and a semi-conductive conductive compound, and combinations thereof. In an example, a thickness of the flexible, water vapor-permeable, conductive adhesive material can be between 0.25 and 100 mils. In another example, the water vapor-permeable, conductive adhesive material can comprise conductive particles. In implementations, the conductive particles may be microscopic or nano-scale particles or fibers of materials, including but not limited to, one or more of carbon black, silver, nickel, graphene, graphite, carbon nanotubes, and/or other conductive biocompatible metals such as aluminum, copper, gold, and/or platinum.

The device 100 herein includes low skin-irritation fabrics and/or adhesives. In embodiments, the device 100 may be worn continuously by a patient for a long-term duration (e.g., duration of at least one week, at least 30 days, at least one month, at least two months, at least three months, at least six months, and at least one year) without the patient experiencing significant skin irritation. For example, a measure of skin irritation can be based on skin irritation grading of one or more as set forth in Table C.1 of Annex C of American National Standard ANSI/AAMI/ISO 10993-10:2010, reproduced here in the entirety:

TABLE C.1

Table 3
Human Skin irritation test, grading scale

| Description of response | Grading |
| --- | --- |
| No reaction | 0 |
| Weakly positive reaction (usually characterized by mild erythema and/or dryness across most of the treatment site) | 1 |
| Moderately positive reaction (usually distinct erythema or dryness, possibly spreading beyond the treatment site) | 2 |
| Strongly positive reaction (strong and often spreading erythema with edema and/or eschar formation) | 3 |

The skin irritation grading of one represents a weakly positive reaction usually characterized by mild erythema and/or dryness across most of the treatment site. In one implementation, a measure of skin irritation can be determined by testing on human subjects in accordance with the method set forth in American National Standard ANSI/AAMI/ISO 10993-10:2010, by applying sample patches of the adhesive and/or fabric to treatment sites for up to four hours, and, in the absence of skin irritation, subsequently applying sample patches to treatment sites for up to 24 hours. The treatment sites are examined for signs of skin irritation, and the responses are scored immediately after patch removal and at time intervals of $(1\pm 0.1)$ h to $(2\pm 1)$ h, $(24\pm 2)$ h, $(48\pm 2)$ h and $(72\pm 2)$ h after patch removal. In another implementation, a patient may wear the device 100 as instructed for a duration of $(24\pm 2)$ hours, and if the patient's skin shows no reaction at the end of this duration, the device 100 is rated as a skin irritation grading of zero.

Treatment is caused to be provided by the treatment delivery circuit in communication with the at least one pair of treatment electrodes 114. In implementations, as shown in FIGS. 2A and 2B, the band 110 further comprises at least one of an anterior appendage 150 and a posterior appendage 155, and at least one of the plurality of electrodes is disposed on the at least one of the anterior appendage and the posterior appendage. In implementations, one treatment electrode 114a of the at least one pair of treatment electrodes 114 is disposed on the anterior appendage 150 and one treatment electrode 114b of the at least one pair of treatment electrodes 114 is disposed on the posterior appendage 155. In implementations, each of the at least one of the anterior appendage and the posterior appendage is a flap extending vertically along the thoracic region from a circumferential top edge 160 or a circumferential bottom edge 165 of the band 110. In implementations, the anterior appendage and the posterior appendage cumulatively occupy 50 percent or less of the length of the band 110 so as to minimize the surface area of the thoracic region 105 covered by the device 100 which providing an effective placement of the at least one pair of treatment electrodes 114. By positioning the at least one pair of treatment electrodes 114 on either side of the patient's heart, the device 100 can deliver effective treatment along a vector through the heart, restoring a normal rhythm upon detection of a cardiac arrhythmia requiring treatment. As depicted in FIGS. 2A-B, the anterior and posterior appendages 150, 155 rise from a top circumferential edge 160 of the band 110. In such implementations, an average vertical rise V2, V3 from a bottom edge 165 of the band 110 to a top edge 170, 175 of each of the at least one of the anterior appendage 150 and the posterior appendage 155 is greater than the average vertical rise V1 of the band.

In implementations, at least one of the anterior appendage 150 and the posterior appendage 155 includes disposed thereon at least one ECG sensing electrode 112. In implementations, such as that of FIG. 5, the device can include one or more appendages 111a, 111b mechanically attached to the band 110, the one or more appendages 111a, 111b, configured to be continuously worn about the thoracic region 105 of the patient. In addition to supporting one more additional ECG sensing electrodes 112 thereon, the one or more appendages 111a, 111b are configured to receive one or more selectively added treatment electrodes 114, shown in dashed line to indicate their being added to the device 100 optionally. In implementations, the device 100 can be configured to monitoring a patient's ECG signal, analyze the signal, predict a future event occurring based on the analysis, and provide an instruction to patient or caregiver to add the optional treatment electrodes to the one or more appendages 111a, 111b and the band 110.

Figure 6A:
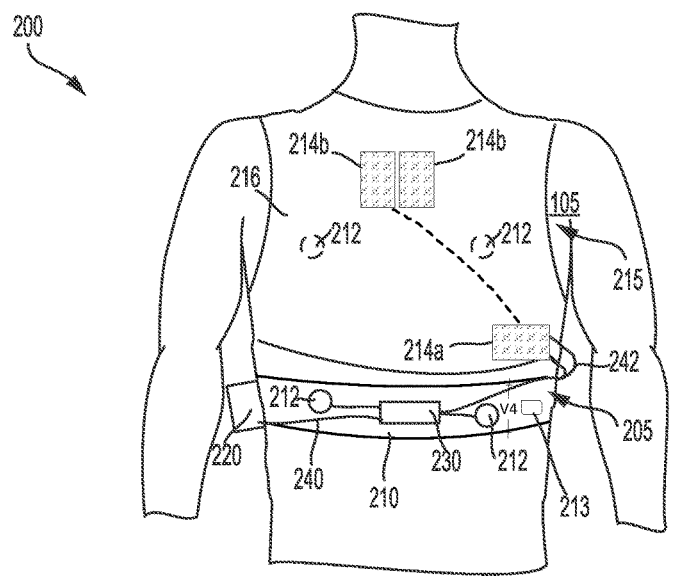
FIG. 6A depicts an embodiment of a patient-worn cardiac monitoring and treatment system comprising a first wearable portion and a second wearable portion.

In other implementations, such as that of FIG. 6A, a cardiac monitoring and treatment system 200 includes a first wearable portion 205 and a second, separately worn portion 215 including one or more treatment electrodes 214a, 214b (collectively referred to as 214) disposed on the second wearable portion 215. The treatment electrodes 214 are disposed in the second wearable portion 215 such that a treatment vector formed between the treatment electrodes 214 is aligned through the patient's heart when the second wearable portion 215 is worn.

In implementations, a cardiac monitoring and treatment system can include a controller 220 comprising at least one processor, a first wearable portion 205, and a second wearable portion 215. In implementations, as shown in FIG. 7, the controller 220 can include the at least one processor 218, a therapy delivery circuit 1130 including a polarity switching component such as an H-bridge 1128, a data storage 1207, a network interface 1206, a user interface 1208, at least one battery 1140, a sensor interface 1202 that includes, for example, an ECG data acquisition and conditioning circuit, an alarm manager 1214, one or more capacitors 1135, and a Sudden Cardiac Arrhythmia (SCA) Risk Analysis Assessor 219.

In implementations, the first wearable portion 205 includes an elongated strap 210, similar to the band 110 of FIGS. 2A-B, configured to encircle a thoracic region 105 of a patient. The elongated strap 210 is configured to be immobilized relative to a skin surface of the thoracic region 105 of the patient by exerting one or more compression forces against the thoracic region. For example, the compression force can be in a range from 0.025 psi to 0.75 psi, 0.05 psi to 0.70 psi, 0.075 psi to 0.675 psi, or 0.1 to about 0.65 psi. In implementations, the strap 210 exerts compression forces against the skin of the patient by one or more of manufacturing all or a portion of the strap 210 from a compression fabric, providing one or more tensioning mechanisms in and/or on the strap 210, and proving a cinching closure mechanism for securing and compressing the strap 210 about the thoracic region 105. Compression forces of the medical device can be determined, for example, using one or more pressure sensors and systems as described above with regard to the band 110 of FIG. 2A. The first wearable portion 205 includes a plurality of ECG sensing electrodes 212 disposed about the elongated strap 210. The plurality of ECG sensing electrodes is configured to sense an ECG signal of the patient. The plurality of ECG sensing electrodes 212 can be disposed about the elongated strap 210 and configured to be in electrical contact with the patient. In implementations, the plurality of ECG sensing electrodes can include a driven ground electrode, or right leg drive electrode, configured to ground the patient and reduce noise in the sensed ECG signal.

In embodiments, the plurality of ECG sensing electrodes 212 are configured to be assembled into the elongated strap 210 or removably attached to the elongated strap, using, for example, hook and loop fasteners, thermoform press fit receptacles, snaps, and magnets, among other restraints. An example ECG sensing electrode 212 includes a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference. In some implementations, as described previously, the plurality of ECG sensing electrodes 212 can be a permanent portion of the elongated strap 210. For example, the plurality of ECG sensing electrodes 212 can be formed of the warp and weft of a fabric forming at least a layer of the elongated strap 210. In implementations, the plurality of ECG sensing electrodes 212 are formed from conductive fibers that are interwoven with non-conductive fibers of the fabric. In some implementations, the plurality of ECG sensing electrodes 212 are metallic plates (e.g. stainless steel) or substrates that are formed as permanent portions of the elongated strap 210. A metallic plate or substrate can be adhered to the elongated strap 210, for example, by a polyurethane adhesive or a polymer dispersion adhesive such as a polyvinyl acetate (PVAc) based adhesive, or other such adhesive. In examples, the plurality of ECG sensing electrodes 212 are a plurality of dry ECG sensing electrodes. In examples, plurality of ECG sensing electrodes 212 are flexible, dry surface electrodes such as, for example, conductive polymer-coated nano-particle loaded polysiloxane electrodes mounted to the elongated strap 210. In some examples, the plurality of ECG sensing electrodes 212 are flexible, dry surface electrodes such as, for example silver coated conductive polymer foam soft electrodes mounted to the elongated strap 210. In examples, the plurality of ECG sensing electrodes 212 are screen printed onto the elongated strap 210 with a metallic ink, such as a silver-based ink. In implementations, each of the plurality of ECG sensing electrodes 212 has a conductive surface adapted for placement adjacent the patient's skin.

In implementations, the first wearable portion 205 includes one or more receiving ports 213 configured to receive one or more additional components including at least one of a treatment electrode 214 and an additional sensor. The additional sensor can be, for example, one or more physiological sensors for detecting one or more of pulmonary vibrations (e.g., using microphones and/or accelerometers), breath vibrations, sleep related parameters (e.g., snoring, sleep apnea), and tissue fluids (e.g., using radiofrequency transmitters and sensors). The additional sensor can be, for example, one or more physiological sensors including a pressure sensor for sensing compression forces of the garment, SpO2 sensors, blood pressure sensors, bioimpedance sensors, humidity sensors, temperature sensors, and photoplethysmography sensors. In implementations, the one or more receiving ports 213 enable the one or more additional components to be assembled into the elongated strap 210 or removably attached to the elongated strap 210, using, for example, hook and loop fasteners, thermoform press fit receptacles, snaps, and magnets, among other restraints and/or mating features. In some examples, the ports 213 can also be configured to receive one or more motion and/or position sensors. For example, such motion sensors can include accelerometers for monitoring the movement of the patient's torso in x-, y- and z-axes to determine a movement of the patient, gait, and/or whether the patient is upright, standing, sitting, lying down, and/or elevated in bed with pillows. In certain implementations, one or more gyroscopes may also be provided to monitor an orientation of the patient's torso in space to provide information on, e.g., whether the patient is lying face down or face up, or a direction in which the patient is facing.

In implementations, the first wearable portion 205 includes a plurality of conductive wires 240 configured to couple the plurality of ECG sensing electrodes 212 and the one or more receiving ports 213 with the controller 220. In implementations, the plurality of conductive wires 240 extends between the controller 220 and plurality of ECG sensing electrodes 212 and the one or more receiving ports 213. The one or more receiving ports 213 can include thereon a connector for receiving a complimentary mating portion of one or more additional sensors selectively disposed on the elongated strap 210. The connector of the one or more ports 213 can be in wired communication with the plurality of conductive wires 240 such that upon receiving a sensor therein, the one or more receiving ports 213 each function as a conduit for communicating information between the additional sensor and the controller 220.

In implementations, the elongated strap 210 comprises a fabric. The elongated strap 210 may comprise or consist of an elastic polyurethane fiber that provides stretch and recovery. For example, the elongated strap 210 may comprise or consist of at least one of neoprene, spandex, nylon-spandex, nylon-LYCRA, ROICA, LINEL, INVIYA, ELASPAN, ACEPORA, and ESPA. In examples, the elongated strap 210 can comprise or consist of a fabric having a biocompatible surface treatment rendering the fabric water resistant and/or waterproof. In implementations, a portion of the elongated strap 210 comprises a water resistant and/or waterproof fabric covering and/or encapsulating electronic components including, for example, the sensing electrodes 212, the treatment electrodes 214, and the plurality of conductive wires 240, and a portion of the elongated strap 210 comprises a water permeable, breathable fabric having a relatively higher moisture vapor transmission rate that the water resistant and/or waterproof portions.

In implementations, a plurality of conductive wires 240 can be woven into the warp and weft of the fabric. In implementations, the plurality of conductive wires 240 can be integrated into the fabric, disposed between layers of the elongated strap 210. In implementations, the elongated strap 210 can include the plurality of conductive wires 240 integrated into the fabric of the elongated strap 210. In implementations, the plurality of conductive wires 240 can comprise or consist of conductive thread. In examples, the plurality of conductive wires 240 can be integrated in a zigzag or other doubled back pattern so as to straighten as the elongated strap 210 stretches. The zigzag or doubled-back pattern therefore accommodates for stretching and patient movement while keeping the plurality of conductive wires 240 from contacting the skin of the patient. Integrating the plurality of conductive wires 240 into the elongated strap 210 reduces and/or eliminates snagging the wire or thread on an external object. In other examples, the plurality of conductive wires 240 can be routed on an exterior surface of the elongated strap 210 so as to avoid contacting the skin of the patient and therefore avoid irritation associated with such potential contact. In implementations, the plurality of conductive wires 240 includes two or more conductive wires bundled within an insulating outer sheath. In implementations, the plurality of conductive wires 240 can be routed along the elongated strap and held securely to the elongated strap 210 by one or more loops of fabric, closable retention tabs, eyelets and/or other retainers so that the plurality of conductive wires 240 do not snag on or bulge beneath a patient's clothing worn over the elongated strap 210.

In implementations of the system 200, the second wearable portion 215 is separate from the first wearable portion 205. The second wearable portion 215 is configured to be worn over at least one shoulder of the patient. In implementations, the second wearable portion 215 includes a wearable substrate 216, one or more treatment electrodes 214 disposed on the wearable substrate 216, and at least one conductive wire 242 configured to releasably connect the one or more treatment electrodes 214 to the controller 220. The one or more treatment electrodes 214 includes an anterior treatment electrode 214a and a posterior treatment electrode 214b. Each of the one or more treatment electrodes 214 comprises a corresponding conductive surface configured to contact the patient's skin at an anterior area and a posterior area of the thoracic region 105 of the patient.

The one or more treatment electrodes 214 are configured to be assembled into the wearable substrate 216 or removably attached to the wearable substrate, using, for example, pockets formed in or on the wearable substrate, hook and loop fasteners, thermoform press fit receptacles, snaps, and magnets, among other restraints. In some implementations, the one or more treatment electrodes 214 can be a permanent portion of the wearable substrate 216. In implementations, the wearable substrate 216 comprises or consists of fabric. The fabric may comprise or consist of an elastic polyurethane fiber that provides stretch and recovery. For example, the fabric may comprise or consist of at least one of neoprene, spandex, nylon-spandex, nylon-LYCRA, ROICA, LINEL, INVIYA, ELASPAN, ACEPORA, and ESPA. In implementations, the one or more treatment electrodes 214 can be formed of the warp and weft of a fabric forming at least a layer of the wearable substrate 216. In implementations, the one or more treatment electrodes 214 are formed from conductive fibers that are interwoven with non-conductive fibers of the fabric. In some implementations, the one or more treatment electrodes 214 are metallic plates (e.g. stainless steel) or substrates that are formed as permanent portions of the wearable substrate 216. A metallic plate or substrate can be adhered to the wearable substrate, for example, by a polyurethane adhesive or a polymer dispersion adhesive such as a polyvinyl acetate (PVAc) based adhesive, or other such adhesive. In examples, the one or more treatment electrodes 214 are screen printed onto the wearable substrate 216 with a metallic ink, such as a silver-based ink.

As previously described, the example devices and systems described herein are prescribed to be worn continuously and typically for a prescribed duration of time. For example, the prescribed duration can be a duration for which a patient is instructed by a caregiver to wear the device in compliance with device use instructions. As noted above, the prescribed duration may be for a short period of time until a follow up medical appointment (e.g., 1 hour to about 24 hours, 1 day to about 14 days, or 14 days to about one month), or a longer period of time (e.g., 1 month to about 3 months) during which diagnostics information about the patient is being collected even as the patient is being protected against cardiac arrhythmias. The prescribed use can be uninterrupted until a physician or other caregiver provides a specific prescription to the patient to stop using the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for an extended period of at least one year.

Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, every few hours, once a day, once a week, or other interval set by a technician or prescribed by a caregiver). Alternatively or additionally, the monitoring and/or recording during intervals or times can be triggered by a user action or another event. The user can be any one of the patient, remote or local physician, remote or local caregiver, or a remote or local technician, for example.

Because these devices require continuous operation and wear by patients to which they are prescribed, advantages of the implementations herein include use of comfortable, non-irritating construction materials and features designed to enhance patient compliance. Such compliance-inducing design features include, for example, device ergonomics, weight of the components and/or distribution of the weight about the device or portions of the device, and inconspicuous appearance when worn under outer garments (e.g., patient clothing), among others. In some implementations described herein, the devices include various features that promote comfort while continuing to protect the patient from adverse cardiac events. These features can be tailored in accordance with patient comfort preference and body morphology.

Figure 6B:
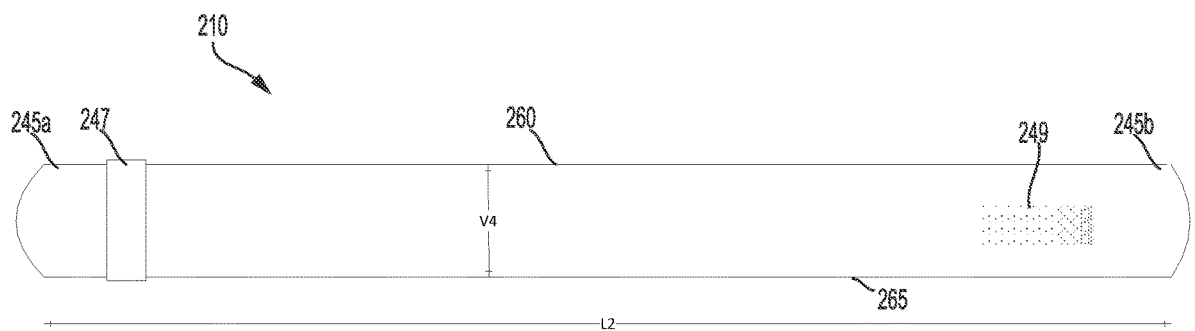
FIG. 6B depicts a schematic of the first wearable portion of FIG. 6A.

Segregating functionality between a first wearable portion 205 and a second wearable portion 215 of the system 200 of FIG. 6A provides advantages of increased patient comfort and device modularity while mitigating motion artifacts associated with the plurality of ECG sensing electrodes 212 shifting or sliding against the skin of the patient during a continuous duration of wear. Because the first wearable portion 205 includes sensors for monitoring one or more physiological conditions of the patient, e.g. the plurality of ECG sensing electrodes 212 and the additional sensor, the first wearable portion 205 is configured to be worn continuously or nearly continuously for a prescribed duration of wear. As previously described, that elongated strap 210 encircles the thoracic region 105 of the patient. As shown in FIG. 6B, in implementations, the elongated strap 210 has a vertical span V4 from a bottom circumferential edge 265 to a top circumferential edge 260 in a range of 1 to about 15 centimeters. For example, in implementations, the vertical span V4 is between 2 to 12 centimeters. For example, in implementations, the vertical span V4 is between 3 to 8 centimeters. The elongated strap 210 exerts a radial compression force in a range of 0.025 psi to 0.75 psi to the thoracic region 105 of the patient. In implementations the second wearable portion 215 comprises a compression force relatively lower than the compression force of the elongated strap 210. In implementations the second wearable portion 215 comprises one or more compression forces relatively lower than the compression force of the elongated strap 210. In implementations the second wearable portion 215 comprises an average compression force relatively lower than the compression force of the elongated strap 210. Compression forces of the medical device can be determined, for example, using one or more pressure sensors and systems as described above with regard to the band 110 of FIG. 2A. In implementations, the second wearable portion 215 is configured to be worn for a cumulative duration less than or equal to the duration of wear of the first wearable portion 205 as will be described subsequently.

Because the elongated strap 210 has a vertical span V4 in a range of 1 to about 15 centimeters (e.g., 1 cm, 2 cm, 3 cm, 4 cm, 5 cm, 6 cm, 7 cm, 8 cm, 9 cm, 10 cm, 11 cm, 12 cm, 13 cm, 14 cm, 15 cm) and is configured to be worn about the thoracic region 105 at a position or a range of positions between around about the T1 thoracic region to about the T12 thoracic region, the system 200 accommodates a variety of body sizes and morphologies by avoiding anatomically diverse regions of the human body. Similarly to the embodiment shown in FIGS. 3A-B, the elongated strap 210 is configured to be worn, for example, about the thoracic region at a position that can avoid a chest area and any protruding stomach area. In implementations, the strap 210 is configured to be worn within a T5 thoracic vertebra region and a T11 thoracic vertebra region. In implementations, the strap 210 is configured to be worn within a T8 thoracic vertebra region and a T10 thoracic vertebra region. By securing the elongated strap 210 on the thoracic region 105 in this range, the system 200 immobilizes the ECG sensing electrodes 212 and any additional sensor against the skin of the patient in a relatively smooth sensor surface to skin surface arrangement. This ensures complete sensor contact with the skin of the patient while reducing or eliminating motion artifacts regardless of patient gender or body type. This placement of the elongated strap 210 also avoids interference with a patient's arms and prevents movement of the elongated strap 210 as the patient goes about a daily routine, moving, shifting, bending, twisting, lifting arms, etc. The elongated strap 210 is discreetly and comfortably secured without covering a substantial portion of the patient's thoracic region 105. A substantial portion can be for example, 25%, 30%, 35%, 40%, 45%, 50% or more than 50% of the thoracic region 105.

The second wearable portion 215 can be worn for a portion of the prescribed cumulative duration of wear as will be described subsequently with regard to FIGS. 8A and 8B. Because the second wearable portion 215 comprises one or more treatment electrodes 214, the compression forces of the second portion need not be as great as those of the first wearable portion 205 having thereon or therein sensing electrodes sensitive to motion artifacts. In implementations, the first wearable portion 205 can be worn independently of the second wearable portion 215 and can be configured to provide monitoring functionality. In implementations, the first wearable portion 205 includes one or more receiving ports 213 configured to receive an additional sensor. Because the first wearable portion 205 is a compression device, the first wearable portion 205 supports monitoring sensors and/or sensing devices without the need for potentially irritating skin adhesives. Such adhesives are generally used to apply independently worn sensors and/or devices, but the first wearable portion 205 is immobilized by compression forces, reducing or eliminating a need for adhesives.

As previously described, in implementations, the system 200 is a cardiac monitoring and treatment system and the first wearable portion 205 comprises a plurality of ECG sensing electrodes 212. In implementations, the system 200 includes an ECG acquisition circuit in communication with the plurality of ECG sensing electrodes 212 and the at least one processor 218 of the controller 220. The ECG acquisition circuit is configured to provide ECG information for the patient based on the sensed ECG signal. In one implementation, the ECG acquisition circuit is collocated with the plurality of ECG sensing electrodes 212. In one implementation, the ECG acquisition circuit is located on the device controller 220. In implementations, the system 200 includes a connection pod 230 in wired connection with one or more of the plurality of ECG sensing electrodes 212 and the ECG acquisition circuitry. In some examples, the connection pod 230 includes at least one of the ECG acquisition circuitry and a signal processor configured to amplify, filter, and digitize the cardiac signals prior to transmitting the cardiac signals to the controller 220. In implementations, the system can include at least one ECG sensing electrode 212 configured to be adhesively attached to an upper portion of the thoracic region 105, above the elongated strap, the at least one ECG sensing electrode 212 being in wired communication with at least one of the connection pod and the controller 220.

As previously described, the second wearable portion 215 is configured to be worn for a cumulative duration less than or equal to the duration of wear of the first wearable portion 205. In implementations of the system 200, the at least one processor 218 is configured to predict a likelihood of a cardiac event based on an analysis of the ECG information and provide a notification to the patient to wear the second wearable portion 215 upon detecting the impending cardiac event. In implementations, the controller 220 includes a set of instructions comprising a Sudden Cardia Arrhythmia (SCA) risk analysis assessor 219. The SCA risk analysis assessor 219 provides a set of instructions to the processor for computing an SCA Risk score and analyzing whether the likelihood of an SCA occurring is high or not. Because the SCA risk analysis assessor 219 is predictive, the at least one processor 218 can determine, for example, a high likelihood of an SCA occurring in the next two weeks and prompt the controller 220 to provide an instruction and/or an alert to the patient to wear the second wearable portion 215 comprising the one or more treatment electrodes 214.

Figure 8A:
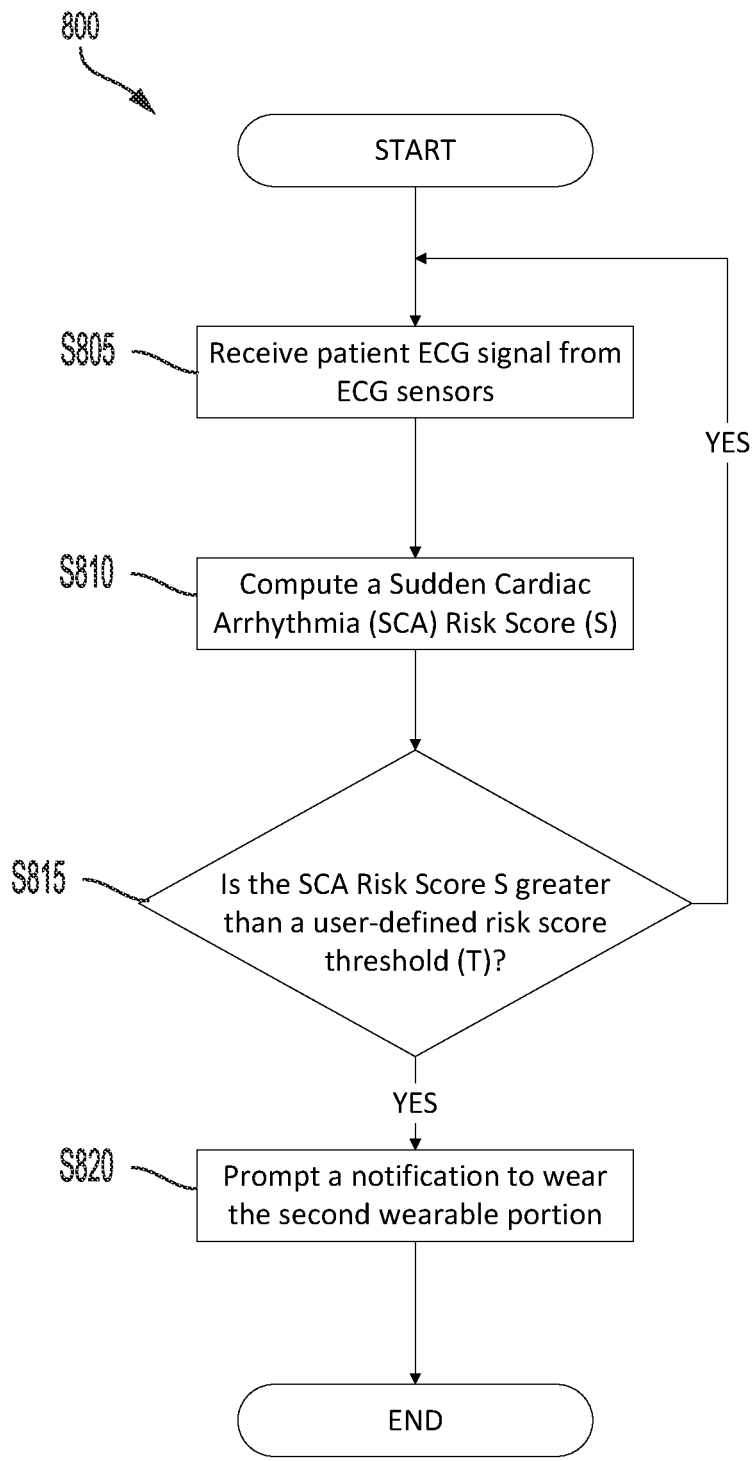
FIG. 8A depicts an embodiment a method of computing a sudden cardiac arrhythmia risk score.
Figure 8B:
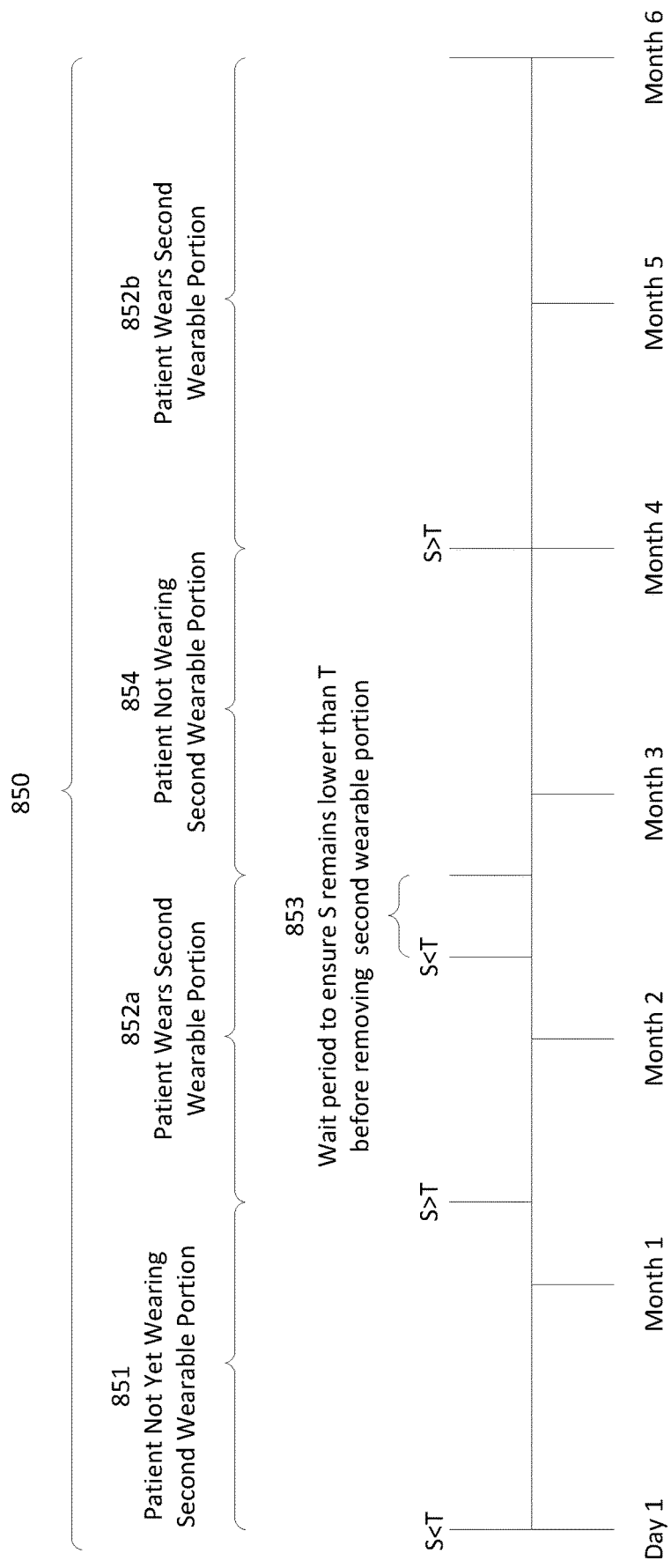
FIG. 8B depicts an embodiment of a timeline associated with a duration of wear of the patient-worn cardiac monitoring and treatment system.

As shown in FIGS. 8A and 8B, in implementations, the at least one processor 218 receives S805 the patient ECG signal from the plurality of ECG sensing electrodes 212 and computes S810 a sudden cardiac arrhythmia (SCA) risk score (S) in method 800. In implementations, the SCA risk score is computed based on at least one of ECG metrics passed from an ECG analyzer and patient demographic and clinical data. The ECG metrics can include, for example, one or more of the ECG metrics of table 4.

TABLE 4

| | | |
|---|---|---|
| Heart Rate | $HR_{avg}$ | Average heart rate |
| | $HR_{min}$ | Minimum heart rate |
| | $HR_{max}$ | Maximum heart rate |
| Heart Rate Variability | $NN_{avg}$ | Average normal-to-normal interval in seconds |
| | $NN_{min}$ | Minimum normal-to-normal interval in seconds |
| | $NN_{max}$ | Maximum normal-to-normal interval in seconds |
| | $NN_{sd}$ | Standard deviation of normal-to-normal intervals in seconds |
| | RMS | Square root of the mean squared difference of successive normal-to-normal intervals measured in seconds |
| | NN50 | Number of successive normal-to-normal intervals greater than 50 ms per minute. |
| | pNN50 | Percentage of normal-to-normal intervals greater than 50 ms per minute. |
| QRS Duration | $QRS_{med}$ | Median QRS duration |
| | $QRS_{sd}$ | Standard deviation of QRS duration |
| PVCs | $PVC_{count}$ | Number of PVCs |
| | nsvtCount | Number of consecutive heartbeat sequences of PVCs |

The patient demographic and clinical data include one or more of the metrics of table 5.

TABLE 5

| Demographic and clinical metrics |
|---|
| Age |
| Gender |
| Explant of implantable cardioverter defibrillator (ICD) |
| coronary artery bypass graft (CABG) |
| congestive heart failure (CHF) |
| hypertrophic cardiomyopathy (HCM) |
| Myocardial infarction (MI) |
| ventricular tachycardia/ventricular fibrillation (VT/VF) |

The computed SCA Risk Score (S) is then compared S815 against a user-defined risk score threshold (T). If S is less than T, the at least one processor 218 continues to receive S805 patient ECG signals for analysis. If S is greater than T, the processor prompts S820 a notification to wear the second wearable portion 215.

In implementations, computing the SCA Risk Score (S) associated with estimating a risk of a potential cardiac arrhythmia event for the patient includes applying the sets of ECG metrics and patient demographic and clinical data to one or more machine learning classifier models. In some implementations, a machine learning classifier can be trained on a large population, for example, a population that can range from several thousand to tens of thousands of patient records comprising electrophysiology, demographic and medical history information. The machine learning tool can include but is not limited to classification and regression tree decision models, such as random forest and gradient boosting, (e.g., implemented using R or any other statistical/mathematical programming language). Any other classification based machine learning tool can be used, including neural networks and support vector machines. Because the machine learning tool may be computationally intensive, some or all of the processing for the machine learning tool may be performed on a server that is separate from the medical device. Examples of risk prediction methods and classifiers are described in, for example, U.S. Publication No. US 2016/0135706 entitled "Medical Premonitory Event Estimation," the entire content of which is incorporated herein by reference.

In implementations, the system 200 includes an output device, such as the output device 1216 of the implementation of the controller 220 of FIG. 7, and the notification to wear the second wearable portion 215 is provided via the output device 1216. In implementations the output device 1216 is a display and/or speaker of the controller 220 configured to provide a visible and/or audible alarm. In implementations, the controller 220 includes a speaker for providing an alarm sound and/or spoken instructions alerting the patient to wear the second wearable portion 215. The alarm sound can be unique from an alarm sound indicating imminent treatment and in implementations is provided with increasing volume or frequency depending on the urgency of the predicted SCA. If the at least one processor 218 determines the SCA is likely to occur within two weeks but not imminently, the alarm may be softer and repeated less frequently than a more urgently impending event. For example, if the at least one processor 218 determines the SCA is likely to occur within a week, the notification can include a series of alerts provided at 1 minute increments at a first decibel level. If the processor determines the SCA is likely to occur beyond one week but within two weeks, the series of alerts are provided at 10 minute increments at a second decibel level that equivalent to or quieter than the first decibel level.

The notification can comprise an instruction to connect the at least one conductive wire 242 of the second wearable portion 215 to the controller 220. In implementations, the at least one processor is configured to initiate delivery of a therapeutic shock via the one or more treatment electrodes 214. Accordingly, the one or more treatment electrodes 214 need to be operatively connected to the controller 220. In implementations, the at least one processor 218 can be configured to detect successful connection of the at least one conductive wire 242. In implementations, the at least one processor 218 provides, via the output device, an indication of successful connection of the at least one conductive wire 242 of the second wearable portion 215 to the controller 220. If connection of the at least one conductive wire 242 is not detected within a threshold period of time, the at least one processor 218 provides an audible and/or visible alert to the patient. In implementations, this process repeats until the one or more treatment electrodes 214 of the second wearable portion 215 are operably connected to the controller 220 and available for providing a therapeutic shock to the patient as initiated by the at least one processor 218.

In implementations, the system 200 is configured for use with a remote server, and one or more functions of the at least one processor 218 are performed by the remote server. Additionally, one or more of the ECG metrics, patient demographic and clinical data, and threshold values can be stored on a remote database in communication with and accessible by the remote server. For example, a processor of the remote server can execute the instructions of the SCA Risk Analysis Assessor and provide the output to the at least one processor 218 of the controller 220. Alternatively or additionally, a processor of the remote server can provide the output to a computing device of a physician or caregiver. The computing device can provide an audible and/or visible notification to the physician or caregiver to instruct the patient on wearing the second wearable portion 215.

Figure 9A:
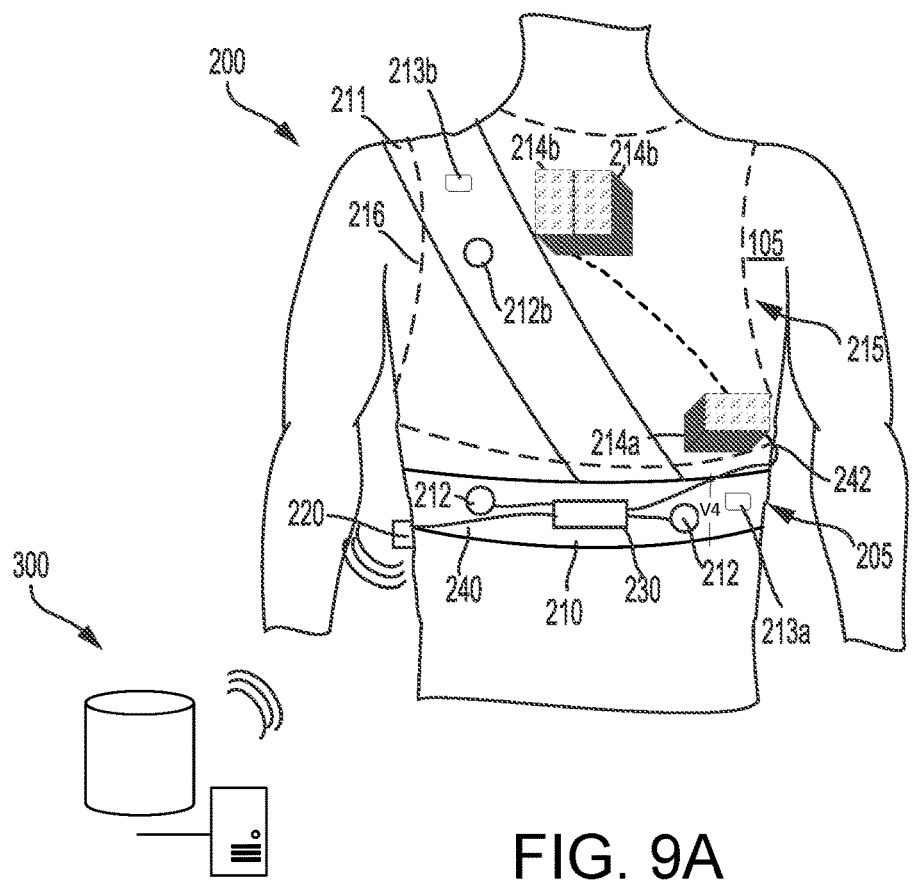
FIG. 9A depicts an embodiment of a patient-worn cardiac monitoring and treatment system comprising a first wearable portion comprising an over the shoulder appendage and a second wearable portion comprising a vest.

In implementations, splitting computation between the controller 220 and a remote server 300 assists with reducing the overall size and construction of the controller 220. As shown in FIG. 9A, the controller 220 can further be reduced in size as compared to the controller of FIGS. 6A and 9B, by distributing controller components throughout the first and second wearable portions 205, 215. As described with regard to FIG. 7 and as will be described in greater detail subsequently, implementations of a wearable cardiac monitoring and treatment system 200 include the controller 220 comprising one or more of the following components: a therapy delivery circuit 1130 including a polarity switching component such as an H-bridge 1228, a data storage 1207, a network interface 1206, a user interface 1208, at least one battery 1140, a sensor interface 1202 that includes, for example, an ECG data acquisition and conditioning circuit, an alarm manager 1214, the at least one processor 218, and one or more capacitors 1135. As shown in FIG. 9A, in implementations, the high voltage components such as the one or more capacitors 1135 and therapy delivery circuit 1130 can be redistributed to the second wearable portion 215. For example, the one or more treatment electrodes 214 can include one or more of these high voltage components. Redistributing these bulkier and heavier components to the second wearable portion 215 reduces the overall size and of the continuously worn controller 220. Because the controller 220 is worn continuously or substantially continuously throughout the duration of wear of the system 200 and because the second wearable portion 215 is worn only when an SCA Risk Assessment Score (S) exceeds a threshold (T), the heavier portions are only worn when necessary. This further assists with overall patient comfort and encourages patient compliance with wearing the first wearable portion 205 for the prescribed duration of wear.

In implementations, as shown in the timeline of FIG. 8B, the cumulative duration of wear 850 of the first wearable portion 205 is equal to or greater than the cumulative duration of wear 852a, 852b of the second wearable portion 215 because the second wearable portion 215 is worn only when the patient is prompted by the system 200. Although a physician may prescribe the system 200 for a duration of wear 850, only the first wearable portion 205, the monitoring portion, need be worn continuously throughout that prescribed duration of wear 850. As shown on the example timeline of FIG. 8B, the patient is not wearing the second wearable portion during an initial span 851 beginning at the start of the duration of wear 850 and lasting until S>T, about a week and a half past the one month mark. The second wearable portion 215 is worn when an SCA Risk Score (S) exceeds a threshold (T), but because the monitoring is continuous, the at least one processor 218 may detect an improvement in the patient's condition. In implementations, if the SCA Risk Score (S) improves during the prescribed duration of wear of the first wearable portion 205 so that S is less than T, the at least one processor 218 can notify the patient to remove the second wearable portion 215. For example, in the timeline of FIG. 8B, the SCA risk analysis assessor outputs S<T about one and a half weeks past the second month mark. In implementations, the at least one processor 218 calculates a wait period 853 of about another 1-2 weeks and continues computing the SCA Risk Score (S) for the duration of the wait period 853 to ensure the patient's condition is stable. At the end of the wait period, the at least one processor 218 can provide a notification that the patient may remove the second wearable portion 215 during a second period 854 of not wearing the second wearable portion 215 because S has remained less than T. In implementations, S must remain less than T without fluctuation and within a user defined tolerance range (e.g. 5% or more less the threshold T) during the wait period 853 in order for the at least one processor 218 to provide a notification to remove the second wearable portion 215. In this example, the at least one processor 218 computes an SCA Risk Score S greater than T at month 4 and again prompts a notification to wear the second wearable portion 215. Because monitoring and analysis is continuous throughout the duration of wear 850, the SCA Risk Score S may remain greater that T until the end of the prescribed duration of wear 850, at which time the physician or caregiver may re-evaluate treatment options for the patient. The system 200 therefore continuously monitors the patient's physiological condition and protects the patient from harm while also accounting for patient comfort by avoiding unnecessary wear of the second wearable portion 215.

Patient comfort is also achieved by customizing one or more features of the elongated strap 210 for each patient's preferences and body morphology. Returning to FIGS. 6A-B, the elongated strap 210 can be sized to fit about the thoracic region 105 of the patient by matching the length the elongated strap 210 to one or more circumferential measurements of the thoracic region 105 during an initial fitting. For example, in an initial fitting, a caregiver, physician or patient service representative (PSR) can measure the circumference of the thoracic region 105 of the patient at one or more locations disposed about the thoracic region 105 between about the T1 thoracic region and the T12 thoracic region, and select an elongated strap 210 having a length L2 within a range of 2-25% longer than the largest measured circumference. For example, the strap 210 can be configured to be worn within a T5 thoracic vertebra region and a T11 thoracic vertebra region. For example, t the strap 210 can be configured to be worn within a T8 thoracic vertebra region and a T10 thoracic vertebra region. Having the elongated strap 210 be longer than the largest measured circumference of the thoracic region 105 can provide comfort advantages of loosening and tightening the elongated strap 210 to accommodate fluctuations in body mass throughout the prescribed duration of wear. Additionally, in embodiments of the system 200 having a fastener 247 configured to secure the elongated strap 210 about the thoracic region 105, the patient can loosen or reposition the elongated strap 210 around one or more positions along the thoracic region 105 between about the T1 thoracic region and T12 thoracic region. In implementations, at least one fastener 247 is disposed on a first end 245a of the elongated strap 210 for adjoining a second end 245b of the elongated strap 210 in secured attachment about the thoracic region 105 of the patient. In implementations, the fastener 247 is an adjustable latching mechanism configured to secure and tighten the elongated strap 210 about the thoracic region 105 of the patient.

Figure 9B:
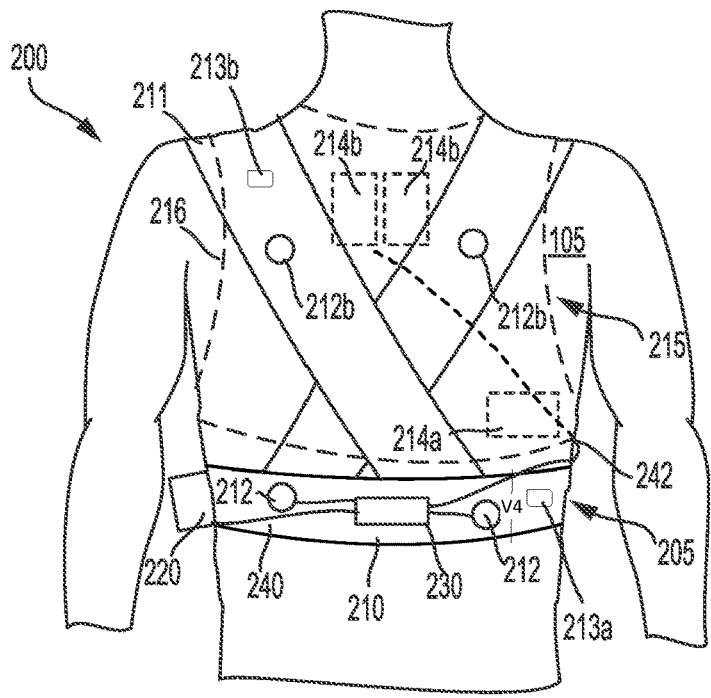
FIG. 9B depicts an embodiment of a patient-worn cardiac monitoring and treatment system comprising a first wearable portion comprising two over the shoulder appendages and a second wearable portion comprising a vest.

Additionally or alternatively, the elongated strap 210 or other support elements of preceding and subsequently described implementations, such as appendages 111 of FIG. 2A and 211 of FIGS. 9A-B, and sash 410 of FIG. 14, can have proportions and dimensions derived from patient-specific thoracic 3D scan dimensions so as to provide conformally fitted support elements shaped to fit the particular patient's exact body shape, thereby providing a much higher degree of comfort than an off-the-shelf garment. The 3D scan dimensions may be generated from a three dimensional imaging system such as a 3D surface imaging technology with anatomical integrity, for instance the 3dMDthorax System by 3dMD LLC, Atlanta GA.

The three-dimensional imaging system can comprise one or more of a digital camera, RGB camera, digital video camera, red-green-blue sensor, and/or depth sensor for capturing visual information and static or video images of the rescue scene. In some examples, the three-dimensional imaging system can comprise both optical and depth sensing components as with the Kinect motion sensing input device by Microsoft, or the Apple TrueDepth 3D sensing system which may include an infrared camera, flood illuminator, proximity sensor, ambient light sensor, speaker, microphone, 7-megapixel traditional camera, and dot projector (which projects up to 30,000 points on an object during a scan).

The patient-specific thoracic 3D scan dimensions can be input into custom-tailoring software such as ACCUMARK MADE-TO-MEASURE and ACCUMARK 3D by Gerber Technology of Tolland, CT, or EFI Optitex 2D and 3D integrated pattern design software by EFI Optitex of New York, NY The dimensions as well as three-dimensional surfaces can also be input into a 3D printer such as the FORMLABS FORM 3L 3D printer (by Formlabs of Somerville, MA) using the FORMLABS elastic resin to generate strap or other support elements that conform to the patient's body shape. The elastic resin comprises a shore durometer of between about 40A-80A (e.g. 40A, 45A, 50A, 55A, 60A, 65A, 70A, 75A, 80A).

From a 3-dimensional scan of the thoracic region 105 of the patient, an elongated strap 210 or other support element can be sized to fit proportions and dimensions of the thoracic region 105 in a nested fit that conforms to the specific patient's body shape. In implementations, for example, various body size measurements and/or 3D images may be obtained of at least a portion of the patient's body, and one or more portions of the elongated strap 210 or other support element can be formed of a plastic, polymer, or woven fabric to have contours accommodating one or more portions of the thoracic region, or other anatomical region such as arms, neck, etc. conforming to the specific patient's body shape. For example one or more portions of the elongated strap 210 or other support element may be 3D printed from, for example, any suitable thermoplastic (e.g., ABS plastic) or any elastomeric and/or flexible 3D printable material. For example the elongated strap 210 may include at least two curved rigid or semi-rigid portions for engaging the patient's sides, under the arms. The at least two curved portions add rigid structure that assists with preventing the elongated strap 210 from shifting or rotating about the thoracic region. This stability provides consistency of sensor signal readings and prevents noise associated with sensor movement.

As described previously with regard to the embodiments of FIGS. 2A-B, in implementations, the elongated strap 210 comprises at least one visible indicator 249 of elongated strap 210 tension disposed on a surface of the elongated strap 210. For example, the visible indicator 249 can be a color changing indicator incorporated in the elongated strap 210 indicating whether the elongated strap 210 is too loose, overtightened, or compressed within the range of compressive forces. As the elongated strap 210 stretches, the material forming the visible indicator 249, for example, can change color between blue, indicating over-tensioning or under-tensioning, and yellow or green, indicating proper tensioning for simultaneously enabling sensor readings and patient comfort. In one implementation, the visible indicator 249 can comprise one or more stretchable, multilayer smart fibers disposed in or on the elongated strap 210. The one or more smart fibers change color from red, to orange, to yellow, to green and to blue as strain on the fiber increases. Providing a visible indication directly on the elongated strap 210 enables a patient to adjust or reapply the strap 210 so that the plurality of ECG sensing electrodes 212 and the one or more treatment electrodes 214 are properly positioned and immobilized on the thoracic region 105 and so that the strap 210 isn't overtightened and applying compressive forces in the thoracic region 105 to a level of patient discomfort. In other implementations, the elongated strap 210 can include a mechanical strain gauge in or on the elongated strap 210. The mechanical strain gauge can be communicatively coupled to the plurality of conductive wires 240 such that the controller 220 provides an audible and/or visible indication of whether the elongated strap 210 is over-tightened, too loose, or within the range of compression forces enabling effective use and wear comfort.

In implementations, the elongated strap 210 comprises an unbroken loop comprising a stretchable fabric. The elongated strap 210 can be configured to stretch over the shoulders or hips of the patient and contract when positioned about the thoracic region 105. In implementations, the stretchable fabric comprises at least one of nylon, LYCRA, spandex, and neoprene. During an initial fitting, the physician, caregiver, or PSR can select an elongated strap 210 sized to fit the patient. For example, the physician, caregiver, or PSR can measure a circumference about one or more locations of the thoracic region 105. The physician, caregiver, or PSR can select an elongated strap 210 having a circumference within about 75% to about 95% of the measurement of the one or more locations about the thoracic region 105. In some implementations, the elongated strap 210 comprises an elasticized thread. In some implementations, the elongated strap 210 comprises an elasticized panel disposed in the elongated strap 210, the elasticized panel comprising a portion of the elongated strap 210 spanning less than a total length of the elongated strap 210. For example, the elongated strap 210 can include one or more mechanically joined sections forming a continuous length L2 or unbroken loop. The one of the one or more sections can comprise a stretchable fabric and/or elasticized thread interspersed with non-stretchable or relatively less stretchable portions. In other embodiments, the elongated strap 210 can include a compression an adjustable tension element, such as one or more cords disposed in the elongated strap 210 and configured to be tensioned and held in tension by one or more pull stops. In all embodiments, the elongated strap 210 can include one or more visible or mechanical tension indicators configured to provide a notification of the elongated strap 210 exerting compression forces against the thoracic region 105 in a range from 0.025 psi to 0.75 psi.

In implementations, the elongated strap 210 comprises a breathable, skin-facing layer including at least one of a compression padding, a silicone tread, and one or more textured surface contours. The breathable material and compression padding enable patient comfort throughout the duration of wear and the silicon tread and/or one or more surface contours assist with immobilizing the elongated strap 210 relative to the skin surface of the thoracic region.

Implementations of the elongated strap 210 in accordance with the present disclosure may exhibit a moisture vapor transmission rate (MVTR) of, for example, between about 600 g/m$^2$/day and about 1,400 g/m$^2$/day when worn by a subject in an environment at room temperature (e.g., about 25° C.) and at a relative humidity of, for example, about 70%. In implementations, the elongated strap 210 has a water vapor permeability of 100 g/m$^2$/24 hours, as measured by such vapor transmission standards of ASTM E-96-80 (Version E96/E96M-13), using either the "in contact with water vapor" ("dry") or "in contact with liquid" ("wet") methods. Such test methods are described in U.S. Pat. No. 9,867,976, titled "LONG-TERM WEAR ELECTRODE," issued on Jan. 16, 2018 (hereinafter the "'976 Patent"), the disclosure of which is incorporated by reference herein in its entirety. In implementations, the elongated strap 210 comprises one or more moisture wicking fabrics for assisting with moving moisture away from the skin of the thoracic region 105 and improving patient comfort throughout the prescribed duration of wear.

In implementations, the elongated strap 210 includes low skin-irritation fabrics and/or adhesives. In embodiments, the elongated strap 210 may be worn continuously by a patient for a long-term duration (e.g., duration of at least one week, at least 30 days, at least one month, at least two months, at least three months, at least six months, and at least one year) without the patient experiencing significant skin irritation. For example, a measure of skin irritation can be based on skin irritation grading of one or more as set forth in Table C.1 of Annex C of American National Standard ANSI/AAMI/ISO 10993-10:2010, reproduced above in Table 1.

Figure 10A:
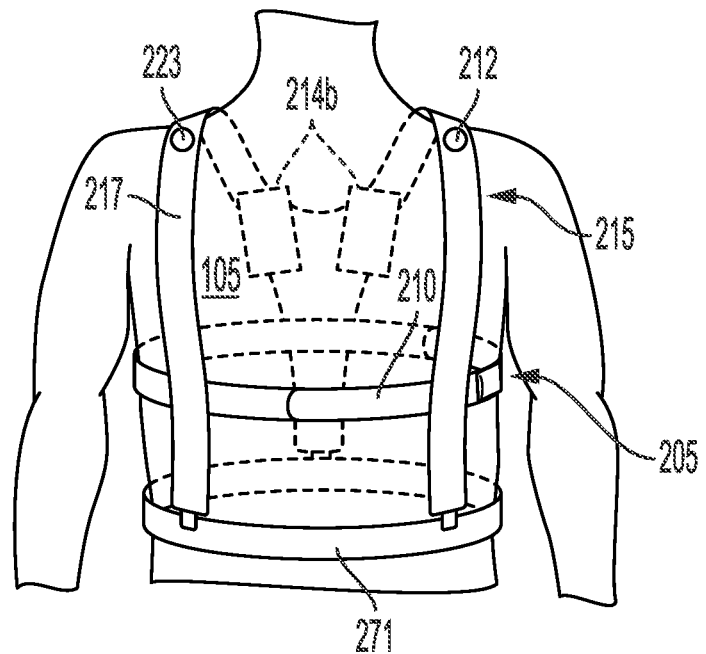
FIG. 10A depicts an embodiment of a patient-worn cardiac monitoring and treatment system comprising a first wearable portion comprising a strap and a second wearable portion comprising suspenders.
Figure 10B:
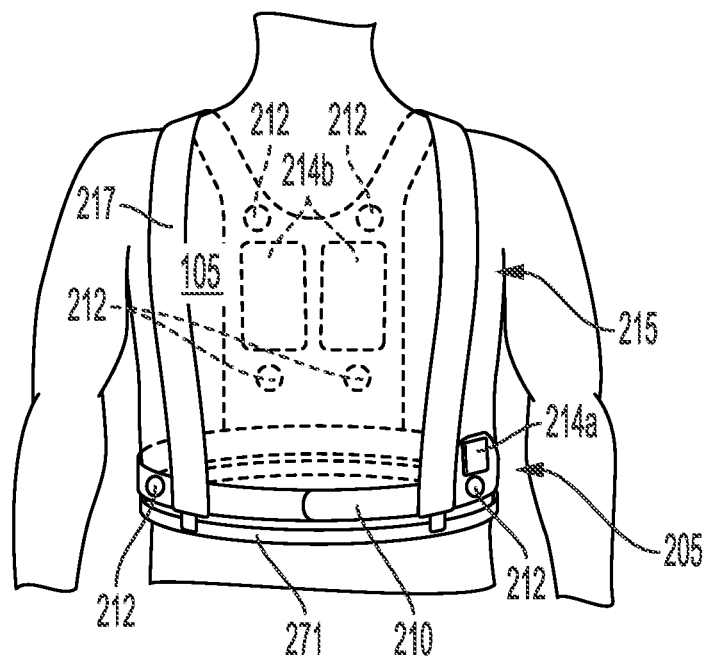
FIG. 10B depicts an embodiment of a patient-worn cardiac monitoring and treatment system comprising a first wearable portion comprising a strap and a second wearable portion comprising suspenders.
Figure 11A:
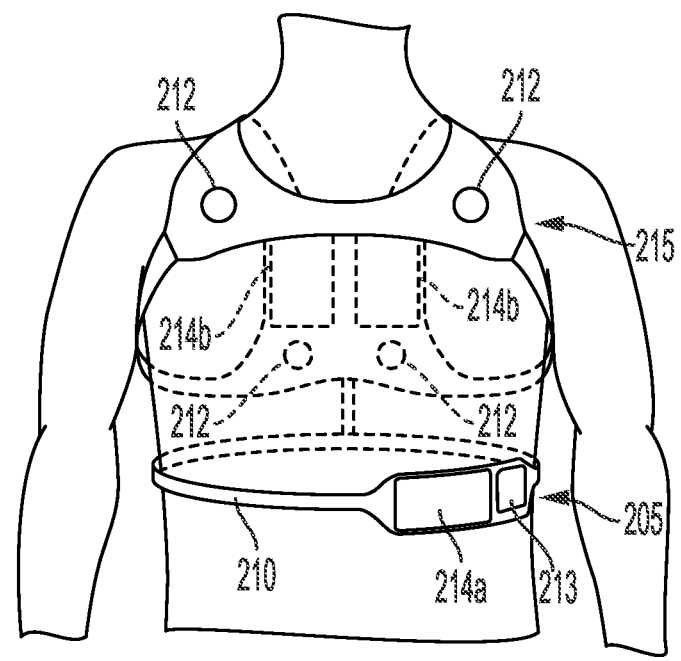
FIG. 11A depicts an embodiment of a patient-worn cardiac monitoring and treatment system comprising a first wearable portion comprising a strap and a second wearable portion comprising a holster.
Figure 11B:
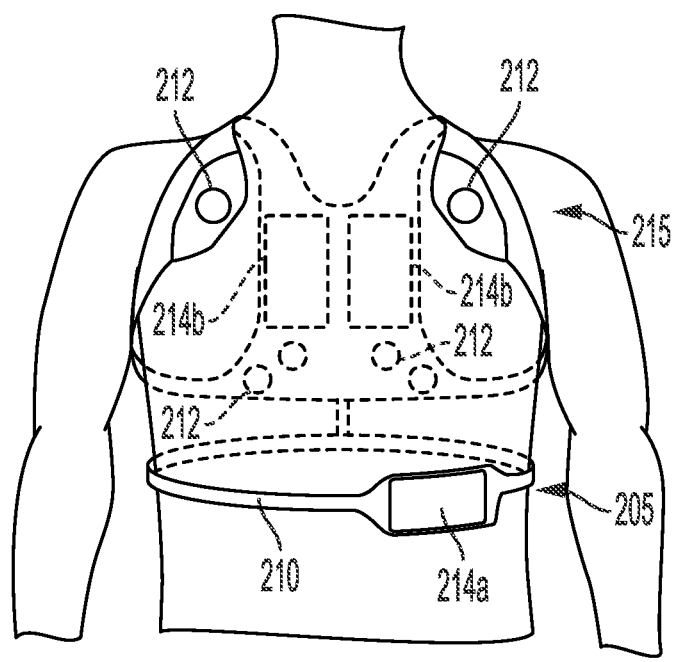
FIG. 11B depicts an embodiment of a patient-worn cardiac monitoring and treatment system comprising a first wearable portion comprising a strap and a second wearable portion comprising a holster.
Figure 12A:
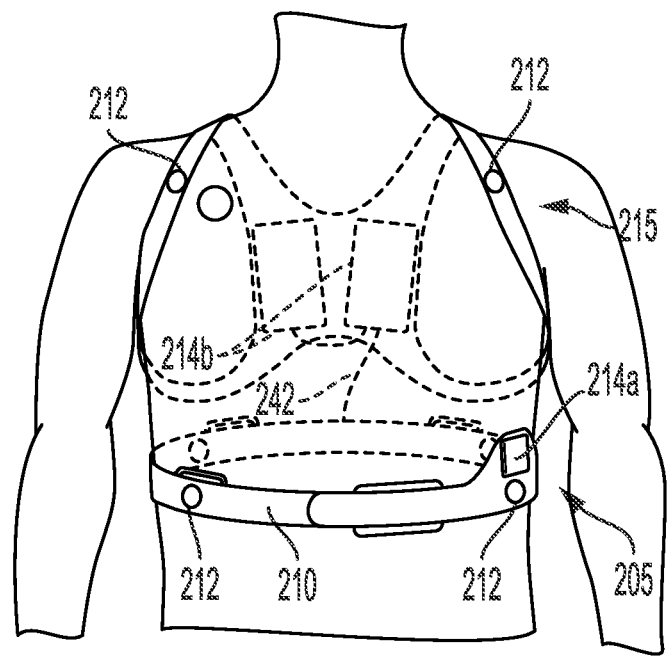
FIG. 12A depicts an embodiment of a patient-worn cardiac monitoring and treatment system comprising a first wearable portion comprising a strap and a second wearable portion comprising a butterfly harness.
Figure 12B:
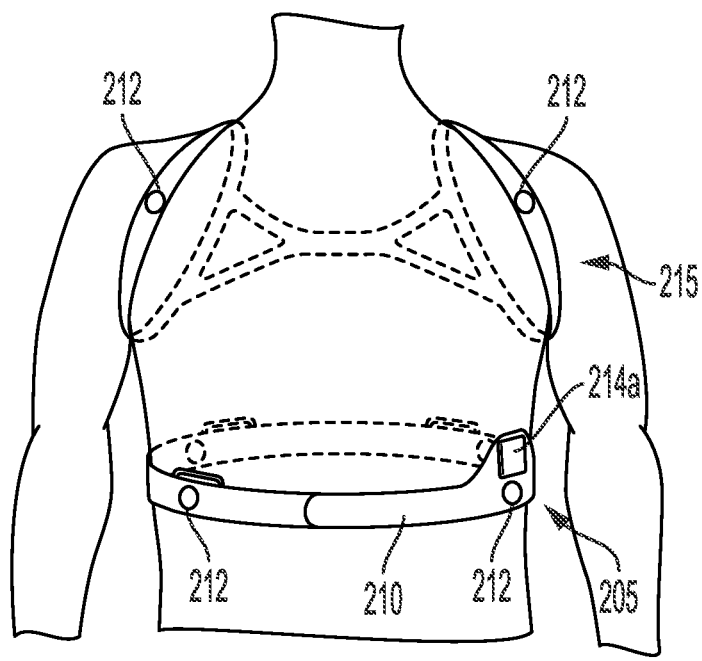
FIG. 12B depicts an embodiment of a patient-worn cardiac monitoring and treatment system comprising a first wearable portion comprising a strap and a second wearable portion comprising a butterfly harness.
Figure 13:
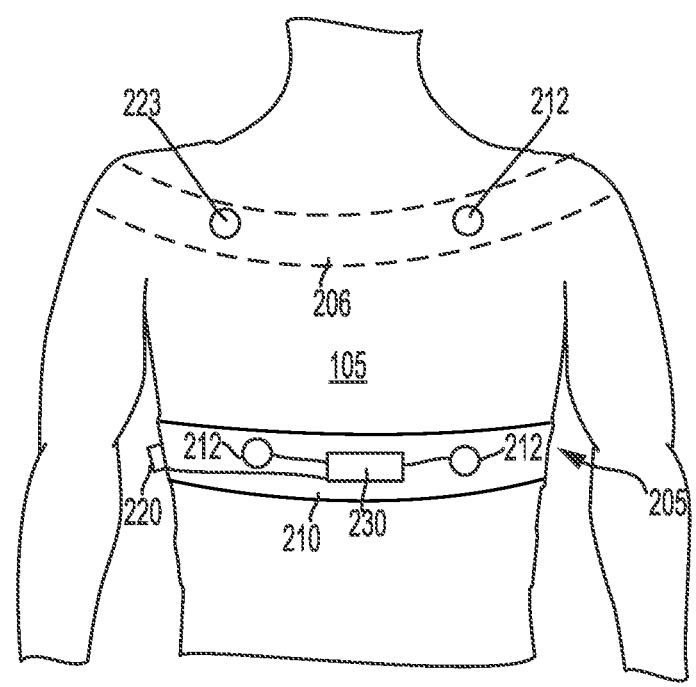
FIG. 13 depicts an embodiment of a patient-worn cardiac monitoring and treatment system comprising a first wearable portion comprising a strap and a yoke.

The second wearable portion 215 similarly can comprise or consist of low skin irritation fabrics. Additionally, the substrate 216 of second wearable portion 215 can be lightweight and less compressive than the elongated strap 210 of the first wearable portion 205. In implementations, such as those of FIGS. 6A-B and 9A-13B, the second wearable portion 215 comprises at least one of a shirt, a vest, a bandeau, a pinnie, a butterfly harness, a yoke, and a dickie. The first and second wearable portions 205, 215 are configured to be worn beneath a clothing of the patient. By maintaining and minimizing the substrate 216 of the second wearable portion 215, the system 200 further minimizes patient discomfort and visibility of the system 200 when worn beneath outer garments (e.g., the patient's clothing). For example, as shown in the implementation of FIGS. 10A-B, the second wearable portion 215 can comprise a belt 271 and suspenders 217 for supporting one or more treatment electrodes 214 and one or more additional sensors, such as a p-wave sensor 223 located on an upper half of the thoracic region 105. In implementations, as shown in FIGS. 11A-B, the second wearable portion 215 can be a holster worn about the armpits and supported by the patient's shoulders. In implementations, as shown in FIGS. 12A-B, the second wearable portion 215 can be a butterfly harness worn about the armpits and supported by the patient's shoulders.

Additionally or alternatively, in implementations, the first wearable portion 205 and/or the second wearable portion 215 can include additional sensors and in implementations, one or both of the first wearable portion 205 and second wearable portion 215 can include various structural elements for supporting one or more additional sensors of the system 200. For example, the first wearable portion 205 further can include an appendage 211 mechanically attached to the elongated strap 210. In implementations, the appendage is a flap, similar to the anterior and posterior appendages 150, 155 of FIGS. 2A-B. In implementations, as shown in FIGS. 6A and 9A the appendage 211 is an over-the-shoulder sash. In implementations, as shown in FIG. 9B, the appendage 211 is a pair of over-the shoulder sashes crossing over the anterior area of the thoracic region 105. In implementations, the appendage 211 is monolithically formed with the elongated strap 210 and therefore non-separable from the elongated strap 210. In implementations, the appendage 211 is configured to be affixed to the elongated strap 210. The appendage 211 can be affixed to the elongated strap by permanent fasteners, such as, for example rivets, stitches, heat welds, and adhesives. In other implementations, one or both ends of the appendage 211 can be affixed to the elongated strap 210 by releasable fasteners, such as zippers, hook and loop fasteners, buttons, and snaps. The appendage 211 can be adjustable in length and can comprise a stretchable fabric to hold the appendage 211 in compression against the thoracic region 105. For example, the appendage 211 can comprise a fabric comprising or consisting of an elastic polyurethane fiber that provides stretch and recovery. For example, the fabric may comprise or consist of at least one of neoprene, spandex, nylon-spandex, nylon-LYCRA, ROICA, LINEL, INVIYA, ELASPAN, ACEPORA, and ESPA. In implementations, the appendage 211 can be optionally affixed to the elongated strap to provide additional functionality as prescribed by a physical and/or to provide the patient an opportunity to remove, launder, swap out, and/or replace the appendage 211. For example, if the appendage 211 starts to stretch and loosen, the patient may prefer to remove the appendage 211 and don a new, more taught replacement.

In implementations, the appendage 211 is configured to be continuously worn about the thoracic region 105 of the patient and comprises at least one additional ECG sensing electrode 212b in communication with the plurality of conductive wires 240 of the elongated strap 210. The at least one additional ECG sensing electrode 212b is configured to sense the ECG signal of the patient in conjunction with the plurality of ECG sensing electrodes 212 of the elongated strap 210. As previously described with regard to the device of FIG. 5, an appendage 111 comprises at least one treatment electrode 114b in communication with the at least one processor, the at least one treatment electrode 114b configured to provide a therapeutic shock. In such an implementation, the at least one treatment electrode 114b is in wired communication with the plurality of conductive wires of the band 110. Similarly, the appendage 211 of FIGS. 9A-B can include at least one of one or more permanently affixed and/or selectively added additional treatment electrodes, additional ECG sensing electrodes 212b, p-wave sensors, and other physiological sensors. In the implementations of FIGS. 9A-9B, for example, the appendage 211 comprises thereon an additional ECG sensing electrode 212b positioned in an upper anterior region of the thoracic region 105, such that the at least one processor 218 can monitor a standard ECG signal lead. Additionally, in the implementations of FIGS. 9A-9B the appendage includes one or more receiving ports 213a-b configured to receive one or more additional sensors. The additional one or more sensors can be, for example, one or more physiological sensors for detecting one or more of pulmonary vibrations (e.g., using microphones and/or accelerometers), breath vibrations, sleep related parameters (e.g., snoring, sleep apnea), and tissue fluids (e.g., using radio-frequency transmitters and sensors). The one or more additional sensors of the appendage 211 can be, for example, one or more physiological sensors including a pressure sensor for sensing compression forces of the garment, SpO2 sensors, blood pressure sensors, bioimpedance sensors, humidity sensors, temperature sensors, and photoplethysmography sensors. In some examples, the one or more receiving ports 213a-b can also be configured to receive one or more motion and/or position sensors. For example, the additional one or more sensors can be motion sensors including accelerometers for monitoring the movement of the patient's torso in x-, y- and z-axes to determine a movement of the patient, gait, and/or whether the patient is upright, standing, sitting, lying down, and/or elevated in bed with pillows. In certain implementations, one or more gyroscopes may also be provided to monitor an orientation of the patient's torso in space to provide information on, e.g., whether the patient is lying face down or face up, or a direction in which the patient is facing.

In the implementation of FIGS. 10A-B, the one or more additional sensors can be supported by the second wearable portion 215. For example, the suspenders 217 of the second wearable portion of FIG. 10A have disposed thereon an ECG sensor 212 and a p-wave sensor 223 located in an upper anterior portion of the thoracic region for optimal positioning for sensor readings. Similarly, the implementations of the second portion 215 of FIGS. 10B-12B include one or more additional sensors, including at least an ECG sensing electrode 212.

As previously described the first wearable portion 205 is continuously worn or substantially continuously worn about the thoracic region 105 throughout the prescribed duration of wear. In some implementations, such as that of FIG. 13, the monitoring portion of the system 200 can include a first wearable portion 205 including an elongated strap 210 as described previously in embodiments and a second, separate strap 206 configured to be draped around the upper portion of the thoracic region 105. The separate strap 206 is configured to support one or more addition sensors such as a p-wave sensor 223 and an additional ECG sensing electrode 212 configured to detect an ECG signal of the patient in conjunction with the one or more ECG sensing electrodes of the elongated strap 210. This second strap 206 provides optimal placement of the additional sensors for detecting or more conditions of the patient without the use of potentially irritating adhesives.

While the first wearable portion 205 can provide, in implementations, various combinations of physiological sensors, in other implementations, the device can be a unitary wearable device include all sensing and treatment sensors. Similar to the device 100 of FIGS. 2A-2B, the cardiac monitoring and treatment device 400 of FIG. 14 includes a continuously worn, cross-body sash 410 worn over a shoulder of a patient and around an opposite side of the patient. In implementations, the sash 410 is configured to be worn over a shoulder of a patient, encircling a thoracic region 105, extending from over the first shoulder of the patient across an anterior area of the thoracic region 105 to an opposite lateral side of the thoracic region 105 under the second shoulder of the patient adjacent to the axilla, and further extending across a posterior area of the thoracic region 105 from under the second shoulder to over the first shoulder. The device 400 comprises a plurality of electrodes and associated circuitry disposed about the sash 410. The plurality of electrodes can include at least one pair of sensing electrodes 412 disposed about the sash 410 and configured to be in electrical contact with the patient. The at least one pair of sensing electrodes 412 can be configured to detect one or more cardiac signals such as ECG signals. An example ECG sensing electrode 412 includes a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference. The device 400 can include an ECG acquisition circuit in communication with the at least one pair of ECG sensing electrodes 412 and configured to provide ECG information for the patient based on the sensed ECG signal. In implementations, the at least one pair of sensing electrodes can include a driven ground electrode, or right leg drive electrode, configured to ground the patient and reduce noise in the sensed ECG signal.

The plurality of electrodes can include at least one pair of treatment electrodes 414a and 414b (collectively referred to herein as treatment electrodes 414) coupled to a treatment delivery circuit. The at least one pair of treatment electrodes 414 can be configured to deliver an electrotherapy to the patient. For example, one or more of the at least one pair of treatment electrodes 414 can be configured to deliver one or more therapeutic defibrillating shocks to the body (e.g., the thoracic region 105) of the patient when the medical device 100 determines that such treatment is warranted based on the signals detected by the at least one pair of ECG sensing electrodes 412 and processed by the medical device controller 420. Example treatment electrodes 414 include, for example, conductive metal electrodes such as stainless steel electrodes that include, in certain implementations, one or more conductive gel deployment devices configured to deliver conductive gel to the metal electrode prior to delivery of a therapeutic shock. In implementations, a first one of the at least one pair of treatment electrodes 414a is configured to be located within an anterior area of the thoracic region 105 and a second one of the at least one pair of treatment electrodes 414b is configured to be located within a posterior area of the thoracic region 105 of the patient. In some implementations, the anterior area can include a side area of the thoracic region 105.

In some examples, at least some of the plurality of electrodes and associated circuitry of the device 100 can be configured to be selectively affixed or attached to the sash 410 which can be worn about the patient's thoracic region 105. In some examples, at least some of the plurality of electrodes and associated circuitry of the device 400 can be configured to be permanently secured into the sash 410. In implementations, the plurality of electrodes are manufactured as integral components of the sash 410. For example, the at least one pair of treatment electrodes 414 and/or the at least one pair of ECG sensing electrodes 412 can be formed of the warp and weft of a fabric forming at least a layer of the sash 410. In implementations, the at least one pair of treatment electrodes 414 and at least one pair of ECG sensing electrodes 412 are formed from conductive fibers that are interwoven with non-conductive fibers of the fabric.

In implementations, the device 400 includes a controller 420 including an ingress-protected housing, and a processor disposed within the ingress-protected housing. The processor is configured to analyze the ECG information of the patient from the ECG acquisition circuit and detect one or more treatable arrhythmias based on the ECG information, and cause the treatment delivery circuit to deliver the electrotherapy to the patient on detecting the one or more treatable arrhythmias. The medical device controller 420 can be operatively coupled to the at least one pair of ECG sensing electrodes 412, which can be affixed to the sash 410. In embodiments, the at least one pair of ECG sensing electrodes 412 are assembled into the sash 410 or removably attached to the garment, using, for example, hook and loop fasteners, thermoform press fit receptacles, snaps, and magnets, among other restraints. In some implementations, as described previously, at least one pair of ECG sensing electrodes 412 can be a permanent portion of the sash 410. The medical device controller 420 also can be operatively coupled to the at least one pair of treatment electrodes 414. For example, the at least one pair of treatment electrodes 414 can also be assembled into the sash 410, or, as described previously, in some implementations, the at least one pair of treatment electrodes 414 can be a permanent portion of the sash 410. Optionally, the device can include a connection pod 430 in wired connection with one or more of the plurality of electrodes and associated circuitry. In some examples, the connection pod 430 includes at least one of the ECG acquisition circuit and a signal processor configured to amplify, filter, and digitize the cardiac signals prior to transmitting the cardiac signals to the medical device controller 420. In implementations, the device 400 can include at least one ECG sensing electrode 412 configured to be adhesively attached to the upper portion of the thoracic region 105, above the sash 410, the at least one pair of ECG sensing electrodes 412 being in wired communication with the ECG acquisition circuitry and at least one of the connection pod and the controller 420.

In implementations, the device includes a conductive wiring 440 configured to communicatively couple the controller 420 to the plurality of electrodes and associated circuitry disposed about the sash 410. In implementations, the conductive wiring 440 can be woven into the warp and weft of the fabric. In implementations, the conductive wiring 440 can be integrated into the fabric, disposed between layers of the sash. In implementations, the conductive wiring 440 can include one or more conductive threads integrated into the fabric of the sash 410. In examples, the one or more conductive threads can be integrated in a zigzag or other doubled back pattern so as to straighten as the sash 410 stretches. The zigzag or doubled-back pattern therefore accommodates for stretching and patient movement while keeping the one or more conductive threads from contacting the skin of the patient. Integrating the conductive wiring 440 into the sash 410 reduces and/or eliminates snagging the wire or thread on an external object. In other examples, the conductive thread can be routed on an exterior surface of the sash 410 so as to avoid contacting the skin of the patient and therefore avoid irritation associated with such potential contact. In implementations, the conductive wiring 440 includes two or more conductive wires bundled within an insulating outer sheath. In implementations, the conductive wiring 440 can be routed along the sash 410 and held securely to the sash 410 by one or more loops of fabric, closable retention tabs, eyelets and/or other retainers so that the conductive wiring 140.

Similar to the implementation described previously with regard to the device 100 of FIGS. 2A-B, the ingress-protected housing of the controller 420 of the device 400 protects the components thereunder from external environmental impact, for example damage associated with water ingress. Preventing such ingress protects the electronic components of the device 100 from short-circuiting or corrosion of moisture-sensitive electronics, for example, when a patient wears the device while showering. Such features may also protect from other liquid and solid particle ingress. In implementations, the ingress-protected housing of the controller 420 includes at least one ingress-protected connector port 421 configured to receive at least one connector 441 of the conductive wiring 440. The at least one ingress-protected connector port can have an IP67 rating such that the device can be connected to the controller 420 and operable when a patient is showering or bathing, for example.

Additionally, the sash 410 can be water vapor-permeable, and substantially liquid-impermeable or waterproof. In implementations, a portion of the sash 410 comprises a water resistant and/or waterproof fabric covering and/or encapsulating electronic components including, for example, the at least one pair of ECG sensing electrodes 412, the at least one pair of treatment electrodes 414, and the conductive wiring 440, and a portion of the sash 410 comprises a water permeable, breathable fabric having a relatively higher moisture vapor transmission rate that the water resistant and/or waterproof portions. The sash 410 can comprise or consist of at least one of neoprene, spandex, nylon-spandex, nylon-LYCRA, ROICA, LINEL, INVIYA, ELASPAN, ACEPORA, and ESPA. In examples, the sash 410 can comprise or consist of a fabric having a biocompatible surface treatment rendering the fabric water resistant and/or waterproof. For example, the fabric can be enhanced by dipping in a bath of fluorocarbon, such as Teflon or fluorinated-decyl polyhedral oligomeric silsesquioxane (F-POSS). Additionally or alternatively, the sash 410 can comprise or consist of a fabric including anti-bacterial and/or anti-microbial yarns. For example, these yarns can include a base material of at least one of nylon, polytetrafluoroethylene, and polyester. These yarns can be for example, one or more of an antibacterial silver coated yarn, antibacterial DRAYLON DRALON yarn, DRYTEX ANTIBACTERIAL yarn, NILIT BREEZE and NILIT BODYFRESH. In implementations, the outer surface of the sash 410 can comprise one or more patches of an electrostatically dissipative material such as a conductor-filled or conductive plastic in order to prevent static cling of a patient's clothing. Alternatively, in embodiments, the sash 410 comprises a static dissipative coating such as LICRON CRYSTAL ESD Safe Coating (TECHSPRAY, Kennesaw, GA), a clear electrostatic dissipative urethane coating.

In implementations, the sash 410 can include one or more sensor ports 415a-c (collectively referred to as 415) for receiving one or more physiological sensors 423 separate from the at least one pair of ECG sensing electrodes 412. The one or more physiological sensors 423 can be, for example, sensors for detecting one or more of pulmonary vibrations (e.g., using microphones and/or accelerometers), breath vibrations, sleep related parameters (e.g., snoring, sleep apnea), and tissue fluids (e.g., using radio-frequency transmitters and sensors). The one or more additional sensors can be, for example, one or more physiological sensors including a pressure sensor for sensing compression forces of the garment, SpO2 sensors, blood pressure sensors, bioimpedance sensors, humidity sensors, temperature sensors, and photoplethysmography sensors. In some examples, the one or more sensor ports 415 can also be configured to receive one or more motion and/or position sensors. For example, such motion sensors can include accelerometers for monitoring the movement of the patient's torso in x-, y- and z-axes to determine a movement of the patient, gait, and/or whether the patient is upright, standing, sitting, lying down, and/or elevated in bed with pillows. In certain implementations, one or more gyroscopes may also be provided to monitor an orientation of the patient's torso in space to provide information on, e.g., whether the patient is lying face down or face up, or a direction in which the patient is facing.

Returning to FIG. 14, the sash 410 can be sized to fit about the thoracic region 105 of the patient. In implementations, the sash 410 can have proportions and dimensions derived from patient-specific thoracic 3D scan dimensions so as to be conformally fitted and shaped to fit the particular patient's exact body shape, thereby providing a much higher degree of comfort than an off-the-shelf garment. In implementations, sizing the device to fit the patient comprises determining dimensions of the thoracic region 105 in an initial fitting. In implementations, the sash is 3D printed to at least one of body proportions, body shape, body posture, and linear surface measurements of the thoracic region of the patient. In implementations, at least a portion of the sash is 3D printed to conform proportions, dimensions, and shape of the sash to one or more portions and dimensions of the thoracic region 105 and thereby provides a customize, comfort fit to the patient, further encouraging patient compliance with wearing the device 400 throughout the prescribed duration of wear.

In implementations, for example, various body size measurements and/or 3D images may be obtained from the patient, and one or more portions of the sash 410 can be formed of a plastic or polymer to have contours accommodating one or more portions of the thoracic region in a fit that conforms to the specific patient's body shape. A 3D scan can determine, for example, thoracic circumference, lateral width of a patient's chest, contours of the thoracic region, and other relevant physical features of the patient. In implementations, one or more portions of the band may be 3D printed from, for example, any suitable thermoplastic (e.g., ABS plastic) or any elastomeric and/or flexible 3D printable material. In implementations a portion of the sash 410 can be 3D printed to nest with the contours of the patient's shoulder in a comfort fit, like a prosthetic cup sized and shaped to accommodate a limb. The 3D printed shoulder portion remains seated comfortably on the patient's shoulder and assists with preventing the sash 410 from shifting or rotating. In implementations, the sash 410 may include at least two curved rigid or semi-rigid portions for engaging the patient's shoulder and side, under the opposite shoulder. The at least two curved portions add rigid structure that assists with preventing the sash 410 from shifting or rotating about the thoracic region. This stability provides consistency of sensor signal readings and prevents noise associated with sensor movement.

As described previously, during an initial fitting, a physician, caregiver, or PSR can perform a 3D scan of the patient's thoracic region using, for example, three-dimensional imaging systems such as cameras and scanners. For example, imaging system can include a handheld device, such as a handheld digital camera or smart phone, carried by the physician, caregiver, or PSR.

In implementations, a 3D imaging system can include a plurality of conventional digital cameras. Although designs differ from different vendors, as is known in the art, a camera usually comprises a charge-coupled device (CCD) or complementary metal-oxide-semiconductor (CMOS) imaging sensor, a lens, a multifunctional video control chip, and a set of discrete components (e.g., capacitor, resistors, and connectors). An image is recorded by the imaging sensor and can be processed by the video control chip. Captured images can also be processed by, for example, a three-dimensional information and/or image processing module configured to identify anatomical structures, distances, and physical objects contained in the captured images.

In some examples, a camera can include one or more of a digital camera, RGB camera, digital video camera, red-green-blue sensor, and/or depth sensor for capturing visual information and static or video images of the patient. The camera can also comprise multiple image capture features for obtaining stereo images of the thoracic region 105 of the patient. The stereo-image can be processed to determine depth information for physical features of the patient's thoracic region 105.

In other examples, the camera can be a wide angle or fish-eye camera, a three-dimensional camera, a light-field camera, or similar devices for obtaining images. A light-field or three-dimensional camera can refer to an image capture device having an extended depth of field. Advantageously, the extended depth of field means that during image processing, a user can change focus, point of view, or the perceived depth of field of a captured image after the image has been recorded. As such, it has been suggested that an image captured using a light-field or three-dimensional camera contains all information needed to calculate a three-dimensional form of a patient's thoracic region 105. See Christian Perwass, et al. "Single Lens 3D-Camera with Extended Depth-of-Field", Raytrix GmbH, Schauenburgerstr. 116, 24116 Kiel, Germany (2012), which describes an implementation of a light-field 3D camera that may be implemented in embodiments of the present disclosure.

In implementations, 3D information and/or images from a three-dimensional imaging system or sensor can be processed to produce a three-dimensional representation of the thoracic region 105. In some embodiments, the 3D imaging system can be configured to project a grid of markers so as to capture high resolution patient anatomical features. For example, a camera using technology similar to that of the Kinect motion sensing input device provided by Microsoft Corporation may be employed. Such cameras may include a depth sensor employing an infrared laser projector combined with a monochrome CMOS sensor which allows for 3D video data to be captured under ambient light conditions. It can be appreciated that any suitable 3D imaging systems may be used. A 3D representation may be generated by a 3D surface imaging technology with anatomical integrity, for instance the 3dMDthorax System (3dMD LLC, Atlanta GA).

In implementations, a three-dimensional imaging system may be mounted on a tripod facing the patient or handheld by the caregiver such as using an iPhoneX provided by Apple Corporation, which has a built-in three-dimensional imaging system. In implementations, a 3D imaging system can comprise one or more of a digital camera, RGB camera, digital video camera, red-green-blue sensor, and/or depth sensor for capturing visual information and static or video images of the thoracic region 105. In some examples, a 3D imaging system can comprise both optical and depth sensing components as with the Kinect motion sensing input device by Microsoft, or the Apple TrueDepth 3D sensing system which may include an infrared camera, flood illuminator, proximity sensor, ambient light sensor, speaker, microphone, 7-megapixel traditional camera, and dot projector (which projects up to 30,000 points on an object during a scan).

The patient-specific thoracic 3D scan dimensions can be input into custom-tailoring software such as ACCUMARK MADE-TO-MEASURE and ACCUMARK 3D by Gerber Technology of Tolland, CT, or EFI Optitex 2D and 3D integrated pattern design software by EFI Optitex of New York, NY The dimensions as well as three-dimensional surfaces can also be input into a 3D printer such as the FORMLABS FORM 3L 3D printer (by Formlabs of Somerville, MA) using the FORMLABS elastic resin to generate strap or other support elements that conform to the patient's body shape. The elastic resin comprises a shore durometer of between about 40A-80A (e.g. 40A, 45A, 50A, 55A, 60A, 65A, 70A, 75A, 80A).

In addition or alternative to 3D-printing the sash 410 for a custom, nested fit with the morphology of the patient, the sash 410 can also provide a compression fit. In implementations, the sash 410 is configured to exert one or more compression forces against the thoracic region. In implementations, the sash 410 is configured to exert the one or more compression forces in a range from 0.025 to 0.75 psi to the thoracic region 105. For example, the one or more compression forces can be in a range from 0.05 psi to 0.70 psi, 0.075 psi to 0.675 psi, or 0.1 to 0.65 psi. Compression forces of the medical device can be determined, for example, using one or more pressure sensors and systems as described above with regard to the band 110 of FIG. 2A. Immobilizing the sash 410 relative to the skin surface reduces or eliminates sensor signal noise and provides more reliable sensor signals for the processor to analyze the condition of the patient. In implementations, the sash comprises an unbroken loop comprising a stretchable fabric. The sash 410 can be configured to stretch over the shoulders or hips of the patient and contract when positioned about the thoracic region 105. In implementations, the stretchable fabric comprises at least one of nylon, LYCRA, spandex, and neoprene. During an initial fitting, the physician, caregiver, or PSR can select a sash 410 sized to fit the patient. For example, the physician, caregiver, or PSR can measure a circumference about one or more locations on the thoracic region 105. The physician, caregiver, or PSR can select a sash 410 having a circumference within about 75% to about 95% of the measurement of the one or more locations about the thoracic region 105.

In implementations, the sash 410 exerts compression forces against the skin of the patient by one or more of manufacturing all or a portion of the sash 410 from a compression fabric, providing one or more tensioning mechanisms in and/or on the sash 410, and proving a cinching closure mechanism for securing and compressing the sash 410 about the thoracic region 105. In some implementations, the sash 410 comprises an elasticized thread disposed in the sash 410. In some implementations, the sash 410 comprises an elasticized panel spanning less than a total length of the sash 410. For example, the sash 410 can include one or more mechanically joined sections forming a continuous length or unbroken loop. The one of the one or more sections can comprise a stretchable fabric and/or elasticized thread interspersed with non-stretchable or relatively less stretchable portions. In other embodiments, the sash 410 can include an adjustable tension element, such as one or more cables disposed in the sash 410 and configured to be tensioned and held in tension by one or more pull stops. In all embodiments, the sash 410 can include one or more visible or mechanical tension indicators configured to provide a notification of the sash 410 exerting compression forces against the thoracic region 105 in a range from about 0.025 psi to 0.75 psi. For example, the tension indicators can be configured to provide a notification that the compression forces are in a range from 0.05 psi to 0.70 psi, about 0.075 psi to 0.675 psi, or 0.1 psi to 0.65 psi. Compression forces of the medical device can be determined, for example, using one or more pressure sensors and systems as described above with regard to the band 110 of FIG. 2A.

Because the device 400 can be a sash 410 configured to be worn about the thoracic region 105 of the patient, the sash 410 is immobilized by compression forces and unlikely to shift as the patient moves and goes about a daily routine. The sash 410 is immobilized relative to the skin surface of the thoracic region 105 and prevents or eliminates signal noise associated with sensors shifting against the skin. The size and position of the sash 410 also provides a discreet and comfortable device 400 covering only a relatively small portion of the surface area of the entire thoracic region 105 and accommodating a plurality of body types. In implementations, the band comprises a breathable, skin-facing layer including at least one of a compression padding, a silicone tread, and one or more textured surface contours. The breathable material and compression padding enable patient comfort throughout the duration of wear and the silicon tread and/or one or more surface contours assist with immobilizing the sash 410 relative to the skin surface of the thoracic region 105.

Implementations of the device 400 in accordance with the present disclosure may exhibit a moisture vapor transmission rate (MVTR) of, for example, between about 600 g/m$^2$/day and about 1,400 g/m$^2$/day when worn by a subject in an environment at room temperature (e.g., about 25° C.) and at a relative humidity of, for example, about 70%. In implementations, the device 100 has a water vapor permeability of 100 g/m$^2$/24 hours, as measured by such vapor transmission standards of ASTM E-96-80 (Version E96/E96M-13), using either the "in contact with water vapor" ("dry") or "in contact with liquid" ("wet") methods. Such test methods are described in U.S. Pat. No. 9,867,976, titled "LONG-TERM WEAR ELECTRODE," issued on Jan. 16, 2018 (hereinafter the "'976 Patent"), the disclosure of which is incorporated by reference herein in its entirety. In implementations, the sash 410 comprises one or more moisture wicking fabrics for assisting with moving moisture away from the skin of the thoracic region 105 and improving patient comfort throughout the prescribed duration of wear.

Similar to implementations of the device of FIGS. 2A-2B, implementations of the device 400 can optionally include an adhesive configured to secure the sash 410 to the thoracic region 105 of the patient such that the sash 410 is immobile relative to a skin surface of the thoracic region 105. In implementations, the adhesive is removable and/or replaceable and has a low skin irritation grading (e.g., a grading of 1) in accordance with the method set forth in American National Standard ANSI/AAMI/ISO 10993-10:2010, previously described. For example, the adhesive can comprise one or more adhesive patches 424 configured to be disposed between the sash 410 and the skin of the patient. The adhesive patches 424 comprise as pressure-sensitive adhesive having tack, adhesion, and cohesion properties suitable for use with a medical device applied to skin for short term and long-term durations. These pressure sensitive adhesives can include polymers such as acrylics, rubbers, silicones, and polyurethanes having a high initial tack for adhering to skin. These pressure sensitive adhesives also maintain adhesion during showering or while a patient is perspiring. The adhesives also enable removal without leaving behind uncomfortable residue. For example, such an adhesive can be a rubber blended with a tackifier.

In implementations, the adhesive comprises one or more water vapor permeable adhesive patches. Additionally or alternatively, the adhesive can be a conductive patch disposed between the plurality of electrodes and the skin of thoracic region 105, in some implementations. For example, as described in the '976 patent, a water-vapor permeable conductive adhesive patch can be, for example, the flexible, water vapor-permeable, conductive adhesive material can comprise a material selected from the group consisting of an electro-spun polyurethane adhesive, a polymerized microemulsion pressure sensitive adhesive, an organic conductive polymer, an organic semi-conductive conductive polymer, an organic conductive compound and a semi-conductive conductive compound, and combinations thereof. In an example, a thickness of the flexible, water vapor-permeable, conductive adhesive material can be between 0.25 and 100 mils. In another example, the water vapor-permeable, conductive adhesive material can comprise conductive particles. In implementations, the conductive particles may be microscopic or nano-scale particles or fibers of materials, including but not limited to, one or more of carbon black, silver, nickel, graphene, graphite, carbon nanotubes, and/or other conductive biocompatible metals such as aluminum, copper, gold, and/or platinum.

Figure 14:
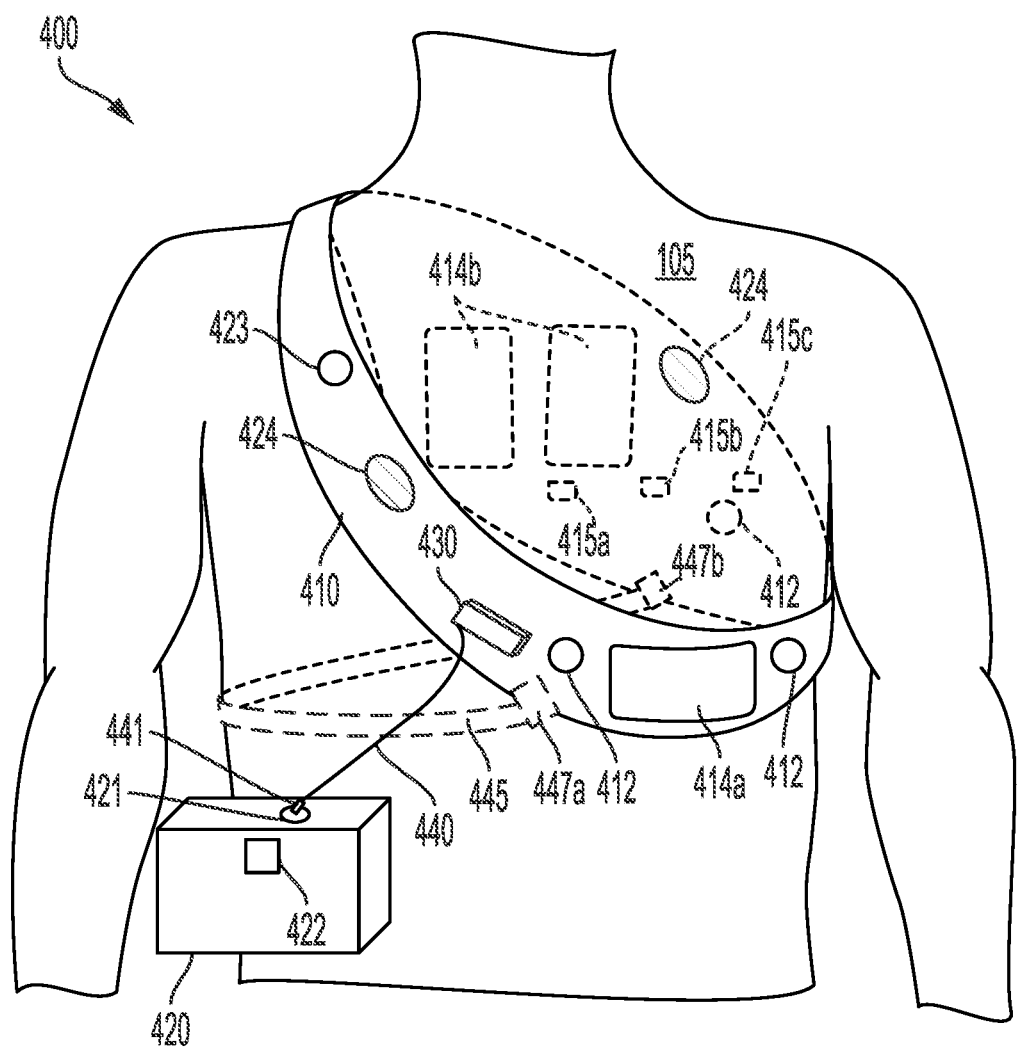
FIG. 14 depicts an embodiment of a patient-worn cardiac monitoring and treatment device comprising a cross-body sash.

In implementations in addition to or alternative to an adhesive, the sash 410 can include an auxiliary strap 445, shown in dashed line in FIG. 14 to indicate optional use. In implementations, a patient optionally may attach the auxiliary strap 445 around the thoracic region. In implementations, the auxiliary strap 445 can attach to an anterior portion of the sash 410 with a connector 447a such as a hook and look fastener, a clip, buttons, or snaps. Similarly, the auxiliary strap 445 can attach to a posterior portion of the sash 410 with a connector 447b such as a hook and look fastener, a clip, buttons, or snaps. The optionally worn auxiliary strap 445 is configured to prevent the sash 410 from shifting and/or rotating. A patient may attach the auxiliary strap 445 during periods of high activity, such as during exercise, and remove the auxiliary strap while seated or prone, such as while sleeping.

As described above, the teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, and other similar wearable medical devices.

A wearable medical cardiac monitoring device is capable of continuous use by the patient. Further, the wearable medical device can be configured as a long-term or extended use medical device. Such devices can be designed to be used by the patient for a long period of time, for example, a period of 24 hours or more, several days, weeks, months, or even years. Accordingly, the long period of use can be uninterrupted until a physician or other caregiver provides specific prescription to the patient to stop use of the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for a long period of at least one year. In some implementations, the extended use can be uninterrupted until a physician or other caregiver provides specific instruction to the patient to stop use of the wearable medical device.

Regardless of the period of wear, the use of the wearable medical device can include continuous or nearly continuous wear by the patient as previously described. For example, the continuous use can include continuous wear of the wearable medical device to the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

In implementations, such as that of FIG. 7, the patient-worn arrhythmia monitoring and treatment device 100 further includes a patient notification output via an output device 1216. In response to detecting one or more treatable arrhythmia conditions, the processor 218 is configured to prompt the patient for a response by issuing the patient notification output, which may be an audible output, tactile output, visual output, or some combination of any and all of these types of notification outputs. In the absence of a response to the notification output from the patient, the processor is configured to cause the therapy delivery circuit 1130 to deliver the one or more therapeutic pulses to the patient.

Figure 15:
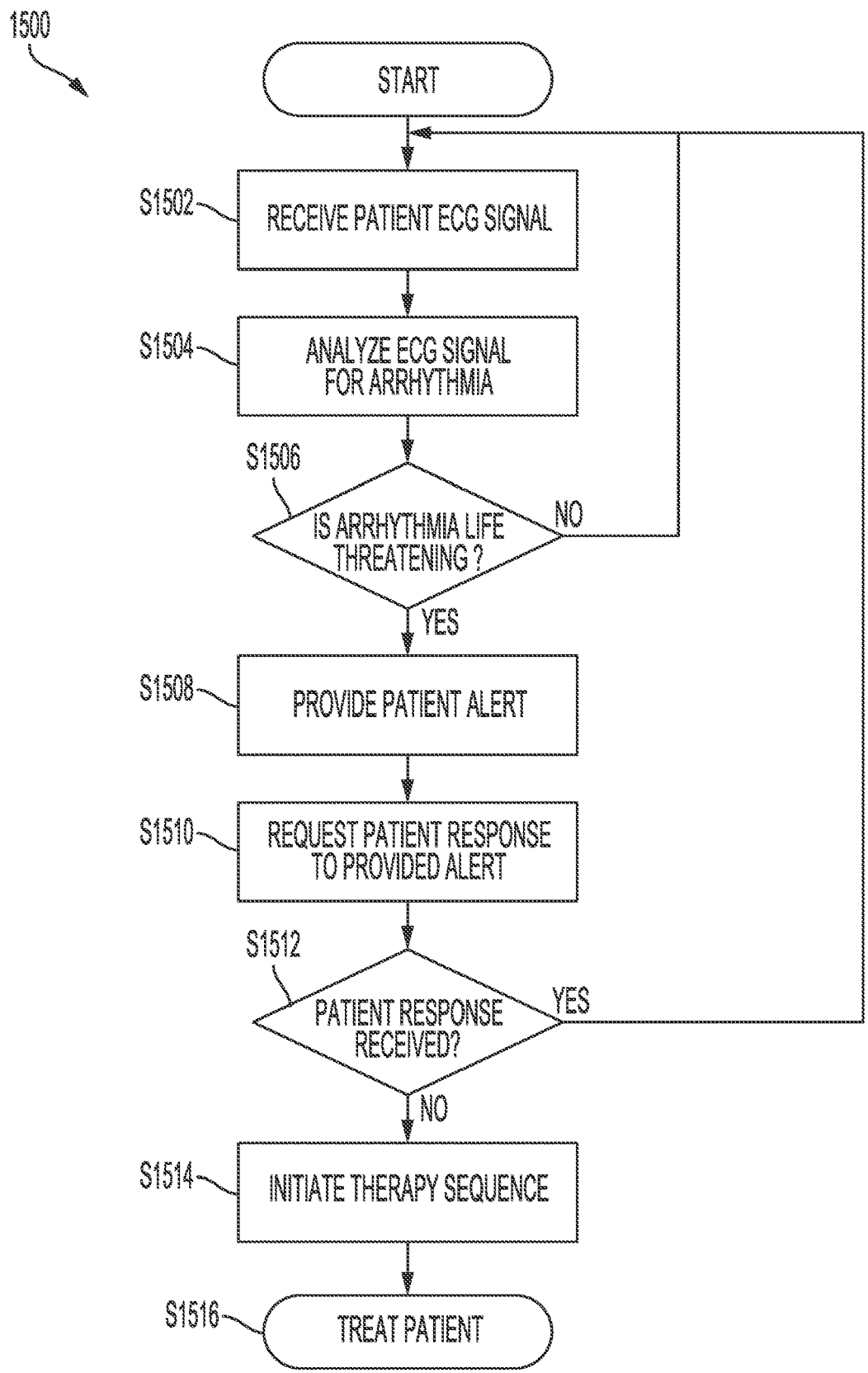
FIG. 15 is a schematic of an example method of using a patient-worn cardiac monitoring and treatment device.

FIG. 15 depicts an example of a process 1500 for determining whether to initiate a therapy sequence and apply a therapeutic pulse to the thoracic region 105 of a patient. In implementations, the processor 218, receives S1502 a patient ECG signal from the ECG sensing electrodes 212 and analyzes S1504 the ECG signal for an arrhythmia condition. The processor 218 determines S1506 whether the arrhythmia is life threatening condition and requires treatment. If the arrhythmia is not life threatening, the processor 218 can cause a portion of the ECG signal to be stored in memory for later analysis and continue to monitor the patient ECG signal. If the arrhythmia is life threatening, the processor 218 provides S1508 a patient notification output and requests S1510 a patient response to the provided notification output. In implementations, the patient responds to an alert by interacting with a user interface (e.g., the user interface 1208 of FIG. 7), which includes, for example, one or more buttons (e.g. the at least one button 122, 422 of the device 100, 400, as shown in FIGS. 2A and 14) or touch screen interface buttons with haptic feedback (e.g., touch screen buttons on the user interface 1208 of the controller 220, 420 and/or a second at least one response button of a wearable article (e.g. an arm band or wrist worn article comprising at least one of a mechanically-actuatable button, a touch screen interface, and at least one touch screen button on a user interface of the wearable article) or like devices, such as smartphones running user-facing interactive applications.). The response may be, for example, pressing one or more buttons in a particular sequence or for a particular duration. The processor 218 determines S1512 whether the patient response was received. If the patient responds to the notification output, the processor 218 is notified that the patient is conscious and returns to a monitoring mode, thereby delaying delivery of a therapeutic defibrillation or pacing shock. If the patient is unconscious and unable to respond to the provided alert, the processor 218 initiates S1514 the therapy sequence and treats S1516 the patient with the delivery of energy to the thoracic region of the patient. In implementations, if a user response button is pressed for longer than a threshold duration (e.g. longer than 5 seconds), the processor 218 instructs the device to prompt the patient to release the button. If the user response button is not released the device will return to a state of imminent therapy delivery and will alert the patient to the imminent shock.

FIGS. 2A-6 and 9A-14 illustrate example cardiac monitoring and treatment devices that are external, ambulatory, and wearable by a patient, and configured to implement one or more configurations described herein. In examples, the medical device can include physiological sensors configured to detect one or more cardiac signals. Examples of such signals include ECG signals and/or other sensed cardiac physiological signals from the patient. In certain implementations, the physiological sensors can include additional components such as accelerometers, vibrational sensors, and other measuring devices for recording additional parameters. For example, the physiological sensors can also be configured to detect other types of patient physiological parameters and vibrational signals, such as tissue fluid levels, cardio-vibrations, pulmonary-vibrations, respiration-related vibrations of anatomical features in the airway path, patient movement, etc. Example physiological sensors can include ECG sensors including a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference.

In examples, the physiological sensors can include a heart rate sensor for detecting heart beats and monitoring the heart rate of the patient. For instance, such heart rate sensors can include the ECG sensors and associated circuitry described above. In some examples, the heart rate sensors can include a radio frequency based pulse detection sensor or a pulse oximetry sensor worn adjacent an artery of the patient. In implementations, the heart rate sensor can be worn about the wrist of a patient, for example, incorporated on and/or within a watch or a bracelet. In some examples, the heart rate sensor can be integrated within a patch adhesively coupled to the skin of the patient over an artery.

In some examples, the treatment electrodes 114, 214, 414 can also be configured to include sensors configured to detect ECG signals as well as other physiological signals of the patient. The ECG data acquisition and conditioning circuitry is configured to amplify, filter, and digitize these cardiac signals. One or more of the treatment electrodes 114, 214, 414 can be configured to deliver one or more therapeutic defibrillating shocks to the body of the patient when the medical device determines that such treatment is warranted based on the signals detected by the ECG sensing electrodes 112, 212, 412 and processed by the processor 218. Example treatment electrodes 114, 214, 414 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). The therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

FIG. 7 illustrates an example component-level view of the controller 220. As shown in FIG. 7, the controller 220 can include a therapy delivery circuit 1130 including a polarity switching component such as an H-bridge 1228, a data storage 1207, a network interface 1206, a user interface 1208 at least one battery 1140, a sensor interface 1212 that includes, for example, an ECG data acquisition and conditioning circuit, an alarm manager 1214, at least one processor 218, and one or more capacitors 1135. A patient monitoring medical device can include components like those described with regard to FIG. 7, but does not include the therapy delivery circuit 1130. Alternatively, a patient monitoring medical device can include components like those described with regard to FIG. 7, but includes a switching mechanism for rendering the therapy delivery circuit 1130 inoperative. For example, the processor 218 can prompt the switching mechanism to render the therapy delivery circuit 1130 inoperative when the second wearable portion 215 is not connected to the controller 220.

The therapy delivery circuit 1130 is coupled to two or more treatment electrodes configured to provide therapy to the patient. For example, the therapy delivery circuit 1130 includes, or is operably connected to, circuitry components that are configured to generate and provide the therapeutic shock. The circuitry components include, for example, resistors, one or more capacitors, relays and/or switches, an electrical bridge such as an H-bridge 1228 (e.g., an H-bridge including a plurality of insulated gate bipolar transistors or IGBTs that deliver and truncate a therapy pulse), voltage and/or current measuring components, and other similar circuitry arranged and connected such that the circuitry work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, each of the treatment electrodes 114, 214, 414 has a conductive surface adapted for placement adjacent the patient's skin and has an impedance reducing means contained therein or thereon for reducing the impedance between a treatment electrode and the patient's skin. In implementations, each of the treatment electrodes can include a conductive impedance reducing adhesive layer, such as a breathable anisotropic conductive hydrogel disposed between the treatment electrodes and the torso of the patient. In implementations, a patient-worn cardiac monitoring and treatment device may include gel deployment circuitry configured to cause the delivery of conductive gel substantially proximate to a treatment site (e.g., a surface of the patient's skin in contact with the treatment electrode 114) prior to delivering therapeutic shocks to the treatment site. As described in U.S. Pat. No. 9,008,801, titled "WEARABLE THERAPEUTIC DEVICE," issued on Apr. 14, 2015 (hereinafter the "'801 Patent"), which is incorporated herein by reference in its entirety, the gel deployment circuitry can be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry can be coupled to or integrated with each of the treatment electrodes 114, 214, 414.

When a treatable cardiac condition is detected and no patient response is received after device prompting, the gel deployment circuitry can be signaled to deploy the conductive gel. In some examples, the gel deployment circuitry can be constructed as one or more separate and independent gel deployment modules. Such modules can be configured to receive removable and/or replaceable gel cartridges (e.g., cartridges that contain one or more conductive gel reservoirs). As such, the gel deployment circuitry can be permanently disposed in the device as part of the therapy delivery systems, while the cartridges can be removable and/or replaceable.

In some implementations, the gel deployment modules can be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry can be removable and/or replaceable. In some examples, the gel deployment pack, including the one or more gel reservoirs and associated gel deployment circuitry, and the treatment electrode can be integrated into a treatment electrode assembly that can be removed and replaced as a single unit either after use, or if damaged or broken.

Continuing with the description of the example medical device of FIG. 7, in implementations, the one or more capacitors 1135 is a plurality of capacitors (e.g., two, three, four or more capacitors) comprising a capacitor bank 1402. These capacitors 1135 can be switched into a series connection during discharge for a defibrillation pulse. For example, four capacitors of approximately 650 $\mu$F can be used. In one implementation, the capacitors can have between 200 to 2500 volt surge rating and can be charged in approximately 5 to 30 seconds from a battery 1140 depending on the amount of energy to be delivered to the patient.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

The data storage 1207 can include one or more of non-transitory computer readable media, such as flash memory, solid state memory, magnetic memory, optical memory, cache memory, combinations thereof, and others. The data storage 1207 can be configured to store executable instructions and data used for operation of the medical device. In certain implementations, the data storage 1207 can include executable instructions that, when executed, are configured to cause the processor 218 to perform one or more functions.

In some examples, the network interface 1206 can facilitate the communication of information between the medical device and one or more other devices or entities over a communications network. For example, the network interface 1206 can be configured to communicate with a remote computing device such as a remote server or other similar computing device. The network interface 1206 can include communications circuitry for transmitting data in accordance with a BLUETOOTH wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a WI-FI communications link based on the IEEE 802.11 standard.

In certain implementations, the user interface 1208 can include one or more physical interface devices such as input devices, output devices, and combination input/output devices and a software stack configured to drive operation of the devices. These user interface elements may render visual, audio, and/or tactile content. Thus, the user interface 1208 may receive input or provide output, thereby enabling a user to interact with the medical device. In some implementations, the user interface 1208 can be implemented as a wearable article or as a hand-held user interface device (for example, wearable articles including the patient interface pod 40 of FIG. 1 and the wrist and arm worn remote devices.) For instance, a hand-held user interface device can be a smartphone or other portable device configured to communicate with the processor 218 via the network interface 1206. In an implementation, the hand-held user interface device may also be the intermediary device for facilitating the transfer of information from the device to a remote server.

As described, the medical device can also include at least one battery 1140 configured to provide power to one or more components, such as the one or more capacitors 1135. The battery 1140 can include a rechargeable multi-cell battery pack. In one example implementation, the battery 1140 can include three or more 2200 mAh lithium ion cells that provide electrical power to the other device components. For example, the battery 1140 can provide its power output in a range of between 20 mA to 1000 mA (e.g., 40 mA) output and can support 24 hours, 48 hours, 72 hours, or more, of runtime between charges. As previously descried in detail, in certain implementations, the battery capacity, runtime, and type (e.g., lithium ion, nickel-cadmium, or nickel-metal hydride) can be changed to best fit the specific application of the medical device.

The sensor interface 1202 can be coupled to one or more sensors configured to monitor one or more physiological parameters of the patient. As shown in FIG. 7 the sensors can be coupled to the medical device controller (e.g., processor 218) via a wired or wireless connection. The sensors can include one or more sensing electrodes (e.g., ECG sensing electrode 212), vibrations sensors 1224, and tissue fluid monitors 1226 (e.g., based on ultra-wide band radiofrequency devices). For example, the sensor interface 1202 can include ECG circuitry (such as ECG acquisition and conditioning circuitry) and/or accelerometer circuitry, which are each configured to receive and condition the respective sensor signals.

The sensing electrodes can monitor, for example, a patient's ECG information. For example, the sensing electrodes of FIG. 7 can be ECG sensing electrodes 212 and can include conductive electrodes with stored gel deployment (e.g., metallic electrodes with stored conductive gel configured to be dispersed in the electrode-skin interface when needed), conductive electrodes with a conductive adhesive layer, or dry electrodes (e.g., a metallic substrate with an oxide layer in direct contact with the patient's skin). The sensing electrodes can be configured to measure the patient's ECG signals. The sensing electrodes can transmit information descriptive of the ECG signals to the sensor interface 1202 for subsequent analysis.

The vibrations sensors 1224 can detect a patient's cardiac or pulmonary (cardiopulmonary) vibration information. For example, the cardiopulmonary vibrations sensors 1224 can be configured to detect cardio-vibrational biomarkers in a cardio-vibrational signal, including any one or all of S1, S2, S3, and S4 cardio-vibrational biomarkers. From these cardio-vibrational biomarkers, certain electromechanical metrics can be calculated, including any one or more of electromechanical activation time (EMAT), percentage of EMAT (% EMAT), systolic dysfunction index (SDI), left ventricular diastolic perfusion time (LDPT), and left ventricular systolic time (LVST). The cardiopulmonary vibrations sensors 1224 may also be configured to detect heart wall motion, for example, by placement of the cardiopulmonary vibrations sensor 1224 in the region of the apical beat.

The vibrations sensors 1224 can include an acoustic sensor configured to detect vibrations from a subject's cardiac or pulmonary (cardiopulmonary) system and provide an output signal responsive to the detected vibrations of the targeted organ. For instance, in some implementations, the vibrations sensors 1224 are able to detect vibrations generated in the trachea or lungs due to the flow of air during breathing. The vibrations sensors 1224 can also include a multi-channel accelerometer, for example, a three channel accelerometer configured to sense movement in each of three orthogonal axes such that patient movement/body position can be detected. The vibrations sensors 1224 can transmit information descriptive of the cardiopulmonary vibrations information or patient position/movement to the sensor interface 1202 for subsequent analysis.

The tissue fluid monitors 1226 can use radio frequency (RF) based techniques to assess changes of accumulated fluid levels over time. For example, the tissue fluid monitors 1226 can be configured to measure fluid content in the lungs (e.g., time-varying changes and absolute levels), for diagnosis and follow-up of pulmonary edema or lung congestion in heart failure patients. The tissue fluid monitors 1226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 1226 can transmit information descriptive of the tissue fluid levels to the sensor interface 1202 for subsequent analysis.

The sensor interface 1202 can be coupled to any one or combination of sensing electrodes/other sensors to receive other patient data indicative of patient parameters. Once data from the sensors has been received by the sensor interface 1202, the data can be directed by the processor 218 to an appropriate component within the medical device. For example, if cardiac data is collected by the cardiopulmonary vibrations sensor 1224 and transmitted to the sensor interface 1202, the sensor interface 1202 can transmit the data to the processor 218 which, in turn, relays the data to a cardiac event detector. The cardiac event data can also be stored on the data storage 1207.

An alarm manager 1214 can be configured to manage alarm profiles and notify one or more intended recipients of events specified within the alarm profiles as being of interest to the intended recipients. These intended recipients can include external entities such as users (e.g., patients, physicians, other caregivers, patient care representatives, and other authorized monitoring personnel) as well as computer systems (e.g., monitoring systems or emergency response systems). The alarm manager 1214 can be implemented using hardware or a combination of hardware and software. For instance, in some examples, the alarm manager 1214 can be implemented as a software component that is stored within the data storage 1207 and executed by the processor 218. In this example, the instructions included in the alarm manager 1214 can cause the processor 218 to configure alarm profiles and notify intended recipients according to the configured alarm profiles. In some examples, alarm manager 1214 can be an application-specific integrated circuit (ASIC) that is coupled to the processor 218 and configured to manage alarm profiles and notify intended recipients using alarms specified within the alarm profiles. Thus, examples of alarm manager 1214 are not limited to a particular hardware or software implementation.

In some implementations, the processor 218 includes one or more processors (or one or more processor cores) that each are configured to perform a series of instructions that result in manipulated data and/or control the operation of the other components of the medical device. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to a specific input stimulus in a specific way and generates a corresponding output based on that input stimulus. In some example cases, the processor 218 can proceed through a sequence of logical transitions in which various internal register states and/or other bit cell states internal or external to the processor 218 can be set to logic high or logic low. The processor 218 can be configured to execute a function stored in software. For example, such software can be stored in a data store coupled to the processor 218 and configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor 218 can be a multi-core processor, e.g., a processor having two or more processing cores. The processor can be an Advanced RISC Machine (ARM) processor such as a 32-bit ARM processor or a 64-bit ARM processor. The processor can execute an embedded operating system and include services provided by the operating system that can be used for file system manipulation, display & audio generation, basic networking, firewalling, data encryption and communications.

In implementations, the therapy delivery circuit 1130 includes, or is operably connected to, circuitry components that are configured to generate and provide the therapeutic shock. As described previously, the circuitry components include, for example, resistors, one or more capacitors 1135, relays and/or switches, an electrical bridge such as an H-bridge 1228 (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 1130 and under control of one or more processors (e.g., processor 218) to provide, for example, one or more pacing or defibrillation therapeutic pulses.

In implementations, the device further includes a source of electrical energy, for example, the one or more capacitors 1135, that stores and provides energy to the therapy delivery circuit 1130. The one or more therapeutic pulses are defibrillation pulses of electrical energy, and the one or more treatable arrhythmias include ventricular fibrillation and ventricular tachycardia. In implementations, the one or more therapeutic pulses are biphasic exponential pulses. Such therapeutic pulses can be generated by charging the one or more capacitors 1135 and discharging the energy stored in the one or more capacitors 1135 into the patient. For example, the therapy delivery circuit 1130 can include one or more power converters for controlling the charging and discharging of the one or more capacitors 1135. In some implementations, the discharge of energy from the one or more capacitors 1135 can be controlled by, for example, an H-bridge that controls the discharge of energy into the body of the patient, like the H-bridge circuit described in U.S. Pat. No. 6,280,461, titled "PATIENT-WORN ENERGY DELIVERY APPARATUS," issued on Aug. 28, 2001, and U.S. Pat. No. 8,909,335, titled "METHOD AND APPARATUS FOR APPLYING A RECTILINEAR BIPHASIC POWER WAVEFORM TO A LOAD," issued on Dec. 9, 2014, each of which is hereby incorporated herein by reference in its entirety.

Figure 16:
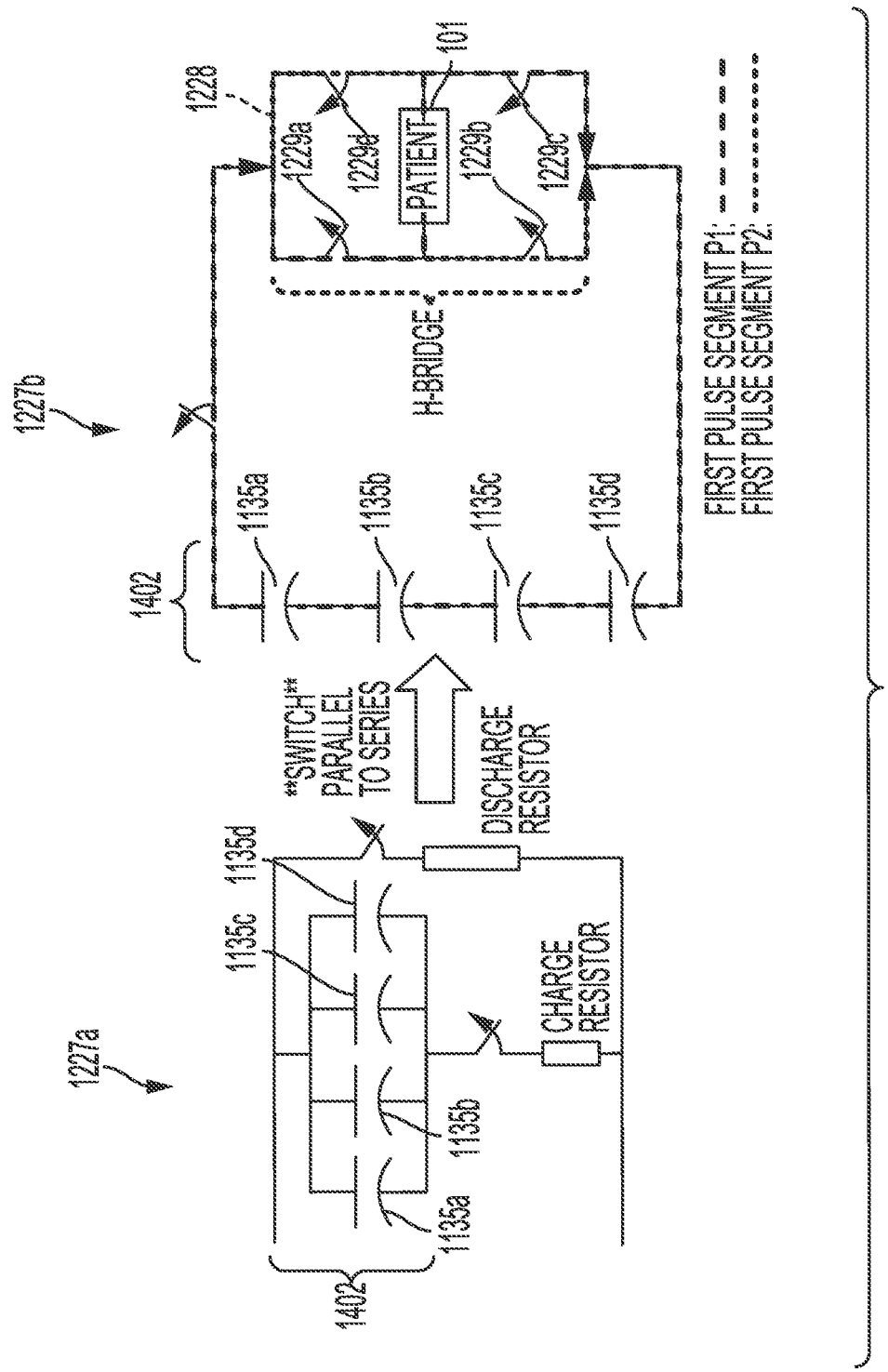
FIG. 16 depicts a schematic diagram of an embodiment of electrical components of a patient-worn cardiac monitoring and treatment device.

As shown in the embodiment to FIG. 16, the H-bridge 1228 is electrically coupled to a capacitor bank 1402 including four capacitors 1135*a-d* that are charged in parallel at a preparation phase 1227*a* and discharged in series at a treatment phase 1227*b*. In some implementations, the capacitor bank 1402 can include more or fewer than four capacitors 1135. During the treatment phase 1227*b*, the H-bridge 1228 applies a therapeutic pulse that causes current to flow through the torso 5 of a patient 101 in desired directions for desired durations. The H-bridge 1228 includes H-bridge switches 1229*a-d* that are opened and closed selectively by a switching transistor such as insulated gate bipolar transistors (IGBTs), silicon carbide field effect transistors (SiC FETs), metal-oxide semiconductor field effect transistors (MOSFETS), silicon-controlled rectifiers (SCRs), or other high current switching devices. Switching a pair of transistors to a closed position, for example switches 1229*a* and 1229*c*, enables current to flow in a first direction for first pulse segment P1. Opening switches 1229*a* and 1229*c* and closing switches 1229*b* and 1229*d* enables current to flow through the torso 5 of the patient 101 in a second pulse segment P2 directionally opposite the flow of the first pulse segment P1.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A cardiac monitoring and treatment system, comprising:
   a controller comprising at least one processor;
   a first wearable portion, comprising
      an elongated strap configured to encircle a thoracic region of a patient, the elongated strap being configured to be immobilized relative to a skin surface of the thoracic region of the patient by exerting one or more compression forces against the thoracic region,
         wherein the elongated strap is configured to exert the one or more compression forces in a range from 0.025 psi to 0.75 psi,
      a plurality of ECG sensing electrodes disposed about the elongated strap, the plurality of ECG sensing electrodes configured to sense an ECG signal of the patient,
      one or more receiving ports configured to receive one or more additional components including at least one of a treatment electrode or an additional sensor, and
      a plurality of conductive wires, the plurality of conductive wires configured to couple the plurality of ECG sensing electrodes and the one or more receiving ports with the controller; and
   a second wearable portion separate from the first wearable portion, the second wearable portion configured to be worn over at least one shoulder of the patient, comprising
      a wearable substrate,
      one or more treatment electrodes disposed on the wearable substrate, the one or more treatment electrodes comprising a corresponding conductive surface configured to contact an anterior area and a posterior area of the thoracic region of the patient, and
      at least one conductive wire configured to releasably connect the one or more treatment electrodes to the controller.

2. The system of claim 1, wherein the second wearable portion is configured to be worn for a cumulative duration less than or equal to a duration of wear of the first wearable portion.

3. The system of claim 1, wherein the second wearable portion comprises a compression force relatively lower than the one or more compression forces of the elongated strap.

4. The system of claim 1, further comprising an ECG acquisition circuit in communication with the plurality of ECG sensing electrodes and the at least one processor and configured to provide ECG information for the patient based on the sensed ECG signal.

5. The system of claim 4, wherein the at least one processor is configured to
   predict a likelihood of a cardiac event based on an analysis of the ECG information, and
   provide a notification to the patient to wear the second wearable portion upon detecting an impending cardiac event.

6. The system of claim 1, wherein the elongated strap is sized to fit about the thoracic region by matching a length of the elongated strap to one or more circumferential measurements of the thoracic region during an initial patient fitting.

7. The system of claim 1, wherein elongated strap dimensions are derived from a 3D scan of the thoracic region such that the elongated strap is sized to fit proportions, dimensions, and shape of the thoracic region.

8. The system of claim 7, wherein at least a portion of the elongated strap is 3D printed to at least one of body proportions, body shape, body posture, or linear surface measurements of the thoracic region of the patient.

9. The system of claim 1, wherein the elongated strap comprises an adjustable latching mechanism configured to secure the elongated strap about the thoracic region of the patient.

10. The system of claim 1, wherein the elongated strap comprises a breathable skin-facing layer having a moisture vapor transmission rate (MVTR) of between about 600 $g/m^2/day$ and about 1,400 $g/m^2/day$.

11. The system of claim 1, wherein the elongated strap comprises a breathable skin-facing layer having a moisture vapor transmission rate (MVTR) of between about 100 $g/m^2/day$ and about 1,400 $g/m^2/day$.

12. The system of claim 1, wherein the one or more compression forces are in a range from 0.05 to 0.70 psi.

13. The system of claim 1, wherein the one or more compression forces are in a range from 0.075 to 0.675 psi.

14. The system of claim 1, wherein the one or more compression forces are in a range from 0.1 to 0.65 psi.

15. The system of claim 1, wherein the system is configured to provide a notification of the one or more compression forces exerted by the elongated strap.

16. The system of claim 15, further comprising one or more pressure sensors distributed on the elongated strap, wherein the notification of the one or more compression forces exerted by the elongated strap is based on data from the one or more pressure sensors.

17. The system of claim 16, wherein the one or more pressure sensors comprise one or more force sensitive resistors.

18. The system of claim 1, wherein the elongated strap comprises a vertical span in a range of 1 to about 15 centimeters along at least 50 percent of a length of the elongated strap.

19. The system of claim 1, wherein the elongated strap comprises a vertical span in a range of 2 to about 12 centimeters along at least 50 percent of a length of the elongated strap.

20. A cardiac monitoring and treatment system, comprising:
   a controller comprising at least one processor;
   a first wearable portion, comprising
      an elongated strap configured to encircle a thoracic region of a patient, the elongated strap being configured to be immobilized relative to a skin surface of the thoracic region of the patient by exerting one or more compression forces against the thoracic region, wherein the elongated strap comprises a breathable skin-facing layer having a moisture vapor transmission rate (MVTR) of between about 100 g/m$^2$/day and about 1,400 g/m$^2$/day,
 a plurality of ECG sensing electrodes disposed about the elongated strap, the plurality of ECG sensing electrodes configured to sense an ECG signal of the patient,
 one or more receiving ports configured to receive one or more additional components including at least one of a treatment electrode or an additional sensor, and
 a plurality of conductive wires, the plurality of conductive wires configured to couple the plurality of ECG sensing electrodes and the one or more receiving ports with the controller; and
a second wearable portion separate from the first wearable portion, the second wearable portion configured to be worn over at least one shoulder of the patient, comprising
 a wearable substrate,
 one or more treatment electrodes disposed on the wearable substrate, the one or more treatment electrodes comprising a corresponding conductive surface configured to contact an anterior area and a posterior area of the thoracic region of the patient, and
 at least one conductive wire configured to releasably connect the one or more treatment electrodes to the controller.

21. The system of claim 20, wherein the MVTR of the breathable skin-facing layer is between about 600 g/m$^2$/day and about 1,400 g/m$^2$/day.

22. The system of claim 20, wherein the second wearable portion comprises a compression force relatively lower than the one or more compression forces of the elongated strap.

23. The system of claim 20, further comprising an ECG acquisition circuit in communication with the plurality of ECG sensing electrodes and the at least one processor and configured to provide ECG information for the patient based on the sensed ECG signal.

24. The system of claim 23, wherein the at least one processor is configured to
 predict a likelihood of a cardiac event based on an analysis of the ECG information, and
 provide a notification to the patient to wear the second wearable portion upon detecting an impending cardiac event.

25. The system of claim 20, wherein the system is configured to provide a notification of the one or more compression forces exerted by the elongated strap.

26. The system of claim 25, further comprising one or more pressure sensors distributed on the elongated strap, wherein the notification of the one or more compression forces exerted by the elongated strap is based on data from the one or more pressure sensors.

27. The system of claim 26, wherein the one or more pressure sensors comprise one or more force sensitive resistors.

* * * * *